United States Patent [19]
Takeda et al.

[11] Patent Number: 5,578,627
[45] Date of Patent: Nov. 26, 1996

[54] 1,2-BENZOISOXAZOLE DERIVATIVE OR ITS SALT AND BRAIN-PROTECTING AGENT COMPRISING THE SAME

[75] Inventors: Kenji Takeda; Nobuo Terashima; Joji Nakano, all of Toyama; Hisashi Minami, Toda; Toyokazu Kobayashi, Toyama; Kunikazu Furuhata, Namerikawa; Tadakazu Takakura, Toyama; Makoto Takata, Toda; Hiroyo Kawafuchi, Nakaniikawa-gun; Toru Hiraiwa, Toyama, all of Japan

[73] Assignee: Toyama Chemical Co., Ltd., Tokyo, Japan

[21] Appl. No.: 411,667

[22] PCT Filed: Oct. 27, 1993

[86] PCT No.: PCT/JP93/01549

§ 371 Date: Apr. 12, 1995

§ 102(e) Date: Apr. 12, 1995

[87] PCT Pub. No.: WO94/10158

PCT Pub. Date: May 11, 1994

[30] Foreign Application Priority Data

| Oct. 25, 1992 | [JP] | Japan | 4-312743 |
| Jul. 2, 1993 | [JP] | Japan | 5-238688 |
| Jul. 15, 1993 | [JP] | Japan | 5-197776 |

[51] Int. Cl.⁶ ............... A61K 31/405; C07D 209/10
[52] U.S. Cl. ............................ 514/379; 548/241
[58] Field of Search ................. 514/379; 548/241

[56] References Cited

PUBLICATIONS

CA 70:37702b Biological . . . 3–alkylaminoalkoxybenzisothiazoles., Vitali et al., p. 341, 1969.

CA 71:49831b Biological . . . 3–(alkylaminoalkoxy)–benzisothiazoles., Vitali et al., p. 383, 1969.

CA 72:31781w 1,2–Benzisothiazole . . . ethers. Vitali et al., p. 337, 1970.

*Primary Examiner*—Joseph McKane
*Attorney, Agent, or Firm*—Oblon, Spivak, McClelland, Maier & Neustadt, P.C.

[57] ABSTRACT

This invention relates to a 1,2-benzoisoxazole derivative represented by the following general formula (I) or its salt:

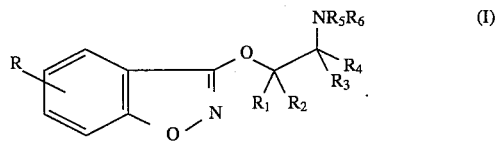

32 Claims, No Drawings

1,2-BENZOISOXAZOLE DERIVATIVE OR ITS SALT AND BRAIN-PROTECTING AGENT COMPRISING THE SAME

This application is a 371 of PCT/JP93/01549 filed Oct. 27, 1993.

TECHNICAL FIELD

This invention relates to a novel 1,2-benzoisoxazole derivative or its salt or a brain-protecting agent comprising the same.

BACKGROUND ART

In the acute phase of cerebral circulatory disturbance, the principal object has heretofore been put in the treatment of which the primary purpose is life-saving, and substantially no treatment for relieving sequelae has been effected. On the other hand, in the chronic phase, various cerebral circulation and metabolism ameliorants have been used. However, since the symptomatology has already been fixed, an improvement of neurological symptoms and activities of daily living which improvement has been most desired has not been observed with these cerebral circulation and metabolism ameliorants.

Therefore, it has now become considered that an adequate treatment in the acute phase can relieve the sequelae, particularly neurological sequelae.

Accordingly, there has been desired a development of a compound which has a brain-protecting action by which cell death in the cerebral ischemia is depressed, is weak in such central depressant action as to make the whole body control of patient difficult, and is further chemically stable.

DISCLOSURE OF THE INVENTION

Under such circumstances, the present inventors have made extensive research and have consequently found that a compound obtained by introducing a group represented by the following formula:

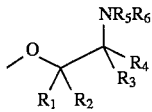

wherein $R_1$, $R_2$, $R_4$, $R_5$ and $R_6$ have the same meanings as mentioned hereinafter, into 1,2-benzoisoxazole at the 3-position, namely a novel 1,2-benzoisoxazole derivative represented by the general formula (I) mentioned hereinafter or its salt, is a compound which has an excellent brain-protecting action by which cell death in the cerebral ischemic state is depressed, further is weak in central depressant action and hence, is useful as a curing agent for cerebral circulatory disturbance not only in the acute phase but also in the chronic phase, head injury sequelae and epilepsy, and is chemically stable, and further that it is useful as their precursor, whereby this invention has been completed.

An object of this invention is to provide a novel 1,2-benzoisoxazole derivative or its salt.

Also, another object of this invention is to provide a novel, chemically stable 1,2-benzoisoxazole derivative or its salt which has a brain-protecting action but is weak in central depressant action.

Moreover, a still another object of this invention is to provide a novel 1,2-benzoisoxazole derivative or its salt which is useful as a curing agent for cerebral circulatory disorder not only in the acute phase but also in the chronic phase, head injury sequelae and epilepsy.

According to this invention, there is provided a 1,2-benzoisoxazole derivative represented by the following general formula (I) or its salt:

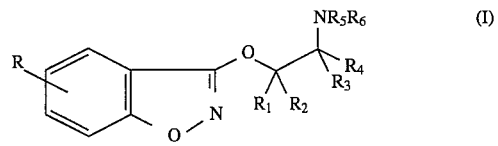

wherein R represents at least one member selected from hydrogen atom, halogen atoms, nitro group, cyano group, hydroxyl group and substituted or unsubstituted lower alkyl, lower alkenyl, lower alkynyl, aralkyl, aryl, lower alkyloxy, cycloalkyl, aralkyloxy, aryloxy, amino, lower acyl, arylcarbonyl, lower alkanesulfonyl, arenesulfonyl, lower alkylthio, carbamoyl, lower alkylene, lower alkenylene and heterocyclic groups; $R_1$ and $R_2$, which may be the same or different, represent hydrogen atoms or substituted or unsubstituted lower alkyl groups; $R_3$ represents a hydrogen atom or a substituted or unsubstituted lower alkyl, aryl, aralkyl or heterocyclic group; $R_4$ represents a substituted or unsubstituted lower alkyl, aryl or heterocyclic group, or alternatively $R_3$ and $R_4$, when taken together, represent a lower alkylene group; $R_5$ and $R_6$, which may be the same or different, represent hydrogen atoms or substituted or unsubstituted lower alkyl, lower alkenyl, lower alkynyl, lower acyl, lower alkyloxycarbonyl or aralkyl groups.

This invention is described in detail below.

In the present specification, unless otherwise specified, each term has the following meaning. The halogen atom represents fluorine atom, chlorine atom, bromine atom, iodine atom and the like; the lower alkyl group represents $C_{1-7}$ alkyl groups such as methyl, ethyl, n-propyl, isopropyl, n-butyl, isobutyl, tert-butyl, pentyl, hexyl, heptyl and the like; the lower alkenyl group represents $C_{2-7}$ alkenyl groups such as vinyl, allyl, propenyl and the like; the lower alkynyl group represents $C_{2-7}$ alkynyl groups such as ethynyl, propynyl and the like; the cycloalkyl group represents $C_{3-7}$ cycloalkyl groups such as cyclopropyl, cyclobutyl, cyclopentyl, cyclohexyl and the like; the lower acyl group represents $C_{1-7}$ acyl groups such as formyl, acetyl, propionyl, butyryl, valeryl and the like; the aryl group represents phenyl group, naphthyl group and the like; the lower alkylene group represents $C_{1-7}$ alkylene groups such as methylene, ethylene and the like; the lower alkenylene group represents $C_{2-7}$ alkenylene groups such as vinylene, propenylene, butadienylene and the like; the aralkyl group represents aryl-$C_{1-7}$ alkyl groups such as benzyl, benzhydryl, trityl and the like; lower alkylamino group represents $C_{1-7}$ alkylamino groups such as methylamino, ethylamino, propylamino and the like; the di-lower alkylamino group represents di-$C_{1-7}$; alkylamino groups such as dimethylamino, diethylamino, ethylmethylamino and the like; the lower alkylthio group represents $C_{1-7}$ alkylthio groups such as methylthio, ethylthio, n-propylthio, tert-butylthio, pentylthio and the like; the lower alkanesulfinyl group represents $C_{1-7}$ alkanesulfinyl groups such as methanesulfinyl, ethanesulfinyl and the like; the lower alkanesulfonyl group represents $C_{1-7}$ alkanesulfonyl groups such as methanesulfonyl, ethanesulfonyl and the like; the arenesulfonyl group represents, for example, benzenesulfonyl, toluenesulfonyl, naphthalenesulfonyl and the like; the heterocyclic group represents 5-membered or 6-membered heterocyclic groups containing at least one hetero atom selected from nitrogen, oxygen and sulfur atoms such as thienyl, furyl, oxazolyl, isoxazolyl, oxazolinyl, oxazolidinyl, thiazolyl, isothiazolyl, thiazolinyl, thiazolidinyl, imidazolyl, imidazolinyl, imidazolidinyl, thiadiazolyl, triazolyl, tetrazolyl, oxadiazolyl, pyrrolyl, pyrrolidinyl, piperidyl, piperazinyl, morpholinyl, thiomorpholinyl, pyridyl, dihydropyridyl, pyrazinyl, pyridazinyl, pyrimidinyl and the like as well as fused heterocyclic groups containing at least one hetero atom selected from nitrogen, oxygen and sulfur atoms such as benzofuranyl, benzothienyl, benzoxazolyl, benzoisoxazolyl, indolyl, benzothiazolyl, benzoisothiazolyl and the like; the lower alkyloxy group represents $C_{1-7}$ alkyloxy groups such as methoxy, ethoxy, n-propoxy, n-butoxy, pentyloxy and the like; the lower alkenyloxy group represents $C_{2-7}$ alkenyloxy groups such as vinyloxy, allyloxy, propenyloxy and the like; the lower alkynyloxy group represents $C_{2-7}$ alkynyloxy groups such as ethynyloxy, propynyloxy and the like; the cycloalkyloxy group represents $C_{3-7}$ cycloalkyl groups such as cyclopropyloxy, cyclobutyloxy, cyclopentyloxy, cyclohexyloxy and the like; the aryloxy group represents phenyloxy group, naphthyloxy group and the like; the aralkyloxy group represents aryl-$C_{1-7}$ alkyloxy groups such as benzyloxy, phenethyloxy and the like; the lower alkanesulfonyloxy group represents $C_{1-7}$ alkanesulfonyloxy groups such as methanesulfonyloxy, ethanesulfonyloxy and the like; the arenesulfonyloxy group represents, for example, benzenesulfonyloxy, toluenesulfonyloxy, naphthalenesulfonyloxy and the like; the heterocyclic oxy group represents, for example, thienyloxy, furyloxy, oxazolyloxy, isoxazolyloxy, thiazolyloxy, imidazolyloxy, pyrrolyloxy, pyrrolidinyloxy, piperidinyloxy, piperazinyloxy, morpholyloxy, thiomorpholyloxy, pyridyloxy, pyrimidyloxy and the like; the lower alkyloxycarbonyl group represents $C_{1-7}$ alkyloxycarbonyl groups such as methoxycarbonyl, ethoxycarbonyl, propoxycarbonyl, tert-butoxycarbonyl and the like; the arylcarbonyl group represents, for example, benzoyl, naphthoyl and the like; the di-lower alkylaminocarbonyl group represents di-$C_{1-7}$ alkylaminocarbonyl groups such as dimethylaminocarbonyl, diethylaminocarbonyl and the like; and the heterocyclic carbonyl group represents groups such as thienylcarbonyl, furylcarbonyl, oxazolylcarbonyl, isoxazolylcarbonyl, thiazolylcarbonyl, imidazolylcarbonyl, pyrrolylcarbonyl, pyrrolidinylcarbonyl, piperidinylcarbonyl, piperazylcarbonyl, morpholylcarbonyl, thiomorpholylcarbonyl, pyridylcarbonyl, pyrimidylcarbonyl and the like.

Also, the substituents of the substituted or unsubstituted lower alkyl, lower alkenyl, lower alkynyl, lower alkyloxy, cycloalkyl, aralkyloxy, lower acyl, arylcarbonyl, lower alkanesulfonyl, arenesulfonyl, lower alkylthio, lower alkylene, lower alkenylene or lower alkyloxycarbonyl group for R, $R_1$, $R_2$, $R_3$, $R_4$, $R_5$ and $R_6$ include, for example, halogen atoms, hydroxyl group, lower alkyl groups, lower alkylthio groups, lower alkyloxy groups, lower alkenyloxy groups, lower alkynyloxy groups, cycloalkyloxy groups, aralkyloxy groups, lower alkanesulfinyl groups, lower alkanesulfonyl groups, carbamoyl groups, carbamoyloxy groups, thiocarbamoyl groups, thiocarbamoyloxy groups, sulfamoyloxy groups, aryl groups, aryloxy groups, arylcarbonyl groups, heterocyclic groups, heterocyclic oxy groups, heterocyclic carbonyl groups, cyano group, amino group and the like.

Furthermore, the substituents of the substituted or unsubstituted aryl, aryloxy or aralkyl group for R, $R_3$, $R_4$, $R_5$ and $R_6$ include, for example, halogen atoms, hydroxyl group, lower alkyl groups, lower alkyloxy groups, carbamoyloxy group, arenesulfonyl groups, arenesulfonyloxy groups, nitro group, amino group, lower alkylamino groups, di-lower alkylamino groups and the like.

Moreover, the substituents of the substituted or unsubstituted carbamoyl group for R include, for example, lower alkyl groups, lower alkenyl groups, lower alkynyl groups, cycloalkyl groups, amino group, lower alkyloxy groups, carbamoyl group, lower alkyloxycarbonyl groups and the like.

Also, the substituents of the substituted or unsubstituted amino group for R include, for example, lower alkyl groups, lower acyl groups, arylcarbonyl groups, lower alkyloxycarbonyl groups and the like.

Furthermore, the substituents of the substituted or unsubstituted heterocyclic group for R, $R_3$ and $R_4$ include, for example, halogen atoms, hydroxyl group, carboxyl group, lower alkyl groups, lower alkyloxy groups, lower alkyloxycarbonyl groups, lower alkylthio groups, lower alkanesulfinyl groups, lower alkanesulfonyl groups, carbamoyl group, carbamoyloxy group, aryl groups, heterocyclic groups, heterocyclic carbonyl groups, cyano group, amino group, oxo group and the like.

Moreover, the substituents of the substituted or unsubstituted lower alkyl group for $R_4$ include, for example, groups represented by the formula:

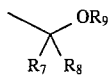

wherein $R_7$ and $R_8$ represent hydrogen atoms or substituted or unsubstituted lower alkyl groups; and $R_9$ represents a substituted or unsubstituted lower alkyl, lower alkenyl, lower alkynyl, cycloalkyl, aralkyl or carbamoyl groups.

In this case, the substituents of the substituted or unsubstituted lower alkyl group for $R_7$ and $R_8$; and the substituents of the substituted or unsubstituted lower alkyl, lower alkenyl, lower alkynyl and cycloalkyl groups for $R_9$ include, for example, halogen atoms, hydroxyl group, lower alkyloxy groups, aryl groups, cyano group, amino group and the like. The substituents of the substituted or unsubstituted aralkyl group for $R_9$ include, for example, halogen atoms, hydroxyl group, lower alkyl groups, nitro group and the like. The substituents of the substituted or unsubstituted carbamoyl group for $R_9$ include, for example, lower alkyl groups, lower alkenyl groups, lower alkynyl groups, cycloalkyl groups, amino group, lower alkyloxy groups, carbamoyl group, lower alkyloxycarbonyl groups and the like.

Each group for R and $R_1$ to $R_6$ may be substituted by at least one substituent of the above-mentioned substituents.

These substituents may further be substituted by a halogen atom, a nitro group, a cyano group, a hydroxyl group, a carboxyl group, an amino group, a lower alkyl group, a lower alkyloxy group, a lower alkyloxycarbonyl group, a lower alkylamino group, a di-lower alkylamino group, an aralkyl group, a cycloalkyl group, an aryl group, a di-lower alkylaminocarbonyl group, an arenesulfonyloxy group or a carbamoyl group.

The salts of the 1,2-benzoisoxazole derivative of the general formula (I) may be pharmaceutically acceptable salts, and include, for example, salts with organic and inorganic acids such as salts with mineral acids such as hydrochloric acid, hydrobromic acid, sulfuric acid, phosphoric acid and the like; salts with carboxylic acids such as formic acid, acetic acid, oxalic acid, fumaric acid, maleic acid, malic acid, tartaric acid and the like; salts with acidic amino acids such as aspartic acid, glutamic acid and the like; and salts with sulfonic acids such as methanesulfonic acid, toluenesulfonic acid, hydroxybenzenesulfonic acid, naphthalenesulfonic acid and the like, etc.; salts with alkali metals such as sodium, potassium and the like; etc.

When in the 1,2-benzoisoxazole derivative of the general formula (I), isomers (for example, optical isomers, geometrical isomers, tautomers and the like) are present, the compound of this invention includes all these isomers, and also includes hydrates, solvates and all crystalline forms.

In the compound of the general formula (I), preferable are 1,2-benzoisoxazole derivatives wherein R is a hydrogen atom or a halogen atom; $R_1$, $R_2$, $R_5$ and $R_6$ are hydrogen atoms; $R_3$ is a hydrogen atom or a lower alkyl group; and $R_4$ is a lower alkyl group or a group represented by the formula:

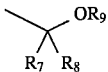

wherein $R_7$ and $R_8$ represent hydrogen atoms and $R_9$ represents a lower alkyl group or a carbamoyl group, or the salts thereof; and particularly preferable is 3-(2-amino-3-carbamoyloxypropoxy)-1,2-benzoisoxazole or its salt or 3-(2-amino-3-methoxypropoxy)-5-chloro-1,2-benzoisoxazole or its salt.

Representative compounds among the compounds of this invention include the following compounds:
- 3-(2-Amino-3-methoxypropoxy)-5-chloro-1,2-benzoisoxazole,
- 3-(2-Amino-3-methoxypropoxy)-5-benzyloxy-1,2-benzoisoxazole,
- 3-(2-Amino-3-carbamoyloxypropoxy)-5-chloro-1,2-benzoisoxazole,
- 3-(2-Amino-3-carbamoyloxybutoxy)-5-chloro-1,2-benzoisoxazole,
- 3-(2-Amino-3-carbamoyloxypropoxy)-5-vinyl-1,2-benzoisoxazole,
- 3-(2-Amino-3-carbamoyloxypropoxy)-5-butyl-1,2-benzoisoxazole,
- 3-(2-Amino-3-carbamoyloxypropoxy)-5-phenyl-1,2-benzoisoxazole,
- 3-(2-Amino-3-carbamoyloxypropoxy)-5,7-dichloro-1,2-benzoisoxazole,
- 3-(2-Amino-3-carbamoyloxypropoxy)-6-chloro-1,2-benzoisoxazole,
- 3-(2-Amino-3-carbamoyloxypropoxy)-5-iodo-1,2-benzoisoxazole,
- 3-(2-Amino-3-carbamoyloxypropoxy)-5-bromo-1,2-benzoisoxazole,
- 3-(2-Amino-3-carbamoyloxypropoxy)-1,2-benzoisoxazole,
- 3-(2-Amino-3-ethylcarbamoyloxypropoxy)-5-chloro-1,2-benzoisoxazole,
- 3-(2-Amino-3-methylthiopropoxy)-5-chloro-1,2-benzoisoxazole,
- 3-(2-Amino-2-phenylethoxy)-5-chloro-1,2-benzoisoxazole,
- 3-[2-amino-2-(4-dimethylaminophenyl)ethoxy]-5-chloro-1,2-benzoisoxazole,
- 3-[2-Amino-2-(3-methoxyphenyl)ethoxy]-5-chloro-1,2-benzoisoxazole,
- 3-[2-Amino-2-(4-methoxyphenyl)ethoxy]-5-chloro-1,2-benzoisoxazole,
- 3-[2-Amino-2-(3-pyridyl)ethoxy]-5-chloro-1,2-benzoisoxazole,
- 3-[2-Amino-2-(2-thienyl)ethoxy]-5-chloro-1,2-benzoisoxazole,
- 3-[2-Amino-2-[5-(2-methylthiazolyl)]ethoxy]-5-chloro-1,2-benzoisoxazole,
- 3-[2-Amino-2-[5-(2-aminothiazolyl)]ethoxy]-5-chloro-1,2-benzoisoxazole,
- 3-(1-Aminocyclopropylmethoxy)-5-chloro-1,2-benzoisoxazole,
- 3-(1-Aminocyclohexylmethoxy)-5-chloro-1,2-benzoisoxazole,
- 3-[2-Amino-2-(3-hydroxyphenyl)ethoxy]-5-chloro-1,2-benzoisoxazole,
- 3-[2-Amino-2-(3-carbamoyloxyphenyl)ethoxy]-5-chloro-1,2-benzoisoxazole,
- 3-[2-Amino-2-(4-hydroxyphenyl)ethoxy]-5-chloro-1,2-benzoisoxazole,
- 3-[2-Amino-2-(4-carbamoyloxyphenyl)ethoxy]-5-chloro-1,2-benzoisoxazole,
- 3-(2-Amino-2-phenylethoxy)-1,2-benzoisoxazole,
- 3-[2-Amino-2-(4-dimethylaminophenyl)ethoxy]-1,2-benzoisoxazole,
- 3-[2-Amino-2-(3-methoxyphenyl)ethoxy]-1,2-benzoisoxazole,
- 3-[2-Amino-2-(4-methoxyphenyl)ethoxy]-1,2-benzoisoxazole,
- 3-[2-Amino-2-(3-pyridyl)ethoxy]-1,2-benzoisoxazole,
- 3-[2-Amino-2-(2-thienyl)ethoxy]-1,2-benzoisoxazole,
- 3-[2-Amino-2-[5-(2-methylthiazolyl)]ethoxy]-1,2-benzoisoxazole,
- 3-[2-Amino-2-[5-(2-aminothiazolyl)]ethoxy]-1,2-benzoisoxazole,
- 3-(1-Aminocyclopropylmethoxy)-1,2-benzoisoxazole,
- 3-(1-Aminocyclohexylmethoxy)-1,2-benzoisoxazole,
- 3-[2-Amino-2-(3-hydroxyphenyl)ethoxy]-1,2-benzoisoxazole,
- 3-[2-Amino-2-(3-carbamoyloxyphenyl)ethoxy]-1,2-benzoisoxazole,
- 3-[2-Amino-2-(4-hydroxyphenyl)ethoxy]-1,2-benzoisoxazole,
- 3-[2-Amino-2-(4-carbamoyloxyphenyl)ethoxy]-1,2-benzoisoxazole,
- 3-(2-Aminopentyloxy)-5-chloro-1,2-benzoisoxazole,
- 3-(2-Amino-3-methylbutoxy)-5-chloro-1,2-benzoisoxazole,
- 3-(2-Amino-3-methanesulfinylpropoxy)-5-chloro-1,2-benzoisoxazole,
- 3-(2-Amino-3-methanesulfonylpropoxy)-5-chloro-1,2-benzoisoxazole,
- 3-(2-Aminopropoxy)-5-chloro-1,2-benzoisoxazole,
- 3-(2-Aminobutoxy)-5-chloro-1,2-benzoisoxazole,
- 3-(2-Amino-4-methylpentyloxy)-5-chloro-1,2-benzoisoxazole,
- 3-(2-amino-3-methylpentyloxy)-5-chloro-1,2-benzoisoxazole,
- 3-(2-amino-3,3-dimethylbutoxy)-5-chloro-1,2-benzoisoxazole,
- 3-(2-Amino-3-phenylpropoxy)-5-chloro-1,2-benzoisoxazole,
- 3-(2-Amino-3-fluoropropoxy)-5-chloro-1,2-benzoisoxazole,
- 3-(2-Amino-3-morpholinopropoxy)-5-chloro-1,2-benzoisoxazole,
- 3-(2-Amino-4-methoxybutoxy)-5-chloro-1,2-benzoisoxazole,
- 3-(2-Amino-4-methylthiobutoxy)-5-chloro-1,2-benzoisoxazole,
- 3-(2-Amino-3-carbamoylpropoxy)-5-chloro-1,2-benzoisoxazole,
- 3-(2-Amino-3-piperidinocarbonylpropoxy)-5-chloro-1,2-benzoisoxazole,
- 3-(2-Amino-4-carbamoylbutoxy)-5-chloro-1,2-benzoisoxazole,

- 3-(2-Aminopentyloxy)-5-methyl-1,2-benzoisoxazole,
- 3-(2-Aminopentyloxy)-5-methoxy-1,2-benzoisoxazole,
- 3-(2-Aminopropoxy)-1,2-benzoisoxazole,
- 3-(2-Aminobutoxy)-1,2-benzoisoxazole,
- 3-(2-Aminopentyloxy)-1,2-benzoisoxazole,
- 3-(2-Amino-3-methylbutoxy)-1,2-benzoisoxazole,
- 3-(2-Amino-3-methylthiopropoxy)-1,2-benzoisoxazole,
- 3-(2-Amino-3-methanesulfinylpropoxy)-1,2-benzoisoxazole,
- 3-(2-Amino-3-methanesulfonylpropoxy)-1,2-benzoisoxazole,
- 3-(2-Amino-4-methylpentyloxy)-1,2-benzoisoxazole,
- 3-(2-Amino-3-methylpentyloxy)-1,2-benzoisoxazole,
- 3-(2-Amino-3,3-dimethylbutoxy)-1,2-benzoisoxazole,
- 3-(2-Amino-3-phenylpropoxy)-1,2-benzoisoxazole,
- 3-(2-Amino-3-fluoropropoxy)-1,2-benzoisoxazole,
- 3-(2-Amino-3-morpholinopropoxy)-1,2-benzoisoxazole,
- 3-(2-Amino-4-methoxybutoxy)-1,2-benzoisoxazole,
- 3-(2-Amino-4-methylthiobutoxy)-1,2-benzoisoxazole,
- 3-(2-Amino-3-carbamoylpropoxy)-1,2-benzoisoxazole,
- 3-(2-Amino-3-piperidinocarbonylpropoxy)-1,2-benzoisoxazole,
- 3-(2-Amino-4-carbamoylbutoxy)-1,2-benzoisoxazole,
- 3-(2-Amino-2-methylpropoxy)-5-chloro-1,2-benzoisoxazole,
- 3-(2-Amino-2-methylpropoxy)-1,2-benzoisoxazole,
- 3-[2-Amino-3-(3-hydroxy-5-isoxazolyl)propoxy]-5-chloro-1,2-benzoisoxazole,
- 3-[2-Amino-3-(3-hydroxy-5-isoxazolyl)propoxy]-1,2-benzoisoxazole,
- 3-(2-Amino-2-ethylbutoxy)-5-chloro-1,2-benzoisoxazole,
- 3-(2-Amino-2-methylbutoxy)-5-chloro-1,2-benzoisoxazole,
- 3-(2-Amino-2-methylbutoxy)-5-bromo-1,2-benzoisoxazole,
- 3-(2-Amino-2-methylpropoxy)-5-n-butyl-1,2-benzoisoxazole,
- 3-(2-Amino-2-methylpropoxy)-5-fluoro-1,2-benzoisoxazole,
- 3-(2-Amino-2-methylpropoxy)-5-benzyloxy-1,2-benzoisoxazole,
- 3-(2-Amino-2-methylbutoxy)-1,2-benzoisoxazole, and
- 3-(2-Amino-2-ethylbutoxy)-1,2-benzoisoxazole,

PRODUCTION PROCESS IN INDUSTRY

An explanation is made below of a process for producing the 1,2-benzoisoxazole derivative of the general formula (I) or its salt.

The 1,2-benzoisoxazole derivative of the general formula (I) or its salt can be produced in a manner known per se, for example, the production processes shown below.

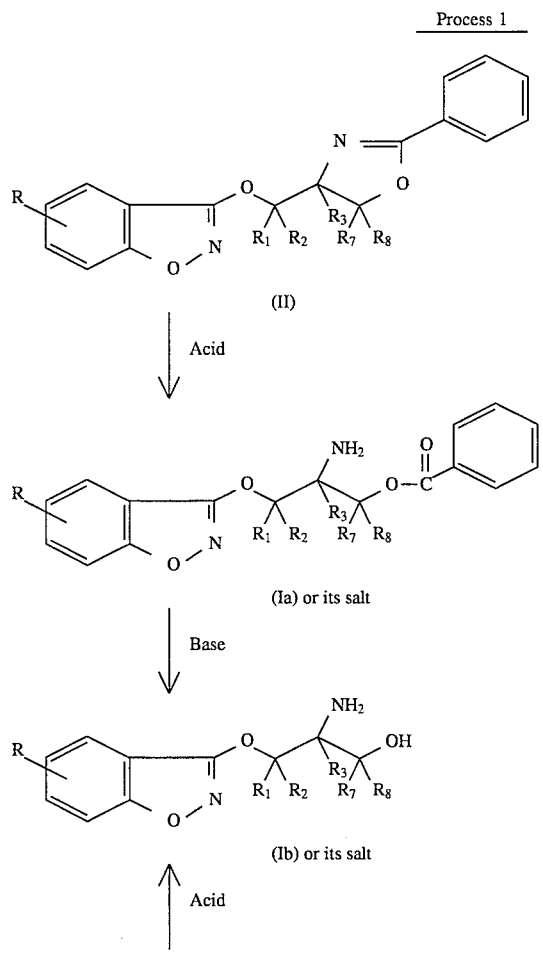

Process 1

-continued
Process 1
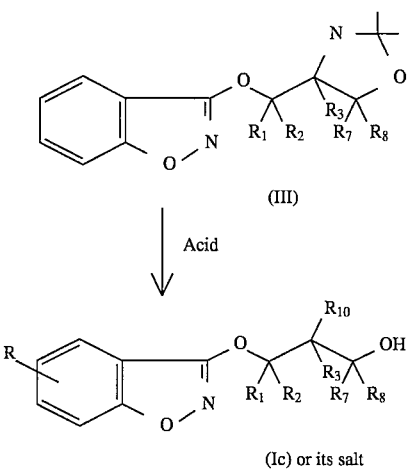
(III)
↓ Acid
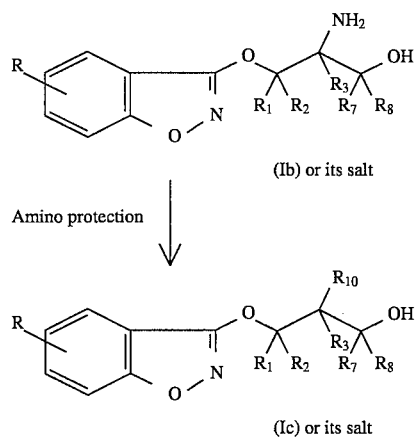
(Ic) or its salt
Process 2
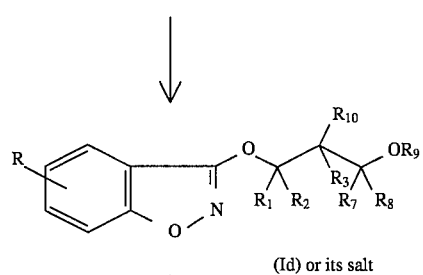
(Ib) or its salt
Amino protection ↓
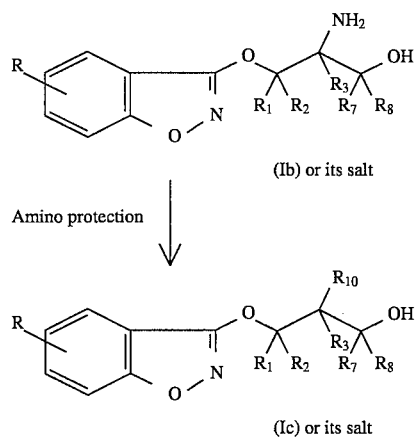
(Ic) or its salt
↓
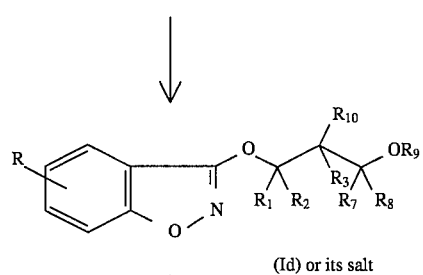
(Id) or its salt
Deprotection ↓
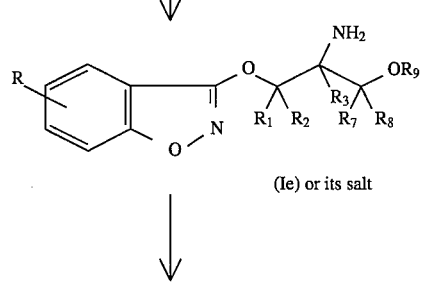
(Ie) or its salt
↓

-continued
Process 1
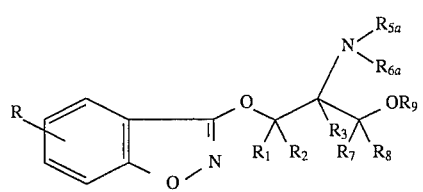
(If) or its salt
Process 3
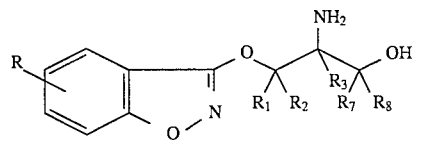
(Ib) or its salt
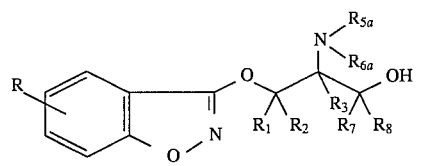
(Ig) or its salt
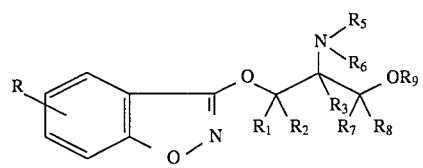
(Ih) or its salt
Process 4
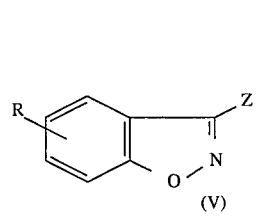
(V)
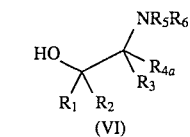
(VI)
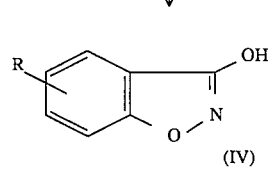
(IV)
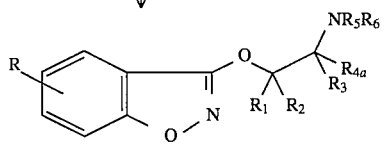
(Ii)

In the above formulas, each of $R$, $R_1$, $R_2$, $R_3$, $R_5$, $R_6$, $R_7$, $R_8$ and $R_9$ has the same meaning as defined above, $R_{4a}$ represents the above-mentioned substituents of $R_4$ other than the lower alkyl groups substituted by lower alkyloxy, lower alkenyloxy, lower alkynyloxy, cycloalkyloxy, aralkyloxy and carbamoyloxy groups; $R_{5a}$ and $R_{6a}$ represent the same groups as $R_5$ and $R_6$, respectively, provided that one of them represents other groups than hydrogen atom; $R_{10}$ represents a protected amino group; Y represents an amino protecting group; and Z represents a removable group.

The protecting group for the protected amino group for $R_{10}$ and the amino protecting group for Y include conventionally used protecting groups, specifically the protecting groups mentioned in Protective Groups in Organic Synthesis, Second Edition [Theodora W. Greene, John Wiley & Sons, Inc.]. Preferable are groups which can be removed with a base or an acid or by a catalytic reduction, which include lower alkyloxycarbonyl groups; aralkyloxycarbonyl groups such as benzyloxycarbonyl group and the like; aralkyl groups; alkylidene groups such as methylidene and ethylidene groups and the like; aralkylidene groups such as benzylidene group and the like; lower acyl groups such as formyl and acetyl groups and the like.

The removable group for Z includes halogen atoms, lower alkanesulfonyloxy groups, arenesulfonyloxy groups and the like.

The salts of the compounds of the general formulas (Ia), (Ib), (Id), (Ie), (If), (Ih) and (Ii) include the same salts as explained as to the salt of the compound of the general formula (I); the salt of the general formula (Ic) includes salts with alkali metals such as sodium, potassium and the like, and further, the salt of the general formula (Ig) includes the same salts as explained as to the salts of the compounds of the general formulas (I) and (Ic).

A further explanation of each production process is made below.

1. Production Process 1

A compound of the general formula (II) or (III) is reacted with an acid in the presence of water and in the presence or absence of a solvent to obtain a compound of the general formula (Ia) or (Ib) or its salt, respectively.

The solvent used in this reaction may be any solvent as far as it does not adversely affect the reaction, and includes, for example, alcohols such as methanol, ethanol, propanol, butanol, ethylene glycol, ethylene glycol monomethyl ether and the like; aromatic hydrocarbons such as benzene, toluene and the like; halogenated hydrocarbons such as methylene chloride, chloroform, 1,2-dichloroethane and the like; ethers such as tetrahydrofuran, dioxane, diethyl ether, 1,2-dimethoxyethane and the like; esters such as ethyl acetate, butyl acetate and the like; aprotic, polar solvents such as acetonitrile, N,N-dimethylformamide, N,N-dimethylacetamide, N-methylpyrrolidone, dimethylsulfoxide, sulfolane, hexamethylphosphoric acid triamide and the like; etc. Also, these solvents may be used alone or in admixture of two or more.

The acid used in this reaction includes inorganic acids and organic acids, for example, mineral acids such as hydrochloric acid, hydrobromic acid, sulfuric acid, phosphoric acid and the like; carboxylic acids such as formic acid, acetic acid, trifluoroacetic acid, trichloroacetic acid and the like; sulfonic acids such as methanesulfonic acid, toluenesulfonic acid, hydroxybenzenesulfonic acid, naphthalenesulfonic acid and the like; Lewis acids such as aluminum chloride, ferric chloride, titanium tetrachloride, boron trifluoride and the like; etc.

In this reaction, the amount of the acid used is 1.0 to 30 moles per mole of the compound of the general formula (II) or (III). Also, this reaction may be carried out at 0°–100° C. for 10 minutes to 24 hours.

(2) A compound of the general formula (Ib) or its salt can be obtained by reacting a compound of the general formula (Ia) with a base in the presence or absence of water and in the presence or absence of a solvent.

The solvent used in this reaction may be any solvent as far as it does not adversely affect the reaction, and includes, for example, alcohols such as methanol, ethanol, propanol, butanol, ethylene glycol, ethylene glycol monomethyl ether and the like; aromatic hydrocarbons such as benzene, toluene and the like; halogenated hydrocarbons such as methylene chloride, chloroform, 1,2-dichloroethane and the like; ethers such as tetrahydrofuran, dioxane, diethyl ether, 1,2-dimethoxyethane and the like; aprotic, polar solvents such as acetonitrile, dimethylsulfoxide, sulfolane and the like; etc. Also, these solvents may be used alone or in admixture of two or more.

Also, the base used in this reaction includes, for example, inorganic bases such as sodium hydroxide, potassium hydroxide, sodium carbonate, potassium carbonate and the like; alcoholates such as sodium methylate, sodium ethylate, potassium tert-butylate and the like; etc.

In this reaction, the amount of the base used is 1.0 to 30 moles per mole of the compound of the general formula (Ia). Also, this reaction may be carried out at 0°–100° C. for 10 minutes to 24 hours.

(3) A compound of the general formula (Ic) or its salt is obtained by reacting a compound of the general formula (III) with an acid in the presence of water in the presence or absence of a solvent.

The solvent and acid used in this reaction include the same as explained in 1 (1) above.

In this reaction, the amount of the acid used is 1.0 to 30 moles per mole of the compound of the general formula (III). Also, this reaction may be carried out at −30° to +100° C. for 10 minutes to 24 hours.

2. Production Processes 2 and 3

(1) A compound of the general formula (Ib) or its salt is reacted with a corresponding acid halide, acid anhydride, aralkyl halide, aldehyde or ketone in the presence or absence of a solvent and either an acid or a base to obtain a compound of the general formula (Ic) or its salt.

The solvent used in this reaction may be any solvent as far as it does not adversely affect the reaction, and includes, for example, alcohols such as methanol, ethanol, propanol, butanol, ethylene glycol, ethylene glycol monomethyl ether and the like; aromatic hydrocarbons such as benzene, toluene and the like; halogenated hydrocarbons such as methylene chloride, chloroform, 1,2-dichloroethane and the like; ethers such as tetrahydrofuran, dioxane, diethyl ether, 1,2-dimethoxyethane and the like; esters such as ethyl acetate, butyl acetate and the like; aprotic, polar solvents such as acetonitrile, N,N-dimethylformamide, N,N-dimethylacetamide, N-methylpyrrolidone, dimethylsulfoxide, sulfolane, hexamethylphosphoric acid triamide and the like; etc., and these solvents may be used alone or in admixture of two or more.

The acid or base which are used as necessary in this reaction includes protonic acids such as hydrochloric acid, acetic acid, methanesulfonic acid, p-toluenesulfonic acid and the like; Lewis acids such as boron trifluoride, titanium tetrachloride and the like; inorganic bases such as sodium hydroxide, potassium hydroxide, sodium carbonate, potassium carbonate and the like; amines such as triethylamine, N-methylmorpholine, N,N-dimethylaniline, diisopropylamine, pyridine, N,N-dimethylaminopyridine, and the like; etc.

The amount of the acid halide, acid anhydride, aralkyl halide, aldehyde or ketone used in this reaction is 1.0–3.0 moles per mole of the compound of the general formula (Ib) or its salt, and the amount of the acid or base used as necessary is 0.1 to 3.0 moles per mole of the compound of the general formula (Ib) or its salt. Also, the reaction temperature and the reaction conditions in this reaction are not particularly limited; however, usually, the reaction may be carried out at −50° to +100° C. for 10 minutes to 24 hours.

(2) (a) A compound of the general formula (Ib), (Ic) or (Ig) or its salt is reacted with a compound represented by the formula $R_9Z$ in which $R_9$ and Z have the same meanings as defined above, in the presence or absence of a solvent to obtain a compound of the general formula (Id) or (Ih) or its salt, respectively.

The solvent used in this reaction may be any solvent as far as it does not adversely affect the reaction, and includes, for example, aromatic hydrocarbons such as benzene, toluene and the like; halogenated hydrocarbons such as methylene chloride, chloroform, 1,2-dichloroethane and the like; ethers such as tetrahydrofuran, dioxane, diethyl ether, 1,2-dimethoxyethane and the like; esters such as ethyl acetate, butyl acetate and the like; aprotic, polar solvents such as acetonitrile, N,N-dimethylformamide, N,N-dimethylacetamide, N-methylpyrrolidone, dimethylsulfoxide, sulfolane, hexamethylphosphoric acid triamide and the like; etc. These solvents may be used alone or in admixture of two or more.

This reaction is preferably effected in the presence of a base, and the base used includes alkali metal alcoholates such as sodium methoxide, sodium ethoxide, potassium tert-butoxide and the like and metal hydrides such as sodium hydride and the like; etc. The amount of the base used is 1.0 to 5.0 moles per mole of the compound of the general formula (Ib), (Ic) or (Ig) or its salt.

The amount of the compound represented by the formula $R_9Z$ used in this reaction is 1.0 to 3.0 moles per mole of the compound of the general formula (Ib), (Ic) or (Ig) or its salt. Also, the reaction temperature and reaction conditions in this reaction are not particularly limited, and the reaction may be carried out usually at 0°–100° C. for 10 minutes to 24 hours.

(b) A compound of the general formula (Id) or (Ih) in which $R_9$ is a substituted or unsubstituted carbamoyl group or its salt is obtained by reacting a compound of the general formula (Ic) or (Ig) or its salt, respectively, with an isocyanate in the presence or absence of a solvent.

The solvent used in this reaction includes the same as explained in 2 (2) (a) above.

The isocyanate used in this reaction may be a usual carbamate reagent, and includes, for example sodium isocyanate; isocyanates substituted by a chlorosulfonyl, trichloroacetyl, trimethylsilyl, lower alkyl, lower alkenyl, lower alkynyl or cycloalkyl group or the like; etc.

The amount of the isocyanate used in this reaction is 1.0–3.0 moles per mole of the compound of the general formula (Ic) or (Ig) or its salt. Also, the reaction temperature and reaction conditions for this reaction are not particularly limited, and the reaction may usually be effected at −50° to +100° C. for 10 minutes to 24 hours.

(c) A compound of the general formula (Ic) or (Ig) or its salt is reacted with phosgene, diphosgene or triphosgene in the presence or absence of a solvent and a base and thereafter with an amine, for example, a lower alkyl hydrazinocarbazinate; an amine substituted by a lower alkyl group, a lower alkenyl group, a lower alkynyl group, a cycloalkyl group or a lower alkyloxy group; or the like in the presence or absence of a solvent and a base to obtain a compound of the general formula (Id) or (Ih) in which $R_9$ is a substituted carbamoyl group or its salt, respectively.

The solvent used in this invention includes the same as explained in 2 (2) (a) above.

The base used as necessary in this reaction includes amines such as triethylamine, N-methylmorpholine, N,N-dimethylaniline, pyridine, N,N-dimethylaminopyridine and the like. The amount of the base used as necessary in this reaction is 1.0–3.0 moles per mole of the compound of the general formula (Ic) or (Ig) or its salt.

The amounts of the phosgene, diphosgene or triphosgene and the amine used in this reaction are 1.0 to 30 moles, respectively, per mole of the compound of the general formula (Ic) or (Ig) or its salt. Also, the reaction temperature and the reaction conditions for this reaction are not particularly limited; however, the reaction may usually be carried out at −50° to +100° C. for 10 minutes to 24 hours.

(d) A compound of the general formula (Id) or (Ih) or its salt in which $R_9$ is a substituted carbamoyl group is obtained by reacting a compound of the general formula (Ic) or (Ig) or its salt, respectively, with a chlorocarbonyl isocyanate in the presence or absence of a solvent, and thereafter reacting with ammonia or a lower alcohol in the presence or absence of a solvent and a base.

The solvent and base used in this reaction include the same solvents and bases as explained in 2 (2) (a) above.

The amounts of the chlorocarbonyl isocyanate and ammonia or lower alcohol used in this reaction are 1.0 to 30 moles, respectively, per mole of the compound of the general formula (Ic) or (Ig) or its salt. Also, the reaction temperature and reaction conditions for this reaction are not particularly limited; however, the reaction may be usually carried out at −50° to +100° C. for 10 minutes to 24 hours.

(3) A compound of the general formula (Ie) or its salt is obtained by reacting a compound of the general formula (Id) or its salt with an acid or a base or subjecting the compound to catalytic reduction, in the presence or absence of water and in the presence or absence of a solvent.

The solvent used in this reaction is the same as in 2 (1) above in the case of the reaction with an acid. Also, in the case of the reaction with a base, the solvent used in the reaction includes, for example, alcohols such as methanol, ethanol, propanol, butanol, isopropyl alcohol, ethylene glycol, ethylene glycol monomethyl ether and the like; aromatic hydrocarbons such as benzene, toluene and the like; halogenated hydrocarbons such as methylene chloride, chloroform, 1,2-dichloroethane and the like; ethers such as tetrahydrofuran, dioxane, diethyl ether, 1,2-dimethoxyethane and the like; aprotic, polar solvents such as acetonitrile, dimethylsulfoxide, sulfolane and the like; etc. These solvents may be used alone or in admixture of two or more. In the case of the catalytic reduction, the solvent used in the reaction includes, for example, alcohols such as methanol, ethanol, propanol, butanol, isopropyl alcohol, ethylene glycol, ethylene glycol monomethyl ether and the like; carboxylic acids such as acetic acid and the like; ethers such as tetrahydrofuran, dioxane, diethyl ether, 1,2-dimethoxyethane and the like; etc., and these solvents may be used alone or in admixture of two or more.

The acid used in this reaction includes inorganic and organic acids, for example, mineral acids such as hydrochloric acid, hydrobromic acid, sulfuric acid, phosphoric acid and the like; carboxylic acids such as formic acid, acetic acid, trifluoroacetic acid, trichloroacetic acid and the like; sulfonic acids such as methanesulfonic acid, toluenesulfonic acid, hydroxybenzenesulfonic acid, naphthalenesulfonic acid and the like; and Lewis acids such as aluminum chloride, ferric chloride, titanium tetrachloride, boron trifluoride and the like. The base includes inorganic bases such as sodium hydroxide, potassium hydroxide, sodium carbonate, potassium carbonate and the like; alkali metal alcoholates such as sodium methoxide, sodium ethoxide, potassium tert-butoxide and the like; etc. Also, the catalyst for the catalytic reduction includes palladium carbon, platinum and the like.

The amount of the acid or base used in this reaction is 0.1 to 30 moles per mole of the compound of the general formula (Id) or its salt, and the amount of the catalyst used in the catalytic reduction is a usual catalytic amount. Also, the reaction temperature and reaction conditions for this reaction are not particularly limited; however, the reaction may usually be carried out at 0°–100° C. for 10 minutes to 24 hours.

(4) A compound of the general formula (If) or (Ig) or its salt is obtained by reacting a compound of the general formula (Ie) or (Ib) or its salt, respectively, with a compound represented by the formula $R_{5a}Z$ or $R_{6a}Z$ in which $R_{5a}$, $R_{6a}$ and Z have the same meanings as mentioned above or with a corresponding acid halide, acid anhydride, aldehyde or ketone in the presence or absence of a solvent and an acid or base, and if necessary, effecting reduction.

The solvent and acid or base used in this reaction include the same as explained in 2 (1) above.

The reducing agent used in this reaction includes diborane, lithium aluminum hydride, sodium borohydride, sodium cyanoborohydride and the like.

The amounts of the compounds represented by the formulas $R_{5a}Z$ and $R_{6a}Z$, acid halide, acid anhydride, aldehyde or ketone used in this reaction or the reducing agent optionally used are 1.0–3.0 moles, respectively, per mole of the compound of the general formula (Ie) or (Ib) or its salt, and the amount of the acid or base used is 0.1 to 3.0 moles per mole of the compound of the general formula (Ie) or (Ib) or its salt. Also, the reaction temperature and the reaction conditions for this reaction are not particularly limited; however, the reaction may be usually carried out at −50° to +100° C. for 10 minutes to 24 hours.

3. Production Process 4

(1) A compound of the general formula (Ii) is obtained by reacting a compound of the general formula (V) with a salt of a compound of the general formula (VI) with an alkali metal such as sodium, potassium or the like in the presence or absence of a solvent.

The solvent used in this reaction includes the same as explained in 2 (2) (a) above.

The amount of the alkali metal salt of the compound of the general formula (VI) used in this reaction is 1.0 to 3.0 moles per mole of the compound of the general formula (V). Also, the reaction temperature and the reaction conditions for this reaction are not particularly limited; however, the reaction may be usually carried out at 0°–150° C. for 10 minutes to 24 hours.

(2) A compound of the general formula (Ii) or its salt is obtained by subjecting a compound of the general formula (IV) to Mitsunobu reaction with a compound of the general formula (VI) in the presence of a solvent, an azodicarboxylic acid ester and an organic phosphorus compound.

The azodicarboxylic acid ester used in this reaction includes $C_{1-6}$ alkyl, aryl and aralkyl azodicarboxylates, and the like.

The organic phosphorus compound used in this reaction includes tri-$C_{1-6}$ alkylphosphines, triarylphosphines, triaralkylphosphines and the like.

The solvent used in this reaction includes the same as mentioned in 2 (2) (a) above.

The amount of the compound of the general formula (VI) used in this reaction is 1.0 to 3.0 moles per mole of the compound of the general formula (IV), and the amounts of the azodicarboxylic acid ester and organic phosphorus compound used are respectively 1.0 to 3.0 moles per mole of the compound of the general formula (IV). Also, the reaction temperature and the reaction conditions for this reaction are not particularly limited; however, the reaction may be usually carried out at 0°–100° C. for 10 minutes to 24 hours.

Also, the 1,2-benzoisoxazole derivative of the general formula (I) or its salt can be converted into other 1,2-benzoisoxazole derivatives of the general formula (I) or their salts by combining reactions known per se such as substitution reaction, addition reaction, elimination reaction, reduction reaction, oxidation reaction, dehydration reaction, hydrolysis reaction and the like.

The compounds of the general formula (II) and the general formula (III) or their salts which are the starting materials for producing the compound of this invention can be produced in a manner known per se, for example, by the processes shown below.

Process 1

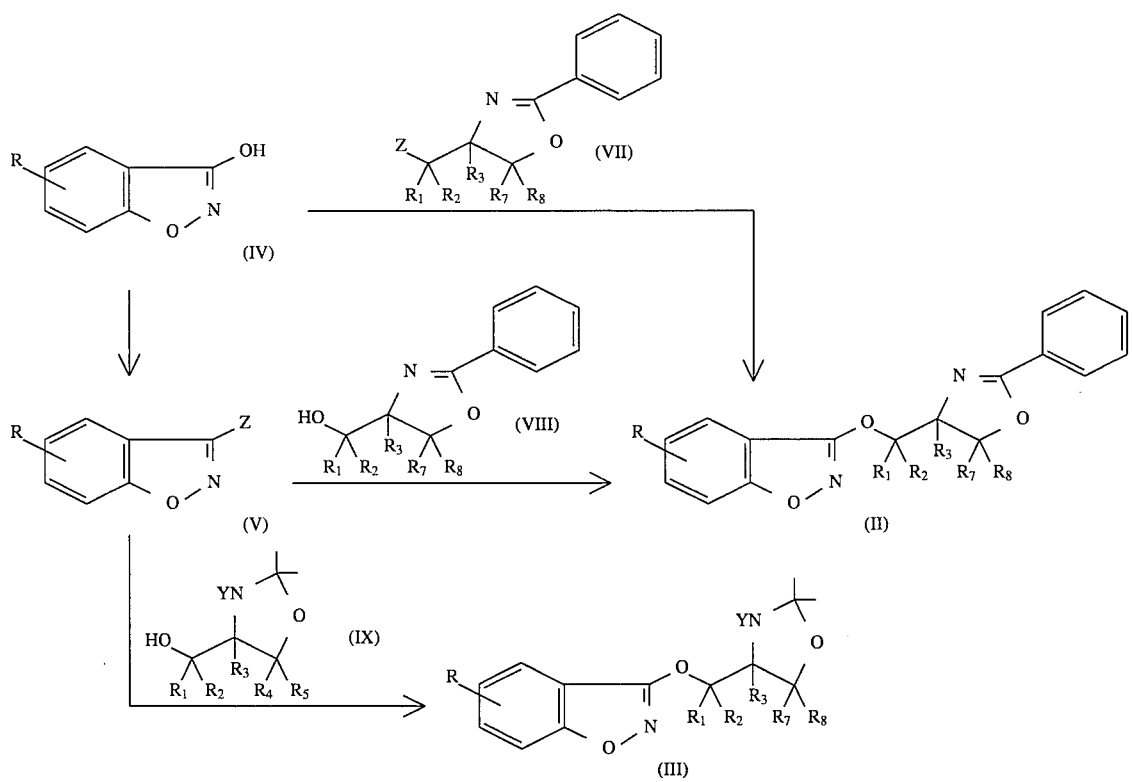

In the above formulas, each of R, $R_1$, $R_2$, $R_3$, $R_4$, $R_5$, $R_7$, $R_8$, Y and Z has the same meaning as defined above.

Compounds of the general formulas (IV) and (V) can be produced by the process disclosed in, for example, Chem. Ber., Vol. 100, pages 954–960 and 3326–3330 (1967) and the like or in a manner known per se.

A compound of the general formula (VIII) can be produced by the process disclosed in, for example, J. Org. Chem., Vol. 48, pages 1197–1202 (1983) or in a manner known per se.

A compound of the general formula (VII) can be obtained by reacting, for example, a compound of the general formula (VIII) with a halogenating agent or a sulfonating agent.

A compound of the general formula (II) can be obtained by reacting a compound of the general formula (V) with a salt of a compound of the general formula (VIII) with a metal such as sodium, potassium or the like or reacting a salt of a compound of the general formula (IV) with a metal such as sodium, potassium or the like with a compound of the general formula (VII).

A compound of the general formula (IX) can be produced by the process disclosed in, for example, J. Org. Chem., Vol. 52, pages 2361–2364 (1987) or in a manner known per se.

A compound of the general formula (III) can be obtained by reacting a compound of the general formula (V) with a salt of a compound of the general formula (IX) with a metal such as sodium, potassium or the like.

Also, a compound of the general formula (VI) or its salt can be produced from, for example, a compound represented by the general formula:

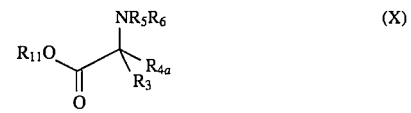

wherein each of $R_3$, $R_{4a}$, $R_5$ and $R_6$ has the same meaning as defined above, and $R_{11}$ represents a hydrogen atom or a lower alkyl group, or its salt according to the process disclosed in, for example, Tetrahedron Letters, Vol. 33, pages 5517–5518 (1992); Chem. Pharm. Bull., Vol. 30, pages 1921–1924 (1982); and the like or in a manner known per se.

In the above-mentioned processes for producing the compound of this invention and the above-mentioned processes for producing the starting compounds, when the compounds of the general formulas (II), (III), (IV), (V), (VI), (VII), (VIII), (IX) and (X) and their salts have isomers (for example, optical isomers, geometrical isomers, tautomers and the like), these isomers can be used.

In the above-mentioned processes for producing the compound of this invention and the above-mentioned processes for producing the starting compounds, when the compounds have an active group such as amino group, hydroxyl group or the like at other sites than the reactive sites, such an active group may be previously protected in a conventional manner and deprotected after the reaction in a conventional manner.

Also, after completion of the reaction, the reaction mixture can be, as it is, used without isolation in the subsequent reaction.

Also, the objective compound of the reaction can be isolated and purified in a usual manner such as extraction, crystallization, column chromatography or the like.

Next, pharmacological activities of representative compounds of this invention (Tables A to E) are explained.

Incidentally, R and A in Tables A to E represent the corresponding substituents of a compound represented by the following formula:

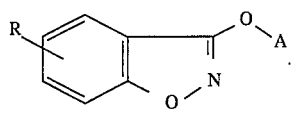

Also, the abbreviations used in Tables A to E have the following meanings:

Ph: phenyl group n-Bu: n-butyl group

Moreover, the test compounds used in the following tests are in the form of hydrochloride. Also, the test compound Nos. used in the following tests indicate Nos. of Examples.

TABLE A

| No. | R | A |
|---|---|---|
| 39 | 5, Cl | NH$_2$, OCH$_3$ |
| 40 | 5, Cl | NH$_2$, OCH$_3$ |
| 41 | 5, Cl | NH$_2$, OCH$_3$ |
| 42 | 5, $-$OCH$_2$Ph | NH$_2$, OCH$_3$ |
| 47 | 5, Cl | NH$_2$, OCONH$_2$ |
| 48 | 5, Cl | NH$_2$, OCONH$_2$ |
| 49 | 5, Cl | NH$_2$, OCONH$_2$ |

TABLE B

| No. | R | A |
|---|---|---|
| 50 | 5, Cl | NH$_2$, OCONH$_2$, CH$_3$ |
| 51 | 5, Cl | NH$_2$, OCONH$_2$, CH$_3$ |
| 53 | 5, CH=CH$_2$ | NH$_2$, OCONH$_2$ |
| 56 | 5, n-Bu | NH$_2$, OCONH$_2$ |
| 57 | 5, Ph | NH$_2$, OCONH$_2$ |

TABLE B-continued

| No. | R | A |
|---|---|---|
| 58 | 5, Cl 7, Cl | NH$_2$, OCONH$_2$ |
| 59 | 6, Cl | NH$_2$, OCONH$_2$ |

TABLE C

| No. | R | A |
|---|---|---|
| 67 | 5, I | NH$_2$, OCONH$_2$ |
| 73 | 5, Br | NH$_2$, OCONH$_2$ |
| 74 | H | NH$_2$, OCONH$_2$ |
| 86 | 5, Cl | NH$_2$, OCONHCH$_2$CH$_3$ |

TABLE D

| No. | R | A |
|---|---|---|
| 100 | 5, Cl | NH$_2$, thiazole-CH$_3$ |
| 101 | 5, Cl | NH$_2$, cyclopropyl |
| 105 | 5, Cl | NH$_2$, C$_6$H$_4$-OCH$_3$ |

TABLE E

| No. | R | A |
|---|---|---|
| 117 | 5, Cl | NH$_2$ |
| 118 | 5, Cl | NH$_2$ |
| 119 | 5, Cl | NH$_2$ |

TABLE E-continued

| No. | R | A |
|---|---|---|
| 127 | 5, Cl | NH₂ group with SCH₃ chain |
| 133 | 5, Cl | NH₂ group with alkyl chain |
| 138 | 5, Cl | NH₂ group with SCH₃ chain |
| 140 | 5, Cl | NH₂ group with O-SCH₃ chain |
| 141 | 5, Cl | NH₂ group with O₂-SCH₃ chain |

1. [Cerebral hypoxia-protecting action]

The test method was in accordance with the method stated in Arch. Int. Pharmacodyn., Vol. 139, pages 67–74 (1962). Namely, to a group consisting of eight male ICR mice (4 weeks old) was orally administered 10 mg/kg, 30 mg/kg or 100 mg/kg of a test compound dissolved in distilled water or suspended in a 0.5% (w/v) methyl cellulose solution, and after one hour, the mice were placed in a glass chamber, through which a mixed gas consisting of 4% of oxygen and 96% of nitrogen was passed and the time taken until the mice died was measured. The effect of prolongation of life was calculated assuming as 100 the time taken until the mice to which only distilled water or a 0.5% (w/v) methyl cellulose solution was orally administered died. The results are shown in Table 1.

TABLE 1

| Test compound | Effect of prolongation of life |
|---|---|
| 39 | 190 |
| 40 | 185 |
| 41 | 209 |
| 42 | 178 |
| 47 | 182 |
| 48 | 183 |
| 49 | 202 |
| 51 | 195 |
| 53 | 174 |
| 67 | 172 |
| 73 | 170 |
| 100 | 159** |
| 101 | 171* |
| 105 | 201** |
| 117 | 195 |
| 118 | 223 |
| 119 | 189 |
| 127 | 162* |
| 133 | 175 |
| 138 | 211* |
| 140 | 184* |
| 141 | 186* |

Note:
*value when administered at 30 mg/kg.
**value when administered at 100 mg/kg.

2. [Effect on the survival time of cerebral ischemia in mice]

The test method was in accordance with the method stated in "Folia Pharmacologica Japonica", Vol. 87, pages 427–434 (1986). Namely, the common carotid artery on one side of each mouse of a group consisting of 10–15 male ICR mice (8–9 weeks old) was ligated. Next day, a test compound dissolved in distilled water or suspended in a 0.5% (w/v) methyl cellulose solution was orally administered, and after one hour, the common carotid artery on the other side was ligated to make the brain ischemic. And, the time taken until the mouse caused convulsion due to cerebral ischemia to die was measured. The effect of prolongation of life was calculated assuming as 100 the time taken until the mouse to which only distilled water or a 0.5% (w/v) methyl cellulose solution was orally administered died. The results are shown in Table 2.

TABLE 2

| Test compound | Dose (mg/kg) | Survival time (%) |
|---|---|---|
| 39 | 30 | 163 |
| 47 | 100 | 174 |

3. [Ameliorating effect on the neurological symptoms on middle cerebral artery temporary ischemia in rats]

The test method was in accordance with the method disclosed in Jpn. J. Stroke, Vol. 8, pages 1–8 (1986). Namely, each rat of a group consisting of 10–13 male STD Wistar ST rats (7–8 weeks old) was operated under ether anesthesia to expose the bifuracated region of right common carotid artery and ligate the common carotid artery and external carotid artery. The ligated common carotid artery was dissected and a nylon-coated embolus was inserted about 18 mm from the same site toward the internal carotid artery to occlude from the end of the internal carotid artery to the introitus of the middle cerebral artery. After the occlusion, 30 mg/kg of a test compound dissolved in physiological saline was immediately administered intraperitoneally, one hour after which the embolus was drawn out to recirculate the blood flow through the anterior, comminicating artery and posterior comminicating artery. Ameliorating effects on the neurological symptoms was evaluated as a depressing degree of neurological symptoms obtained according to the following equation from the total of the symptom scores measured based on the following tests a to f after 48 hours from the recirculation. The results are shown in Table 3.

Neurological Symptom Score a. Posture test 1: Tail is lifted to hang.
   2: Rat immediately twists to the left side.
   1: Rat twists after a while or weakly twists.
   0: Rat does not twist or twists to left and right similarly.
b. Lateral turning: Left and right sides are pushed.
   2: When the right side is pushed rat falls down.
   1: When the right side is pushed rat totters to the left side.
   0: When either right or left side is pushed rat does not totter.
c. Hemiplegia test: Body is held and hind limbs are on floor.
   1: Right hind limbs is splayed out.
   0: Bilaterally symmetrical.
d.: Hind limbs hemiplegia test: The instep of left hind limb of rat is lifted with pen.
   2: When hind limb is stretched to behind rat does not resist at all and is as stretched.
   1: Rat escapes sometimes or slowly.
   0: Rat escapes immediately.
e: Posture test 2: Rat is taken by the neck and lifted.
   2: Head is greatly turned to left of body.

1: Head is small turned to left of body.

0: Laterally symmetrical.

f. Forepaw hemiplegia test: Rat is taken by the right forepaw and lifted.

1: Left forepaw is attached to breast.

0: Left forepaw is not attached to breast.

The scores of each of the above tests are totaled.

Method of calculation of depressing degree of neurological symptoms.

Depressing degree of neurological symptoms (%) =

$$\frac{\text{(Score of control group)} - \text{(Score of test group)}}{\text{(Score of control group)}} \times 100$$

* Control group: Middle cerebral artery temporary ischemia rats that are not administered test compounds.

TABLE 3

| Test compound | Depressing degree of neurological symptoms (%) |
|---|---|
| 47 | 46.3 |
| 74 | 49.2 |
| 119 | 50.9 |
| 138 | 35.4 |

4. [Anticonvulsive action]

The test method was in accordance with the method disclosed in Arch. Int. Pharmacodyn., Vol. 156, pages 261–270 (1965). Namely, to a group consisting of 5 male ICR mice (4 weeks old) is administered intraperitoneally 0.3 mg/kg of a test compound dissolved in physiological saline or suspended in a 0.5% (v/w) methyl cellulose-physiological saline solution and, after 30 minutes, 170 mg/kg of pentetrazole is intraperitoneally administered. And, the time taken until tonic convulsion appeared in mice was measured. The anticonvulsive effect was calculated assuming as 100 the time taken until convulsion appeared in mice to which only physiological saline or 0.5% methyl cellulose-physiological saline was administered. The results are shown in Table 4.

TABLE 4

| Test compound | Appearance time (%) |
|---|---|
| 41 | 319 |
| 50 | 287 |
| 51 | 258 |
| 56 | 249 |
| 57 | 341 |
| 58 | 276 |
| 59 | 274 |
| 74 | 223 |
| 86 | 346 |

4. [Dyskinetic action]

The test method was in accordance with the method state in Pharmacometrics, Vol. 43, pages 173–194 (1992). That is to say, to a group consisting of 3–4 male ICR mice (4 weeks old) was orally administered 100 mg/kg of a test compound dissolved in distilled water or suspended in a 0.5% (w/v) methyl cellulose solution, and, after 30 minutes, the mouse was allowed to hang from a piece of wire of 1.6 mm in diameter, and the time taken until the mouse fell was measured. The case where the mouse did not fall for 10 seconds was judged as no dyskinetic action. As a result, the Nos. 47, 53, 59, 67, 73, 74, 100, 101, 127, 138, 140 and 141 compounds did not exhibit dyskinetic action.

When the compound of this invention is used as a drug, pharmaceutically usable additives such as excipients, carriers, diluents and the like may be appropriately mixed, and these can be administered orally or parenterally in the form of an injection, tablet, capsule, suppository, powder or the like. The dose is usually about 1–1,000 mg per day per adult in the case of parenteral administration, and this amount is administered at one time or in portions; however, the dose can be adequately selected depending upon the age, weight and symptomatology of a patient.

BEST MODE FOR CARRYING OUT THE INVENTION

In order to explain this invention in more detail, Reference Examples and Examples are mentioned; however, this invention is not limited thereto. Incidentally, the mixing ratios in mixed solvents and eluants are all by volume and as the carriers used in column chromatography, silica gel [silica gel 60, No. 7734] manufactured by MERCK & CO. INC. was used. Also, the abbreviations used hereinafter have the following meanings:

Tr: Trityl group

Boc: tert-Butoxycarbonyl group

Et: Ethyl group n-Bu: n-Butyl group

Ph: Phenyl group

Moreover, the numerals put before each group of R in the Tables indicate the substitution positions.

REFERENCE EXAMPLE 1

To a suspension of 2.44 g of 5-fluorosalicylhydroxamic acid in 22 ml of tetrahydrofuran is added 1.83 g of thionyl chloride at 10° C., and they are subjected to reaction at 20°–25° C. for one hour. Subsequently, at 10°–15° C., 4.67 g of triethylamine is dropped over 30 minutes, and thereafter, reaction is effected at 20°–25° C. for one hour. To the reaction mixture is added 200 ml of water, and the pH is adjusted to 3 with 2N hydrochloric acid. The crystals precipitated are collected by filtration to obtain 1.32 g of colorless, crystalline 5-fluoro-3-hydroxy-1,2-benzoisoxazole having a melting point of 201°–203° C.

IR (KBr) cm$^{-1}$: 1624, 1570, 1541, 1454, 1306, 1259, 1197

REFERENCE EXAMPLES 2 TO 14

In the same manner as in Reference Example 1, the compounds shown in Table 5a and Table 5b are obtained. Incidentally, R in Table 5a and Table 5b indicates the substituent of a compound represented by the following formula:

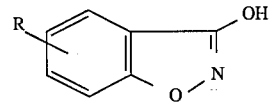

TABLE 5a

| No. | R |
|---|---|
| 2 | 5, Ph |
| 3 | 5, n-Bu |
| 4 | 5, —NHCOPh |
| 5 | 5, —O-n-Bu |
| 6 | 5, —N⟨ (pyrrolidinyl) |

TABLE 5a-continued

| No. | R |
|---|---|
| 7 | 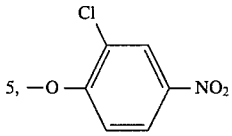 5, —O— (Cl, NO₂ substituted phenyl) |
| 8 | 5, —COPh |

TABLE 5b

| No. | R |
|---|---|
| 9 | 5, —CH=CH₂ |
| 10 | 5, —CN |
| 11 | 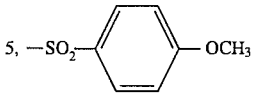 5, —SO₂— (OCH₃ substituted phenyl) |
| 12 | 5, —CF₃ |
| 13 | 5, —OCH₂Ph |
| 14 | 5, —NHBoc |

Physical properties of the compounds shown in Tables 5a and 5b are shown below.

No. 2: IR (KBr) cm⁻¹: 3004, 1609, 1558, 1526, 1298, 949, 826, 755, 699 Melting point: 181°–183° C.

No. 3: IR (KBr) cm⁻¹: 2951, 1612, 1561, 1532, 1317, 1241, 957, 901, 827, 804, 766 Melting point: 78°–80° C.

No. 4: IR (KBr) cm⁻¹: 3291, 3057, 1638, 1558, 1490 Melting point: 224°–226° C.

No. 5: IR (KBr) cm⁻¹: 2958, 2871, 1613, 1560, 1528, 1455, 1212 Melting point: 107°–109° C.

No. 6: IR (KBr) cm⁻¹: 3128, 3030, 2955, 1567, 1530, 1508, 1494, 729 Melting point: 163°–165° C.

No. 7: IR (KBr) cm⁻¹: 3104, 2997, 2932, 1568, 1515, 1345, 1270 Melting point: 198°–202° C.

No. 8: IR (KBr) cm⁻¹: 3062, 3019, 2921, 1662, 1622, 1563, 1318, 1285, 1259 Melting point: 187°–189° C.

No. 9: IR (KBr) cm⁻¹: 1605, 1558, 1521, 1312, 1247, 991, 890, 818, 766 Melting point: 185° C. (decomp.)

No. 10: IR (KBr) cm⁻¹: 3103, 3019, 2942, 2234, 1628, 1606, 1569 Melting point: 262°–264° C.

No. 11: IR (KBr) cm⁻¹: 2984, 2586, 1610, 1593, 1496, 1324, 1263, 1165, 1138, 1087, 1025, 840, 803, 694, 579 Melting point: 241°–245° C.

No. 12: IR (KBr) cm⁻¹: 3077, 2953, 1634, 1616, 1568, 1324, 1294, 1170, 1134 Melting point: 144°–146° C.

No. 13: IR (KBr) cm⁻¹: 1568, 1526, 1456, 1304, 1220 Melting point: 163°–165° C.

No. 14: IR (KBr) cm⁻¹: 3341, 2987, 1692 1619, 1566, 1514, 1241, 1164 Melting point: 171°–172° C.

REFERENCE EXAMPLE 15

A solution of 5.32 g of 4-hydroxymethyl-2-phenyl-4,5-dihydroxazole is added at 20°–25° C. to a suspension of 1.56 g of 60% (w/w) sodium hydride in 28 ml of tetrahydrofuran and they are refluxed for two hours. Subsequently, under reflux, a solution of 5.64 g of 3,5-dichloro-1,2-benzoisoxazole in 28 ml of tetrahydrofuran is added and they are further refluxed for one hour. The reaction mixture is cooled and thereafter the solvent is removed by distillation under reduced pressure, after which ethyl acetate and water are added to the residue obtained. After shaking, the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane-:ethyl acetate=3:1] to obtain 9.17 g of colorless, crystalline 5-chloro-3-[(2-phenyl-4,5-dihydroxazol-4-yl)methoxy]-1,2-benzoisoxazole having a melting point of 88°–90° C.

IR (KBr) cm⁻¹: 2911, 1652, 1547, 1478, 1362, 1257, 1062, 922, 807, 693, 552

REFERENCE EXAMPLES 16 TO 17

In the same manner as in Reference Example 15, the compounds shown in Table 6 are obtained. Incidentally, R, R₁ and R₂ represent the corresponding substituents of a compound represented by the following formula:

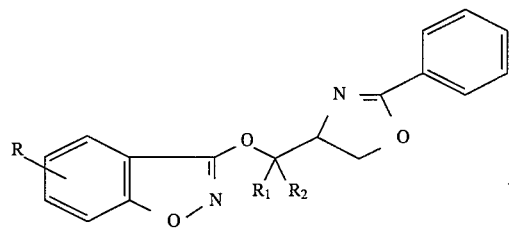

TABLE 6

| No. | R | R₁ | R₂ |
|---|---|---|---|
| 16 | 5, 6, —CH=CH—CH=CH— | H | H |
| 17 | 5, Cl | CH₃ | CH₃ |

Physical properties of the compounds shown in Table 6 are shown below:

No. 16: IR (KBr) cm⁻¹: 1647, 1543, 1474, 1376, 1245, 1211, 743, 694 Solid product No. 17: IR (neat) cm⁻¹: 1648, 1528, 1460, 1376, 695 Oily product

REFERENCE EXAMPLE 18

To a suspension of 0.28 g of 60% (w/w) sodium hydride in 9 ml of N,N-dimethylformamide is added 0.92 g of 5-fluoro-3-hydroxy-1,2-benzoisoxazole at 10°–15° C. and they are subjected to reaction at the same temperature for 30 minutes. This reaction mixture is added to a solution of 1.53 g of 4-methanesulfonyloxymethyl-2-phenyl-4,5-dihydroxazole in 11 ml of N,N-dimethylformamide at 80°–90° C., and they are subjected to reaction at the same temperature for two hours. Ethyl acetate and water are added to the reaction mixture and, after shaking, the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane-:ethyl acetate=2:1] to obtain 1.46 g of colorless, crystalline 5-fluoro-3-[(2-phenyl-4,5-dihydroxazol-4-yl)methoxy]-1,2-benzoisoxazole having a melting point of 98°–99° C.

IR (KBr) cm⁻¹: 1652, 1549, 1496, 1449, 1364, 1354

REFERENCE EXAMPLES 19 TO 36

In the same manner as in Reference Example 18, the compounds shown in Table 7a to Table 7c are obtained.

Incidentally, R in Table 7a to Table 7c represents the substituent of a compound represented by the following formula:

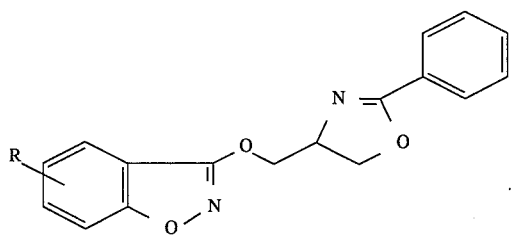

TABLE 7a

| No. | R |
|---|---|
| 19 | 5, —NHCOPh |
| 20 | 5, —O-n-Bu |
| 21 | 5, Br |
| 22 | 5, Et |
| 23 | 5, —N⟨pyrrolidinyl⟩ |
| 24 | 5, —CH=CH$_2$ |
| 25 | 5, —COPh |

TABLE 7b

| No. | R |
|---|---|
| 26 | 5, —SCH$_3$ |
| 27 | 5, —SO$_2$—C$_6$H$_4$—OCH$_3$ |
| 28 | 5, —CF$_3$ |
| 29 | 5, —CN |
| 30 | 5, —O—(3-Cl,4-NO$_2$-C$_6$H$_3$) |
| 31 | 5, —NHBoc |
| 32 | 5, —NO$_2$ |

TABLE 7c

| No. | R |
|---|---|
| 33 | 5, —OCH$_2$Ph |
| 34 | 5, I |
| 35 | 6, —OCH$_3$ |
| 36 | 7, Cl |

Physical properties of the compounds shown in Table 7a to Table 7c are shown below.

No. 19: IR (KBr) cm$^{-1}$: 3275, 1646, 1541, 1488 Melting point: 197°–199° C.

No. 20: IR (KBr) cm$^{-1}$: 2962, 2933, 1651, 1539, 1496 Melting point: 94°–96° C.

No. 21: IR (KBr) cm$^{-1}$: 1652, 1609, 1547, 1472, 1440, 1364, 1349, 1302 Melting point: 107°–108° C.

No. 22: IR (neat) cm$^{-1}$: 1649, 1538, 1495, 1451, 1366 Oily product

No. 23: IR (KBr) cm$^{-1}$: 1651, 1544, 1503, 719, 692 Melting point: 139°–140° C.

No. 24: IR (neat) cm$^{-1}$: 1646, 1539, 1489, 1451, 1367, 1325, 1245 Oily product No. 25: IR (neat) cm$^{-1}$: 1658, 1651, 1617, 1540, 1261, 696 Oily product No. 26: IR (KBr) cm$^{-1}$: 1651, 1605, 1539, 1472 Melting point: 116°–117° C.

No. 27: IR (KBr) cm$^{-1}$: 3094, 2962, 1638, 1594, 1370, 1334, 1265, 1144, 697, 581 Melting point: 159°–161° C.

No. 28: IR (KBr) cm$^{-1}$: 1649, 1631, 1549, 1321, 1179, 1105 Melting point: 101°–103° C.

No. 29: IR (KBr) cm$^{-1}$: 2232, 1650, 1541 Melting point: 140°–141° C.

No. 30: IR (KBr) cm$^{-1}$: 1647, 1539, 1522, 1476, 1346, 1266, 696 Solid product No. 31: IR (KBr) cm$^{-1}$: 3336, 1687, 1645, 1543, 1496, 1366, 1330, 1285, 1244, 1162 Melting point: 137°–140° C.

No. 32: IR (KBr) cm$^{-1}$: 1642, 1621, 1549, 1532, 1485, 1474, 1372, 1340, 1290, 1262 Melting point: 146°–147° C.

No. 33: IR (KBr) cm$^{-1}$: 1653, 1542, 1494, 1448, 1363, 1334, 1266, 1220 Melting point: 134°–135° C.

No. 34: IR (KBr) cm$^{-1}$: 1646, 1538, 1469, 1362, 550 Solid product

No. 35: IR (KBr) cm$^{-1}$: 1645, 1623, 1532, 1444, 1429, 1162, 1151, 1024, 696 Melting point: 88°–90° C.

No. 36: IR (KBr) cm$^{-1}$: 1645, 1550, 1426, 1382, 1367, 972, 746, 691 Melting point: 99°–100° C.

REFERENCE EXAMPLE 37

A solution of 6.94 g of 3-tert-butoxycarbonyl-4-hydroxymethyl-2,2-dimethyloxazolidine in 28 ml of tetrahydrofuran is added to a solution of 6.02 g of potassium tert-butoxide in 28 ml of tetrahydrofuran at 10°–15° C., and they are subjected to reaction at the same temperature for two hours. Subsequently, this reaction mixture is added under reflux to a solution of 5.64 g of 3,5-dichloro-1,2-benzoisoxazole in 28 ml of tetrahydrofuran and they are refluxed for a further one hour. The reaction mixture is cooled and thereafter the solvent is removed by distillation under reduced pressure, after which ethyl acetate and water are added to the residue obtained, and after shaking, the organic layer is separated. The separated organic layer is washed with a saturated saline solution and dried over anhydrous magnesium sulfate, after which the solvent is removed by distillation under reduced pressure. The crystals obtained are recrystallized from n-hexane to obtain 8.41 g of colorless, crystalline 3-[(3-tert-butoxycarbonyl-2,2-dimethyloxazolidin-4-yl)methoxy]-5-chloro-1,2-benzoisoxazole having a melting point of 117°– 118° C.

IR (KBr)cm$^{-1}$: 2981, 1538, 1462, 1393, 1368, 1177, 830

REFERENCE EXAMPLES 38 TO 48

In the same manner as in Reference Example 37, the compounds shown in Table 8a and Table 8b are obtained. Incidentally, R, R$_7$ and R$_8$ in Table 8a and Table 8b represent the corresponding substituents of a compound represented by the following formula:

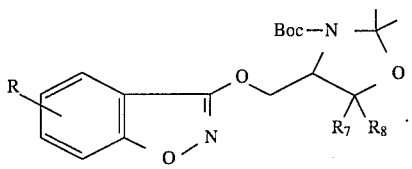

TABLE 8a

| No. | R | R₇ | R₈ |
|---|---|---|---|
| 38*¹ | 5, Cl | H | H |
| 39*² | 5, Cl | H | H |
| 40*³ | 5, Cl | CH₃ | H |
| 41*⁴ | 5, Cl | H | CH₃ |
| 42 | 5, CH₃ | H | H |
| 43 | 5, —OCH₃ | H | H |
| 44 | 5, Ph | H | H |

*¹: The 4-position of the oxazoline ring: (S) configuration
*²: The 4-position of the oxazoline ring: (R) configuration
*³: The 4-position and 5-position of the oxazoline ring: both (R) configuration
*⁴: The 4-position and 5-position of the oxazoline ring: both (S) configuration TABLE 8b

| No. | R | R₇ | R₈ |
|---|---|---|---|
| 45 | 5, n-Bu | H | H |
| 46 | H | H | H |
| 47 | 6, Cl | H | H |
| 48 | 5, Cl 7, Cl | H | H |

Physical properties of the compounds shown in Table 8a and Table 8b are shown below.

No. 38: IR (KBr) cm⁻¹: 3482, 2980, 1700, 1610, 1541, 1477, 1389, 1259, 1173, 1088, 808 Melting point: 80°–81° C.

No. 39: Melting point: 79°–80° C.

No. 40: IR (neat) cm⁻¹: 1695, 1541, 1477, 1387, 1367 Oily product

No. 41: Oily product

No. 42: IR (neat) cm⁻¹: 2979, 1698, 1611, 1539, 1496, 1386 Oily product

No. 43: IR (neat) cm⁻¹: 2980, 1697, 1612, 1538, 1498, 1391 Oily product

No. 44: IR (KBr) cm⁻¹: 1690, 1547, 1481, 1393, 1375, 1365 Melting point: 142°–143° C.

No. 45: IR (neat) cm⁻¹: 1704, 1540, 1495, 1386, 1366 Oily product

No. 46: IR (KBr) cm⁻¹: 1685, 1555, 1490, 1260, 1130, 720 Solid product

No. 47: IR (neat) cm⁻¹: 1698, 1613, 1538, 1429, 1386 Oily product

No. 48: IR (neat) cm⁻¹: 1700, 1541, 1477, 1388, 1365 Oily product

REFERENCE EXAMPLE 49

A solution of 3.00 g of 4-methoxycarbonyl-2-phenyl-4,5-dihydroxazole in 6 ml of diethyl ether is added at 25°–30° C. to a solution in 12 ml of diethyl ether of a Grignard reagent obtained from 0.85 g of magnesium and 4.97 g of methyl iodide, and they are subjected to reaction at the same temperature for ten minutes. The reaction mixture is poured into water and after stirring, the organic layer is separated. The separated organic layer is washed with a saturated saline solution and dried over anhydrous magnesium sulfate, after which the solvent is removed by distillation under reduced pressure. The residue obtained is purified by a column chromatography [eluant:toluene:ethyl acetate=3:1] to obtain 2.78 g of colorless, oily 1-methyl-1-(2-phenyl-4,5-dihydroxazol-4-yl)ethanol.

IR (neat) cm⁻¹: 3406, 2974, 1650, 1360, 1089, 966, 694

EXAMPLE 1

(1) To a solution of 9.86 g of 5-chloro-3-[(2-phenyl-4,5-dihydroxazol-4-yl)methoxy]-1,2-benzoisoxazole in 99 ml of tetrahydrofuran is added 20 ml of 3N hydrochloric acid at 20°–25° C., and they are subjected to reaction at the same temperature for one hour. The crystals precipitated are collected by filtration, to obtain 9.57 g of colorless, crystalline 3-(2-amino-3-benzoyloxypropoxy)-5-chloro-1,2-benzoisoxazole hydrochloride having a melting point of 204°–206° C.

(2) To a solution of 4.00 g of sodium hydroxide in 77 ml of methanol is added 7.66 g of 3-(2-amino-3-benzoyloxypropoxy)-5-chloro-1,2-benzoisoxazole hydrochloride at 20°–25° C., and they are subjected to reaction at the same temperature for ten minutes. The solvent is removed from the reaction mixture by distillation under reduced pressure, and ethyl acetate and water are added to the residue obtained, and after shaking, the organic layer is separated. The separated organic layer is washed with a saturated saline solution and dried over anhydrous magnesium sulfate, after which the solvent is removed by distillation under reduced pressure to obtain 4.13 g of colorless, crystalline 3-(2-amino-3-hydroxypropoxy)-5-chloro-1,2-benzoisoxazole.

EXAMPLES 2 TO 14

In the same manner as in Example 1, the compounds shown in Table 9a and Table 9b are obtained. Incidentally, R, R₃, R₇ and R₈ in Table 9a and Table 9b represent the corresponding substituents of a compound represented by the following formula:

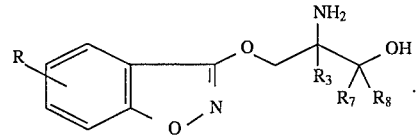

TABLE 9a

| No. | R | R₃ | R₇ | R₈ |
|---|---|---|---|---|
| 2 | 5, 6 —CH=CH—CH=CH— | H | H | H |
| 3 | 5, —NHCOPh | H | H | H |
| 4 | 5, I | H | H | H |
| 5 | 6, —OCH₃ | H | H | H |
| 6 | 5, —O-n-Bu | H | H | H |
| 7* | 5, Cl | CH₃ | H | H |
| 8 | 5, Et | H | H | H |

*Obtained by hydrolysis, with an acid, 5-chloro-3-[(4-aza-3-methyl-1-oxaspiro[4,5]-decan-3-yl)methoxy]-1,2-benzoisoxazole obtained from 3,5-dichloro-1,2-benzoisoxazole and 4-aza-3-hydroxymethyl-3-methyl-1-oxaspiro[4,5]decane in the same manner as in Reference Example 15.

TABLE 9b

| No. | R | $R_3$ | $R_7$ | $R_8$ |
|---|---|---|---|---|
| 9 | 5, —CH=CH$_2$ | H | H | H |
| 10 | 5, —NO$_2$ | H | H | H |
| 11 | 5, Br | H | H | H |
| 12 | 5, —N(pyrrolyl) | H | H | H |
| 13 | 5, —O—(2-chloro-4-nitrophenyl) | H | H | H |
| 14 | 5, —COPh | H | H | H |

Physical properties of the compounds shown in Table 9a and Table 9b are shown below.

No. 2: IR (KBr) cm$^{-1}$: 3335, 3286, 3182, 2888, 2855, 1615, 1547, 1503 Solid product No. 3: IR (KBr) cm$^{-1}$: 3358, 3286, 1644, 1538, 1495, 1343 Melting point: 161°–163° C.

No. 4: IR (KBr) cm$^{-1}$: 3364, 3128, 2852, 1606, 1537, 1466, 1354, 550 Melting point: 113°–115° C.

No. 5: IR (KBr) cm$^{-1}$: 3349, 3286, 2939, 1627, 1533, 1455 Melting point: 92°–94° C.

No. 6: IR (KBr) cm$^{-1}$: 3335, 3284, 3145, 2932, 2872, 1595, 1537, 1495 Melting point: 71°–73° C.

No. 7: IR (KBr) cm$^{-1}$: 3295, 2933, 1543, 1478, 1440, 1376, 1354, 1065, 980, 816 Melting point: 136°–138° C.

No. 8: IR (KBr) cm$^{-1}$: 3330, 3132, 2922, 1610, 1540, 1498, 1375, 984 Melting point: 76°–77° C.

No. 9: IR (KBr) cm$^{-1}$: 3352, 3286, 3065, 2836, 1537, 1497, 1378, 1321, 1064, 974, 810 Melting point: 76°–78° C.

No. 10: IR (KBr) cm$^{-1}$: 3358, 3291, 3126, 2825, 1624, 1551, 1530, 1338 Melting point: 155°–158° C.

No. 11: IR (KBr) cm$^{-1}$: 3372, 3315, 3259, 2866, 1609, 1535, 1475, 1438, 1377, 1359 Melting point: 102°–103° C.

No. 12: IR (KBr) cm$^{-1}$: 3359, 3280, 3124, 2921, 1539, 1505, 729 Melting point: 134°–136° C.

No. 13: IR (KBr) cm$^{-1}$: 3360, 3102, 3070, 2863, 1585, 1539, 1517, 1478, 1347, 1268 Melting point: 145°–146° C.

No. 14: IR (neat) cm$^{-1}$: 3361, 2934, 1658, 1615, 1540, 1262 Oily product

EXAMPLE 15

To a solution of 4.13 g of 3-(2-amino-3-hydroxypropoxy)-5-chloro-1,2-benzoisoxazole in 82 ml of ethyl acetate is added 13.6 ml of a dioxane solution (2.2N) of hydrogen chloride, and the crystals precipitated are collected by filtration to obtain 4.52 g of colorless, crystalline 3-(2-amino-3-hydroxypropoxy)-5-chloro-1,2-benzoisoxazole hydrochloride having a melting point of 216°–217° C.

IR (KBr) cm$^{-1}$: 3282, 2926, 1540, 1495, 1436, 1365, 1061, 806

EXAMPLE 16

To a solution of 0.5 g of 3-(2-tert-butoxycarbonylamino-3-hydroxypropoxy)-1,2-benzoisoxazole in 5 ml of tetrahydrofuran are added 0.154 g of 3-hydroxypyridine, 0.553 g of triphenylphosphine and 0.33 ml of diethyl azodicarboxylate at room temperature with ice-cooling, and they are subjected to reaction at room temperature for eight hours. The solvent is removed from the reaction mixture by distillation under reduced pressure, and the residue obtained is purified by a silica gel column chromatography [eluant:n-hexane:ethyl acetate=4:1], to obtain 0.32 g of oily 3-[2-tert-butoxycarbonylamino-3-(3-pyridyloxy)propoxy]-1,2-benzoisoxazole.

IR (KBr) cm$^{-1}$: 3331, 2978, 1713, 1614, 1538, 1445, 1368, 1234, 1161, 1052, 752

EXAMPLE 17

To a solution of 7.68 g of 3-[(3-tert-butoxycarbonyl-2,2-dimethyloxazolidin-4-yl)methoxy]-5-chloro-1,2-benzoisoxazole in 77 ml of chloroform and 77 ml of methanol is added 16 ml of a 2-propanol solution (7.5N) of hydrogen chloride at 20°–25° C., and they are subjected to reaction at the same temperature overnight. The crystals precipitated are collected by filtration, to obtain 4.47 g of 3-(2-amino-3-hydroxypropoxy)-5-chloro-1,2-benzoisoxazole hydrochloride.

IR (KBr) cm$^{-1}$: 3282, 2926, 1540, 1495, 1436, 1365, 1061, 806

EXAMPLES 18 TO 22

In the same manner as in Example 17, hydrochlorides of the compounds shown in Table 10 are obtained. Incidentally, R, $R_7$ and $R_8$ in Table 10 represent the corresponding substituents of a compound represented by the following formula:

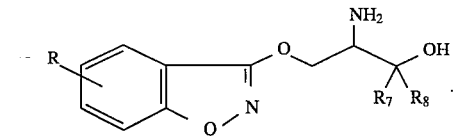

TABLE 10

| No. | R | $R_7$ | $R_8$ |
|---|---|---|---|
| 18*1 | 5, Cl | H | H |
| 19*2 | 5, Cl | H | H |
| 20*3 | 5, Cl | CH$_3$ | H |
| 21*4 | 5, Cl | H | CH$_3$ |
| 22 | 6, Cl | H | H |

*1: The 2-position of the side chain: (S) configuration
*2: The 2-position of the side chain: (R) configuration
*3: The 2-position and 3-position of the side chain: both (R) configuration
*4: The 2-position and 3-position of the side chain: both (S) configuration Physical properties of the compounds shown in Table 10 are shown below.

No. 18: IR (KBr) cm$^{-1}$: 3433, 3167, 3022, 2923, 1609, 1550, 1515, 1480, 1381, 1317, 1029, 1002, 812 Melting point: 206°–208° C.

No. 19: Melting point: 203°–205° C.

No. 20: IR (KBr) cm$^{-1}$: 3484, 3293, 3061, 1548, 1509, 1367 Melting point: 193°–195° C.

No. 21: Melting point: 196°–198° C.

No. 22: IR (KBr) cm$^{-1}$: 3332, 2958, 1614, 1532, 1433, 1403, 1042, 908, 820 Melting point: 220°–222° C.

EXAMPLE 23

(1) In the same manner as in Example 17, from 0.60 g of 3-[(3-tert-butoxycarbonyl-2,2-dimethyloxazolidin-4-yl)methoxy]-5-methyl-1,2-benzoisoxazole is obtained 0.39 g of colorless, crystalline 3-(2-amino-3-hydroxypropoxy)-5-methyl-1,2-benzoisoxazole hydrochloride.

(2) To a solution of 0.39 g of 3-(2-amino-3-hydroxypropoxy)-5-methyl-1,2-benzoisoxazole hydrochloride in 4 ml of water is added 4 ml of ethyl acetate, and the pH is adjusted to 11 with 10% (w/w) aqueous sodium hydroxide solution, after which the organic layer is separated. The separated organic layer is washed with a saturated saline solution and dried over anhydrous magnesium sulfate, after which the solvent is removed by distillation under reduced pressure to obtain 0.32 g of colorless, solid 3-(2-amino-3-hydroxypropoxy)-5-methyl-1,2-benzoisoxazole.

IR (KBr) cm$^{-1}$: 3352, 2926, 1612, 1538, 1502, 1455

EXAMPLE 24

In the same manner as in Example 23, oily 3-(2-amino-3-hydroxypropoxy)-5-methoxy-1,2-benzoisoxazole is obtained.

IR (neat) cm$^{-1}$: 3362, 2941, 1612, 1537, 1498

EXAMPLE 25

To a solution of 2.53 g of di-tert-butyl dicarbonate in 190 ml of ethyl acetate are added 38 ml of saturated aqueous sodium hydrogencarbonate solution and 38 ml of water. Thereto is added 3.83 g of 3-(2-amino-3-benzoyloxypropoxy)-5-chloro-1,2-benzoisoxazole hydrochloride at 20°–25° C., and they are subjected to reaction at the same temperature for one hour. The organic layer is separated from the reaction mixture and the separated organic layer is washed with a saturated saline solution and then dried over anhydrous magnesium sulfate, after which the solvent is removed by distillation under reduced pressure to obtain crystals. The crystals obtained are dissolved in 114 ml of methanol and 12 ml of 1N aqueous sodium hydroxide solution is further added, and they are subjected to reaction at 30°–40° C. for one hour. The solvent is removed form the reaction mixture by distillation under reduced pressure, and ethyl acetate and water are added to the residue obtained. After shaking, the organic layer is separated. The separated organic layer is washed with a saturated saline solution and dried over anhydrous magnesium sulfate, after which the solvent is removed by distillation under reduced pressure, to obtain 2.98 g of colorless, crystalline 3-(2-tert-butoxycarbonylamino-3-hydroxypropoxy)-5-chloro-1,2-benzoisoxazole having a melting point of 121°–122° C.

IR (KBr) cm$^{-1}$: 3360, 2974, 1694, 1594, 1515, 1480, 1365, 1241, 1172, 1063, 948, 820

EXAMPLES 26 TO 34

In the same manner as in Example 1(1) and Example 25, the compounds shown in Table 11 are obtained.

Incidentally, R, $R_1$ and $R_2$ in Table 11 represent the corresponding substituents of a compound represented by the following formula:

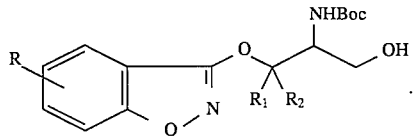

TABLE 11

| No. | R | $R_1$ | $R_2$ |
|---|---|---|---|
| 26 | 5, F | H | H |
| 27 | 5, —OCH$_2$Ph | H | H |
| 28 | 5, —SCH$_3$ | H | H |
| 29 | 5, —CN | H | H |
| 30 | 5, —CF$_3$ | H | H |
| 31 | 7, Cl | H | H |
| 32 | 5, Cl | CH$_3$ | CH$_3$ |
| 33 | 5, —NH$_2$ | H | H |
| 34 | 5, —SO$_2$—⟨ ⟩—OCH$_3$ | H | H |

Physical properties of the compounds shown in Table 11 are shown below.

No. 26: IR (KBr) cm$^{-1}$: 3484, 3357, 1699, 1542, 1522, 1502, 1452, 1358, 1310, 1250, 1157 Melting point: 121°–122° C.

No. 27: IR (KBr) cm$^{-1}$: 3462, 3342, 1692, 1543, 1499, 1456, 1351, 1313 Melting point: 138°–139° C.

No. 28: IR (KBr) cm$^{-1}$: 3471, 3330, 1686, 1531, 1478 Melting point: 141°–145° C.

No. 29: IR (KBr) cm$^{-1}$: 3473, 3328, 2229, 1698, 1540 Melting point: 136°–137° C.

No. 30: IR (KBr) cm$^{-1}$: 3363, 1684, 1629, 1554, 1524, 1317, 1166, 1121 Melting point: 118°–120° C.

No. 31: IR (KBr) cm$^{-1}$: 3431, 2977, 1694, 1615, 1540, 1421, 1248, 1167, 744 Solid product No. 32: IR (KBr) cm$^{-1}$: 3276, 1682, 1531, 1469, 1376, 804 Melting point: 125°–126° C.

No. 33: IR (neat) cm$^{-1}$: 3358, 1692, 1540, 1504, 1454, 1368, 1166 Oily product No. 34: IR (KBr) cm$^{-1}$: 3422, 3350, 2972, 1684, 1596, 1531, 1336, 1314, 1304, 1265, 1167 Melting point: 140°–142° C.

EXAMPLE 35

To a mixed solution of 19 ml of acetic acid and 19 ml of formic acid is added 3.84 g of 3-[(3-tert-butoxycarbonyl-2,2-dimethyloxazolidin-4-yl)methoxy]-5-chloro-1,2-benzoisoxazole at 20°–25° C., and they are subjected to reaction at the same temperature for one hour. Subsequently, the reaction mixture is poured into 190 ml of water and they are stirred at the same temperature for one hour. The crystals precipitated are collected by filtration, to obtain 2.78 g of 3-(2-tert-butoxycarbonylamino-3-hydroxypropoxy)-5-chloro-1,2-benzoisoxazole.

IR (KBr) cm$^{-1}$: 3360, 2974, 1694, 1594, 1515, 1480, 1365, 1241, 1172, 1063, 948, 820

EXAMPLES 36 TO 38

In the same manner as in Example 35, the compounds shown in Table 12 are obtained. Incidentally, R in Table 12 represents the substituent of a compound represented by the following formula:

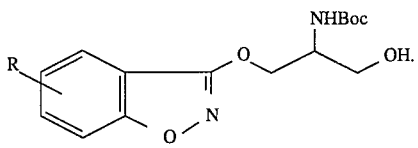

TABLE 12

| No. | R |
|---|---|
| 36 | 5, n-Bu |
| 37 | 5, Ph |
| 38 | 5, Cl 7, Cl |

Physical properties of the compounds shown in Table 12 are shown below.

No. 36: IR (neat) cm$^{-1}$: 3425, 2959, 2932, 1694, 1538, 1495, 1367 Oily product No. 37: IR (KBr) cm$^{-1}$: 3488, 3311, 1703, 1538, 1367 Melting point: 97°–99° C.

No. 38: IR (KBr) cm$^{-1}$: 3362, 2985, 1683, 1534, 1522, 1480, 1367 Melting point: 102°–103° C.

EXAMPLE 39

(1) A solution of 5.58 g of trityl chloride in 6 ml of N,N-dimethylformamide is added to a solution of 4.85 g of 3-(2-amino-3-hydroxypropoxy)-5-chloro-1,2-benzoisoxazole and 2.02 g of triethylamine in 12 ml of N,N-dimethylformamide at −40° to −30° C., and they are subjected to reaction at the same temperature for 30 minutes. Subsequently, ice water and ethyl acetate are added to the reaction mixture and the pH is adjusted to 2 with 2N hydrochloric acid. The organic layer is separated, and the separated organic layer is washed with a saturated saline solution and dried over anhydrous magnesium sulfate, after which the solvent is removed by distillation under reduced pressure. The residue obtained is crystallized from n-hexane and the crystals are collected by filtration, to obtain 7.28 g of colorless, crystalline 5-chloro-3-(2-tritylamino-3-hydroxypropoxy)-1,2-benzoisoxazole having a melting point of 142°–144° C.

(2) To a suspension of 0.44 g of 60% (w/w) sodium hydride in 49 ml of tetrahydrofuran is added 4.85 g of 5-chloro-3-(2-tritylamino-3-hydroxypropoxy)-1,2-benzoisoxazole at 20°–25° C. and they are refluxed for one hour. The reaction mixture is cooled to 5°–10° C., and thereafter, 1.56 g of methyl iodide is added, after which they are subjected to reaction at 20°–25° C. for five hours. The solvent is removed from the reaction mixture by distillation under reduced pressure, ethyl acetate and water are added to the residue obtained, and after shaking, the organic layer is separated. The separated organic layer is washed with a saturated saline solution and dried over anhydrous magnesium sulfate, after which the solvent is removed by distillation under reduced pressure. The residue obtained is crystallized from n-hexane and the crystals are collected by filtration, to obtain 5-chloro-3-(3-methoxy-2-tritylaminopropoxy)-1,2-benzoisoxazole.

(3) To a suspension of 5-chloro-3-(3-methoxy-2-tritylaminopropoxy)-1,2-benzoisoxazole in 49 ml of 2-propanol is added 1.5 ml of a 2-propanol solution (7.5N) of hydrogen chloride, and they are refluxed for ten minutes, after which the crystals are collected by filtration, to obtain 2.34 g of colorless, crystalline 3-(2-amino-3-methoxypropoxy)-5-chloro-1,2-benzoisoxazole hydrochloride having a melting point of 200°–202° C.

IR (KBr) cm$^{-1}$: 2930, 1552, 1526, 1481, 1384, 1310, 1102, 1004, 816

EXAMPLES 40 TO 46

In the same manner as in Example 39, hydrochlorides of the compounds shown in Table 13 are obtained. Incidentally, R, $R_7$, $R_8$ and $R_9$ in Table 13 represent the corresponding substituents of a compound represented by the following formula:

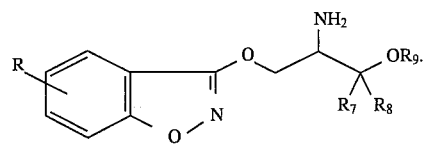

TABLE 13

| No. | R | $R_7$ | $R_8$ | $R_9$ |
|---|---|---|---|---|
| 40*[1] | 5, Cl | H | H | $CH_3$ |
| 41*[2] | 5, Cl | H | H | $CH_3$ |
| 42 | 5, —$OCH_2Ph$ | H | H | $CH_3$ |
| 43 | 5, Cl | $CH_3$ | $CH_3$ | $CH_3$ |
| 44 | 5, Cl | H | H | —$CH_2Ph$ |
| 45 | 5, Cl | H | H | —$CH_2CH=CH_2$ |
| 46 | 5, Cl | H | H | —$CH_2C\equiv CH$ |

*[1]: The 2-position of the side chain: (S) configuration
*[2]: The 2-position of the side chain: (R) configuration Physical properties of the compounds shown in Table 13 are shown below.

No. 40: IR (KBr) cm$^{-1}$: 2934, 2647, 2518, 1610, 1550, 1525, 1480, 1459, 1439, 1309, 1101, 923, 816 Melting point: 206°–209° C.

No. 41: Melting point: 209°–211° C.

No. 42: IR (KBr) cm$^{-1}$: 3447, 2923, 1615, 1584, 1551, 1499, 1104 Melting point: 201°–204° C.

No. 43: IR (KBr) cm$^{-1}$: 3447, 2980, 1609, 1539, 1477, 1364 Melting point: 218°–219° C.

No. 44: IR (KBr) cm$^{-1}$: 3448, 2900, 1610, 1544, 1479, 1362 Melting point: 211°–214° C.

No. 45: IR (KBr) cm$^{-1}$: 2898, 1544, 1521, 1478, 1368, 1310, 1260, 1124, 929, 812 Melting point: 202°–203° C.

No. 46: IR (KBr) cm$^{-1}$: 3298, 2900, 1543, 1479, 1368, 1310, 1118, 812 Melting point: 208°–209° C.

EXAMPLE 47

(1) To a suspension of 5.58 g of 3-(2-amino-3-hydroxypropoxy)-5-chloro-1,2-benzoisoxazole hydrochloride in 56 ml of methylene chloride and 11 ml of methanol are added 4.45 g of triethylamine and 5.42 g of di-tert-butyl dicarbonate at 5°–10° C., and they are subjected to reaction at 20°–25° C. for three hours. Water is added to the reaction mixture and the pH is adjusted to 2 with 2N hydrochloric acid, after which the organic layer is separated. The separated organic layer is washed with a saturated saline solution and dried over anhydrous magnesium sulfate, after which the solvent is removed by distillation under reduced pressure. The residue obtained is crystallized from n-hexane and the crystals are collected by filtration, to obtain 6.44 g of 3-(2-tert-butoxycarbonylamino-3-hydroxypropoxy)-5-chloro-1,2-benzoisoxazole.

(2) To a suspension of 3.43 g of 3-(2-tert-butoxycarbonylamino-3-hydroxypropoxy)-5-chloro-1,2-benzoisoxazole in 34 ml of methylene chloride is added 1.70 g of chlorosulfonyl isocyanate at −45° to −40° C., and the temperature thereof is elevated to 0° C., after which they are subjected to reaction at the same temperature for one hour. To the reaction mixture is added 10 ml of water and they are subjected to reaction at 20°–25° C. for one hour, after which methylene chloride is removed by distillation under reduced pressure. The crystals obtained are collected by filtration, to obtain 3.30 g of 3-(3-carbamoyloxy-2-tert-butoxycarbonylaminopropoxy)-5-chloro-1,2-benzoisoxazole.

(3) To a suspension of 3.28 g of 3-(3-carbamoyloxy-2-tert-butoxycarbonylaminopropoxy)-5-chloro-1,2-benzoisoxazole in 33 ml of chloroform and 33 ml of methanol is added 7.1 ml of conc hydrochloric acid at 20°–25° C., and they are subjected to reaction at the same temperature overnight. The solvent is removed from the reaction mixture by distillation under reduced pressure, and ethyl acetate and water are added to the residue obtained. After shaking, the aqueous layer is separated. To the separated aqueous layer is again added ethyl acetate, and the pH is adjusted to 10 with a 10% (w/w) aqueous sodium hydroxide solution, after which the organic layer is separated. The separated organic layer is washed with a saturated saline solution and dried over anhydrous magnesium sulfate, after which the solvent is removed by distillation under reduced pressure. The crystals obtained are dissolved in 66 ml of ethanol, and to this solution is added 4.5 ml of a dioxane solution (2.2N) of hydrogen chloride at 20°–25° C., after which the crystals precipitated are collected by filtration, to obtain 2.16 g of colorless, crystalline 3-(2-amino-3-carbamoyloxypropoxy)-5-chloro-1,2-benzoisoxazole hydrochloride having a melting point of 215°–216° C.

IR (KBr) cm$^{-1}$: 3397, 2901, 1702, 1600, 1542, 1367, 1313, 1079, 816

EXAMPLES 48 TO 80

In the same manner as in Example 47, hydrochlorides of the compounds shown in Table 14a to Table 14e are obtained. Incidentally, R, $R_1$, $R_2$, $R_3$, $R_7$ and $R_8$ in Table 14a to Table 14e represent the corresponding substituents of a compound represented by the following formula:

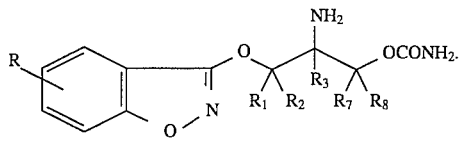

TABLE 14a

| No. | R | $R_1$ | $R_2$ | $R_3$ | $R_7$ | $R_8$ |
|---|---|---|---|---|---|---|
| 48*[1] | 5, Cl | H | H | H | H | H |
| 49*[2] | 5, Cl | H | H | H | H | H |
| 50*[3] | 5, Cl | H | H | H | CH$_3$ | H |
| 51*[4] | 5, Cl | H | H | H | H | CH$_3$ |
| 52 | 5, Cl | H | H | CH$_3$ | H | H |
| 53 | 5, —CH=CH$_2$ | H | H | H | H | H |
| 54 | 5, Et | H | H | H | H | H |

*[1]: The 2-position of the side chain: (R) configuration
*[2]: The 2-position of the side chain: (S) configuration
*[3]: The 2-position and 3-position of the side chain: both (R) configuration
*[4]: The 2-position and 3-position of the side chain: both (S) configuration TABLE 14b

| No. | R | $R_1$ | $R_2$ | $R_3$ | $R_7$ | $R_8$ |
|---|---|---|---|---|---|---|
| 55 | 5, —NO$_2$ | H | H | H | H | H |
| 56 | 5, n-Bu | H | H | H | H | H |
| 57 | 5, Ph | H | H | H | H | H |
| 58 | 5, Cl 7, Cl | H | H | H | H | H |
| 59 | 6, Cl | H | H | H | H | H |
| 60 | 5, —N(pyrrolidinyl) | H | H | H | H | H |
| 61 | 5, —O—(4-nitro-2-chlorophenyl) | H | H | H | H | H |

TABLE 14c

| No. | R | $R_1$ | $R_2$ | $R_3$ | $R_7$ | $R_8$ |
|---|---|---|---|---|---|---|
| 62 | 5, —COPh | H | H | H | H | H |
| 63 | 5, —CN | H | H | H | H | H |
| 64 | 5, —CF$_3$ | H | H | H | H | H |
| 65 | 5, —O-n-Bu | H | H | H | H | H |
| 66 | 6, —OCH$_3$ | H | H | H | H | H |
| 67 | 5, I | H | H | H | H | H |
| 68 | 5, Cl | H | H | H | CH$_3$ | CH$_3$ |

TABLE 14d

| No. | R | $R_1$ | $R_2$ | $R_3$ | $R_7$ | $R_8$ |
|---|---|---|---|---|---|---|
| 69 | 5, —NHCOPh | H | H | H | H | H |
| 70 | 5, —CH$_3$ | H | H | H | H | H |
| 71 | 5, —OCH$_3$ | H | H | H | H | H |
| 72 | 5, 6 —CH=CH—CH=CH— | H | H | H | H | H |
| 73 | 5, Br | H | H | H | H | H |
| 74 | H | H | H | H | H | H |
| 75 | 7, Cl | H | H | H | H | H |

TABLE 14e

| No. | R | $R_1$ | $R_2$ | $R_3$ | $R_7$ | $R_8$ |
|---|---|---|---|---|---|---|
| 76 | 5, —SCH$_3$ | H | H | H | H | H |
| 77 | 5, F | H | H | H | H | H |
| 78 | 5, —OCH$_2$Ph | H | H | H | H | H |
| 79 | 5, —SO$_2$—(4-methoxyphenyl) | H | H | H | H | H |
| 80 | 5, Cl | CH$_3$ | CH$_3$ | H | H | H |

Physical properties of the compounds shown in Table 14a to Table 14e are shown below.

No. 48: IR (KBr) cm$^{-1}$: 3385, 3152, 2535, 1698, 1613, 1525, 1479, 1354 Melting point: 210°–211° C.

No. 49: Melting point: 209°–211° C.

No. 50: IR (KBr) cm$^{-1}$: 3472, 3128, 1699, 1538, 1396, Melting point: 209°–210° C.

No. 51: Melting point: 210°–211° C.

No. 52: IR (KBr) cm$^{-1}$: 3638, 3392, 3196, 2906, 1705, 1628, 1547, 1525, 1421, 1363, 1317, 1099, 1009, 819 Melting point: 230°–231° C.

No. 53: IR (KBr) cm$^{-1}$: 3450, 3357, 2904, 1750, 1722, 1714, 1601, 1544, 1519, 1487, 1462, 1393, 1371, 1329 Melting point: 211° C. (decomp.)

No. 54: IR (KBr) cm$^{-1}$: 3370, 3248, 2918, 1729, 1715, 1614, 1538, 1495, 1462, 1418, 1372, 1347, 1312, 1227 Melting point: 210°–212° C.

No. 55: IR (KBr) cm$^{-1}$: 3331, 2914, 2836, 1610, 1538, 1476, 1441, 1365, 1311, 1259 Melting point: 212°–213° C.

No. 56: IR (KBr) cm$^{-1}$: 3479, 3366, 2928, 1750, 1724, 1605, 1541, 1495, 1390, 1371, 1314 Melting point: 181°–182° C.

No. 57: IR (KBr) cm$^{-1}$: 3497, 3370, 2899, 1702, 1605, 1544, 1508, 1484, 1374, 1319 Melting point: 207°–209° C.

No. 58: IR (KBr) cm$^{-1}$: 3493, 3052, 2954, 2902, 1732, 1602, 1545, 1520, 1481, 1365, 1313 Melting point: 222°–223° C.

No. 59: IR (KBr) cm$^{-1}$: 3415, 3254, 2905, 1715, 1611, 1537, 1434, 1370, 1319 Melting point: 222°–223° C.

No. 60: IR (KBr) cm$^{-1}$: 3446, 2957, 1718, 1544, 1506, 1329, 731 Melting point: 216°–218° C.

No. 61: IR (KBr) cm$^{-1}$: 3421, 2961, 1718, 1519, 1345, 1270 Melting point: 193°–196° C.

No. 62: IR (KBr) cm$^{-1}$: 3440, 2902, 1719, 1654, 1617, 1543, 1331, 1264 Melting point: 196°–197° C.

No. 63: IR (KBr) cm$^{-1}$: 3404, 2233, 1717, 1546 Melting point: 180°–182° C.

No. 64: IR (KBr) cm$^{-1}$: 3373, 2957, 1750, 1706, 1629, 1547, 1312, 1122 Melting point: 219°–220° C.

No. 65: IR (KBr) cm$^{-1}$: 3394, 2956, 1731, 1699, 1540, 1498 Melting point: 147°–149° C.

No. 66: IR (KBr) cm$^{-1}$: 3421, 3251, 2961, 1716, 1628, 1534, 1453 Melting point: 215°–217° C.

No. 67: IR (KBr) cm$^{-1}$: 3436, 2904, 1716, 1605, 1540, 1363, 551 Melting point: 211°–213° C.

No. 68: IR (KBr) cm$^{-1}$: 3438, 3309, 2935, 1754, 1722, 1606, 1534, 1514, 1362 Melting point: 213°–215° C.

No. 69: IR (KBr) cm$^{-1}$: 3426, 2963, 1718, 1651, 1542, 1490, 1339 Melting point: 140° C. (decomp.)

No. 70: IR (KBr) cm$^{-1}$: 3407, 3245, 3166, 2946, 1707, 1611, 1538, 1368, 1319 Melting point: 215°–216° C.

No. 71: IR (KBr) cm$^{-1}$: 3442, 2942, 1716, 1615, 1596, 1541, 1501, 1339 Melting point: 198°–200° C.

No. 72: IR (KBr) cm$^{-1}$: 3395, 3243, 3168, 2902, 1705, 1598, 1551 Melting point: 228°–230° C.

No. 73: IR (KBr) cm$^{-1}$: 3384, 3226, 3162, 2342, 1700, 1610, 1540, 1474, 1365, 1393, 1316 Melting point: 211°–212° C.

No. 74: IR (KBr) cm$^{-1}$: 3385, 3242, 2902, 2548, 1704, 1614, 1532, 1448 Melting point: 232°–234° C.

No. 75: IR (KBr) cm$^{-1}$: 3448, 3182, 2928, 1705, 1616, 1538, 1335, 1088, 747, 660 Melting point: 198°–200° C.

No. 76: IR (KBr) cm$^{-1}$: 3458, 2893, 1759, 1743, 1715, 1601, 1539, 1514, 1475 Melting point: 219°–220° C.

No. 77: IR (KBr) cm$^{-1}$: 1709, 1541, 1504, 1367, 1100 Melting point: 221°–222° C.

No. 78: IR (KBr) cm$^{-1}$: 1742, 1710, 1533, 1516, 1497, 1451, 1343, 1221, 1103 Melting point: 211°–213° C.

No. 79: IR (KBr) cm$^{-1}$: 3472, 3341, 2960, 1733, 1594, 1552, 1499, 1374, 1338, 1259, 1145, 1090 Melting point: 212°–214° C.

No. 80: IR (KBr) cm$^{-1}$: 1725, 1526, 1466, 1374, 1356 Melting point: 213°–214° C.

EXAMPLE 81

(1) A solution of 1.00 g of 3-(2-tert-butoxycarbonylamino-3-hydroxypropoxy)-5-chloro-1,2-benzoisoxazole and 0.73 g of triethylamine in 5 ml of methylene chloride is added to a solution of 0.42 g of trichloromethyl chloroformate in 5 ml of methylene chloride at 5°–7° C. over 20 minutes, and they are further subjected to reaction at the same temperature for 30 minutes. To this solution is added 0.32 g of tert-butyl carbazinate, and the temperature is elevated to 25° C., at which they are subjected to reaction for 30 minutes. Water is added to the reaction mixture and after shaking, the organic layer is separated. The separated organic layer is washed with a saturated saline solution and dried over anhydrous magnesium sulfate, after which the solvent is removed by distillation under reduced pressure, to obtain 3-(2-tert-butoxycarbonylamino-3-hydrazinocarbonyloxypropoxy)-5-chloro-1,2-benzoisoxazole.

(2) In 10 ml of 2-propanol is dissolved 3-(2-tert-butoxycarbonylamino-3-hydrazinocarbonyloxypropoxy)-5-chloro-1,2-benzoisoxazole, and 12.8 ml of a 2-propanol solution (7.5N) of hydrogen chloride is added thereto, after which they are subjected to reaction at 20°–25° C. for 1.5 hours. The solvent is removed from the reaction mixture by distillation under reduced pressure, and the crystals obtained are washed with 5 ml of ethyl acetate and then collected by filtration, to obtain 0.52 g of colorless, crystalline 3-(2-amino-3-hydrazinocarbonyloxypropoxy)-5-chloro-1,2-benzoisoxazole hydrochloride having a melting point of 190°–191° C.

IR (KBr) cm$^{-1}$: 3402, 2958, 1748, 1610, 1539, 1478, 1279, 1259, 802

EXAMPLE 82

(1) A solution of 1.00 g of 3-(2-tert-butoxycarbonylamino-3-hydroxypropoxy)-5-chloro-1,2-benzoisoxazole and 0.73 g of triethylamine in 5 ml of methylene chloride is added to a solution of 0.42 g of trichloromethyl chloroformate in 5 ml of methylene chloride at 5°–7° C. over 20 minutes, and they are subjected to reaction at the same temperature for 30 minutes. This solution is added to a solution of 1.20 g of methoxyamine hydrochloride and 0.78 g of sodium methoxide in 15 ml of methanol at −30° C. and the temperature is elevated to 0° C., at which they are subjected to reaction for 30 minutes. Water is added to the reaction mixture, and after shaking, the organic layer is separated. The separated organic layer is washed with a saturated saline solution and dried over anhydrous magnesium sulfate, after which the solvent is removed by distillation under reduced pressure to obtain 3-(2-tert-butoxycarbonylamino-3-methoxyaminocarbonyloxypropoxy)-5-chloro-1,2-benzoisoxazole.

(2) 3-(2-tert-Butoxycarbonylamino-3-methoxyaminocarbonyloxypropoxy)-5-chloro-1,2-benzoisoxazole is dissolved in 10 ml of 2-propanol, and 12.8 ml of a 2-propanol solution (7.5N) of hydrogen chloride is added, after which they are subjected to reaction at 20°–25° C. overnight. The solvent is removed from the reaction mixture by distillation under reduced pressure, and the crystals obtained are washed with 2-propanol and then collected by filtration, to obtain 0.46 g of colorless, crystalline 3-(2-amino-3-methoxyaminocarbonyloxypropoxy)-5-chloro-1,2-benzoisoxazole hydrochloride having a melting point of 199°–200° C.

IR (KBr) cm$^{-1}$: 3203, 2935, 1754, 1538, 1503, 1482, 1260, 1130, 808

EXAMPLE 83

(1) A solution of 1.00 g of 3-(2-tert-butoxycarbonylamino-3-hydroxypropoxy)-5-chloro-1,2-benzoisoxazole in 5 ml of methylene chloride is added to a solution of 0.31 g of N-(chlorocarbonyl) isocyanate in 10 ml of methylene chloride at −50° to −40° C. This solution is added to 10 ml of a methanol solution (8.0N) of ammonia at −20° C. over 20 minutes, and the temperature is elevated to 0° C., at which they are subjected to reaction for 30 minutes. Water is added to the reaction mixture, and after shaking, the organic layer is separated. The separated organic layer is washed with a saturated saline solution and dried over anhydrous magnesium sulfate, after which the solvent is removed by distillation under reduced pressure, to obtain 3-(3-ureidocarbonyloxy-2-tert-butoxycarbonylaminopropoxy)-5-chloro-1,2-benzoisoxazole.

(2) 3-(3-Ureidocarbonyloxy-2-tert-butoxycarbonylaminopropoxy)-5-chloro-1,2-benzoisoxazole is suspended in 10 ml of methanol and 5 ml of chloroform, and 12.8 ml of a 2-propanol solution (7.5N) of hydrogen chloride is added, after which they are subjected to reaction at 20°–25° C. overnight. The crystals precipitated are collected by filtration, to obtain 0.62 g of colorless, crystalline 3-(2-amino-3-ureidocarbonyloxypropoxy)-5-chloro-1,2-benzisoxazole hydrochloride having a melting point of 203°–204° C.

IR (KBr) cm$^{-1}$: 3377, 3333, 3194, 2966, 1732, 1671, 1536, 1483, 1257, 1222, 818

EXAMPLE 84

A solution of 1.00 g of 3-(2-tert-butoxycarbonylamino-3-hydroxypropoxy)-5-chloro-1,2-benzoisoxazole in 5 ml of methylene chloride is added to a solution of 0.31 g of N-(chlorocarbonyl) isocyanate in 10 ml of methylene chloride at −50° to −40° C. To this solution is added 10 ml of methanol at −40° C., and the temperature is elevated to 0° C., at which they are subjected to reaction for 30 minutes. The solvent is removed from the reaction mixture by distillation under reduced pressure, and to the residue obtained is added 12.8 ml of a 2-propanol solution (7.5N) of hydrogen chloride, after which they are subjected to reaction at 20°–25° C. for 30 minutes. The solvent is removed from the reaction mixture by distillation under reduced pressure. To the residue obtained are added ethyl acetate and a saturated aqueous sodium hydrogencarbonate solution, and after shaking, the organic layer is separated. The separated organic layer is washed with a saturated saline solution and dried over anhydrous magnesium sulfate, after which 9.6 ml of a 2-propanol solution (7.5N) of hydrogen chloride is added. The crystals obtained are collected by filtration, to obtain 0.42 g of colorless, crystalline 3-(2-amino-3-methoxycarbonylaminocarbonyloxypropoxy)-5-chloro-1,2-benzoisoxazole hydrochloride having a melting point of 184°–185° C.

IR (KBr) cm$^{-1}$: 3348, 3300, 1780, 1614, 1539, 1476, 1223, 1102, 810, 786

EXAMPLE 85

(1) To a solution of 0.50 g of 3-(2-tert-butoxycarbonylamino-3-hydroxypropoxy)-5-chloro-1,2-benzoisoxazole in 5 ml of N,N-dimethylformamide is added 0.14 g of cuprous chloride. To this solution is added a solution of 0.13 g of methyl isocyanate in 5 ml of methylene chloride at 20°–25° C., and they are further subjected to reaction at the same temperature for 30 minutes. Water and ethyl acetate are added to the reaction mixture, and after shaking, the organic layer is separated. The separated organic layer is washed with water and a saturated saline solution and dried over anhydrous magnesium sulfate, after which the solvent is removed by distillation under reduced pressure, to obtain 3-(2-tert-butoxycarbonylamino-3-methylaminocarbonyloxypropoxy)-5-chloro-1,2-benzoisoxazole.

(2) In 10 ml of methanol is dissolved 3-(2-tert-butoxycarbonylamino-3-methylaminocarbonyloxypropoxy)-5-chloro-1,2-benzoisoxazole, and to this solution is added 9.6 ml of a 2-propanol solution (7.5N) of hydrogen chloride, and they are subjected to reaction at 20°–25° C. for 4.5 hours. The solvent is removed from the reaction mixture by distillation under reduced pressure, and to the residue obtained is added 5 ml of 2-propanol, after which the crystals precipitated are collected by filtration, to obtain 0.30 g of colorless, crystalline 3-(2-amino-3-methylaminocarbonyloxypropoxy)-5-chloro-1,2-benzoisoxazole hydrochloride having a melting point of 206°–209° C.

IR (KBr) cm$^{-1}$: 3440, 3393, 2892, 1721, 1542, 1479, 810

EXAMPLES 86 TO 88

In the same manner as in Example 85, the hydrochlorides of the compounds shown in Table 15 are obtained. Incidentally, $R_{9a}$ in Table 15 represents the substituent of a compound represented by the following formula:

TABLE 15

| No. | $R_{9a}$ |
|---|---|
| 86 | Et |
| 87 | —(CH$_2$)$_6$CH$_3$ |
| 88 | cyclohexyl (H) |

Physical properties of the compounds shown in Table 15 are shown below.

No. 86: IR (KBr) cm$^{-1}$: 3441, 2896, 1728, 1543, 1528, 1478, 1366, 1230, 1038, 812 Solid product No. 87: IR (KBr) cm$^{-1}$: 3365, 3033, 2962, 2927, 2856, 1723, 1548, 1364, 817 Melting point: 204°–205° C.

No. 88: IR (KBr) cm$^{-1}$: 3361, 2943, 1719, 1534, 1482, 1359, 1226, 1059, 930, 814 Melting point: 241°–243° C.

EXAMPLE 89

To a solution of 0.50 g of 3-(2-amino-3-methoxypropoxy)-5-chloro-1,2-benzoisoxazole are added 0.41 g of p-toluenesulfonic acid and 0.34 ml of 37% formalin, and 0.26 g of sodium cyanoborohydride is then added at 15°–20° C., after which they are subjected to reaction at the same temperature for one hour. Water and ethyl acetate are added to the reaction mixture, and the pH is adjusted to 10 with a 10% (w/w) aqueous sodium hydroxide solution and the organic layer is separated. The separated organic layer is washed with a saturated saline solution and dried over anhydrous magnesium sulfate, after which 0.89 ml of a dioxane solution (2.2N) of hydrogen chloride is added. The crystals precipitated are collected by filtration and recrystallized from a mixed solvent of acetone and methanol, to obtain 0.35 g of colorless, crystalline 5-chloro-3-(2-dimethylamino-3-methoxypropoxy)-1,2-benzoisoxazole hydrochloride having a melting point of 163°–164° C.

IR (KBr) cm$^{-1}$: 2958, 1532, 1472, 1352, 1112, 1005, 819

EXAMPLE 90

In the same manner as in Example 89, 5-chloro-3-(2-dimethylamino-3-carbamoyloxypropoxy)-1,2-benzoisoxazole hydrochloride having a melting point of 134°–139° C. is obtained.

IR (KBr) cm$^{-1}$: 3428, 1740, 1716, 1609, 1537, 1479

EXAMPLE 91

To a suspension of 0.50 g of 3-(2-amino-3-methoxypropoxy)-5-chloro-1,2-benzoisoxazole and 0.5 g of 3,5-di-tert-butyl-4-hydroxybenzaldehyde in 5 ml of methanol is added 0.41 g of p-toluenesulfonic acid at 20°–25° C., and they are subjected to reaction at the same temperature for one hour. Subsequently, 0.13 g of sodium cyanoborohydride is added at 20°–25° C., and they are subjected to reaction at the same temperature overnight. Water and ethyl acetate are added to the reaction mixture and the pH is adjusted to 10 with a 10% (w/w) aqueous sodium hydroxide solution, after which the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane:ethyl acetate=5:1], to obtain an oily product. The oily product obtained is dissolved in 10 ml of diethyl ether and 1 ml of water and to this solution is added 0.58 ml of a dioxane solution (2.2N) of hydrogen chloride, after which the crystals precipitated are collected by filtration and recrystallized from 50% ethanol, to obtain 0.27 g of colorless, crystalline 3-[2-(3,5-di-tert-butyl-4-hydroxybenzyl)amino-3-methoxypropoxy]-5-chloro-1,2-benzoisoxazole hydrochloride having a melting point of 191°–192° C.

IR (KBr) cm$^{-1}$: 3622, 2985, 1544, 1479, 1441, 1367, 1122, 985, 819

EXAMPLE 92

In the same manner as in Example 91, 3-(2-benzylamino-3-methoxypropoxy)-5-chloro-1,2-benzoisoxazole hydrochloride having a melting point of 206°–207° C. is obtained.

IR (KBr) cm$^{-1}$: 2678, 1542, 1476, 1113, 957, 805, 746, 701

EXAMPLE 93

(1) To 0.29 ml of formic acid is added 0.74 ml of acetic anhydride, and they are subjected to reaction at 40° C. for one hour. To the reaction mixture are added 5 ml of N,N-dimethylformamide and 1.00 g of 3-(2-amino-3-methoxypropoxy)-5-chloro-1,2-benzoisoxazole, and they are subjected to reaction at the same temperature for one hour. To the reaction mixture are added water and ethyl acetate, and after shaking, the organic layer is separated. Water is added again to the separated organic layer and the pH is adjusted to 8 with an aqueous sodium hydroxide solution, after which the organic layer is separated. The separated organic layer is washed with a saturated saline solution and dried over anhydrous magnesium sulfate, after which the solvent is removed by distillation under reduced pressure. Upon recrystallization from a mixed solvent of diisopropyl ether and ethyl acetate, there is obtained 0.50 g of colorless, crystalline 5-chloro-3-(2-formylamino-3-methoxypropoxy)-1,2-benzoisoxazole having a melting point of 90°–92° C.

(2) Under a nitrogen stream, 0.27 g of sodium borohydride and 0.86 ml of a boron trifluoride-diethyl ether complex salt are added to a solution of 0.40 g of 5-chloro-3-(2-formylamino-3-methoxypropoxy)-1,2-benzoisoxazole in 6 ml of tetrahydrofuran at –45° to –40° C. The temperature is elevated to 20°–25° C., and then, they are subjected to reaction at the same temperature for two hours. To the reaction mixture is added 15 ml of methanol with ice-cooling, and then, 0.58 ml of a dioxane solution (2.2N) of hydrogen chloride is added, after which they are stirred for ten minutes. Thereafter, the solvent is removed by distillation under reduced pressure. To the residue obtained are added ethyl acetate and water, and the pH is adjusted to 9 with a 10% (w/w) aqueous sodium hydroxide solution, after which the organic layer is separated. The separated organic layer is washed with a saturated saline solution and dried over anhydrous magnesium sulfate, after which the solvent is removed by distillation under reduced pressure. The residue obtained is dissolved in 8 ml of 2-propanol, and to this solution is added 0.70 ml of a dioxane solution (2.2N) of hydrogen chloride, after which the crystals precipitated are collected by filtration, to obtain 0.25 g of colorless, crystalline 3-(2-methylamino-3-methoxypropoxy)-5-chloro-1,2-benzoisoxazole hydrochloride having a melting point of 197°–198° C.

IR (KBr) cm$^{-1}$: 2949, 2812, 1540, 1479, 1367, 1118, 1000, 814

EXAMPLE 94

In the same manner as in Example 93, 3-(3-carbamoyloxy-2-methylaminopropoxy)-5-chloro-1,2-benzoisoxazole hydrochloride having a melting point of 134°–142° C. is obtained.

IR (KBr) cm$^{-1}$: 3412, 2999, 1733, 1601, 1541, 1478

EXAMPLE 95

To a suspension of 0.40 g of 3-(2-amino-3-methoxypropoxy)-5-benzyloxy-1,2-benzoisoxazole hydrochloride in 20 ml of methanol is added 0.1 g of 5% palladium carbon, and they are subjected to catalytic reduction at 20°–25° C. under atmospheric pressure. The 5% palladium carbon is removed from the reaction mixture by filtration, and the solvent is removed from the filtrate by distillation under reduced pressure. The residue obtained is crystallized from 2-propanol, and the crystals are collected by filtration, to obtain 0.16 g of colorless, crystalline 3-(2-amino-3-methoxypropoxy)-5-hydroxy-1,2-benzoisoxazole hydrochloride having a melting point of 187°–190° C.

IR (KBr) cm$^{-1}$: 3477, 3312, 3200, 3039, 2922, 1593, 1537, 1509, 1101

EXAMPLE 96

(1) To a solution of 0.49 g of 5-amino-3-(2-tert-butoxycarbonylamino-3-hydroxypropoxy)-1,2-benzoisoxazole in 10 ml of ethyl acetate is added 0.42 g of di-tert-butyl dicarbonate, and they are subjected to reaction at 20°–25° C. for five hours. Water is added to the reaction mixture, and after shaking, the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane:ethyl acetate=3:2] to obtain 0.57 g of colorless, crystalline 5-tert-butoxycarbonylamino-3-(2-tert-butoxycarbonylamino-3-hydroxypropoxy)-1,2-benzoisoxazole.

(2) To a solution of 0.47 g of 5-tert-butoxycarbonylamino-3-(2-tert-butoxycarbonylamino-3-hydroxypropoxy)-1,2-benzoisoxazole in 10 ml of methylene chloride is added 0.21 g of chlorosulfonyl isocyanate at −45° to −40° C., and the temperature is elevated to 0° C., after which they are subjected to reaction at the same temperature for one hour. Subsequently, 10 ml of water is added, and they are subjected to reaction at 20°–25° C. for one hour. The solvent is removed from the reaction mixture by distillation under reduced pressure, and the crystals obtained are collected by filtration, to obtain 0.47 g of colorless, crystalline 3-(3-carbamoyloxy-2-tert-butoxycarbonylaminopropoxy)-5-tert-butoxycarbonylamino-1,2-benzoisoxazole.

(3) To a solution of 0.47 g of 3-(3-carbamoyloxy-2-tert-butoxycarbonylaminopropoxy)-5-tert-butoxycarbonylamino-1,2-benzoisoxazole in 10 ml of methanol is added 5.0 ml of a dioxane solution (2.2N) of hydrogen chloride at 5°–10° C. and they are subjected to reaction at 20°–25° C. overnight. The solvent is removed from the reaction mixture by distillation under reduced pressure, and the residue obtained is crystallized from 2-propanol, after which the crystals are collected by filtration, to obtain 0.21 g of colorless, crystalline 5-amino-3-(2-amino-3-carbamoyloxypropoxy)-1,2-benzoisoxazole hydrochloride having a melting point of 230°–231° C.

IR (KBr) cm$^{-1}$: 3463, 2870, 1744, 1722, 1545, 1507

EXAMPLE 97

(1) To a solution of 0.59 g of 5-amino-3-(2-tert-butoxycarbonylamino-3-hydroxypropoxy)-1,2-benzoisoxazole in 12 ml of methylene chloride is added 0.17 g of acetic formic anhydride at 5°–10° C., and they are subjected to reaction at 20°–25° C. for one hour. The solvent is removed from the reaction mixture by distillation under reduced pressure, and the residue obtained is crystallized from n-hexane, after which the crystals are collected by filtration, to obtain 0.52 g of colorless, crystalline 3-(2-tert-butoxycarbonylamino-3-hydroxypropoxy)-5-formylamino-1,2-benzoisoxazole having a melting point of 104°–105° C.

(2) To a suspension of 0.45 g of 3-(2-tert-butoxycarbonylamino- 3-hydroxypropoxy)-5-formylamino-1,2-benzoisoxazole in 9 ml of methylene chloride are added 0.14 g of 3,4-dihydro-2H-pyran and 0.06 g of pyridinium p-toluenesulfonate at 20°–25° C., and they are subjected to reaction at 40° C. for one hour. Water is added to the reaction mixture and the pH is adjusted to 9 with a saturated aqueous sodium hydrogencarbonate solution, after which the organic layer is separated. The separated organic layer is dried over anhydrous magnesium sulfate, and the solvent is then removed by distillation under reduced pressure, to obtain oily 3-[2-tert-butoxycarbonylamino-3-(2,3,4,5-tetrahydropyranyloxy)propoxy]-5-formylamino-1,2-benzoisoxazole.

(3) 3-[2-tert-Butoxycarbonylamino-3-(2,3,4,5-tetrahydropyranyloxy)propoxy]-5-formylamino-1,2-benzoisoxazole is dissolved in 9 ml of tetrahydrofuran, and at 5°–10° C., 3.2 ml of a tetrahydrofuran solution (1M) of diborane is added, after which they are subjected to reaction at 20°–25° C. for one hour. Subsequently, 9 ml of water is added and the pH is adjusted to 0 with 6N hydrochloric acid, after which they are subjected to reaction at 20°–25° C. for one hour. The reaction mixture is concentrated under reduced pressure, ethyl acetate is added, and, after shaking, the aqueous layer is separated. Ethyl acetate is added again to the separated aqueous layer and the pH is adjusted to 11 with potassium carbonate, after which the organic layer is separated. The separated organic layer is washed with a saturated saline solution and dried over anhydrous magnesium sulfate, after which the solvent is removed by distillation under reduced pressure, to obtain 0.22 g of brown, oily 3-(2-amino-3-hydroxypropoxy)-5-methylamino-1,2-benzoisoxazole.

(4) To a solution of 0.19 g of 3-(2-amino-3-hydroxypropoxy)-5-methylamino-1,2-benzoisoxazole in 5 ml of ethyl acetate is added 0.26 g of di-tert-butyl dicarbonate at 20°–25° C. and they are subjected to reaction at the same temperature for five hours. Water is added to the reaction mixture, and after shaking, the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane:ethyl acetate=1:1] to obtain 0.19 g of colorless, crystalline 3-(2-tert-butoxycarbonylamino-3-hydroxypropoxy)-5-(N-methyl-N-tert-butoxycarbonylamino)-1,2-benzoisoxazole having a melting point of 109°–112° C.

(5) To a solution of 0.11 g of 3-(2-tert-butoxycarbonylamino-3-hydroxypropoxy)-5-(N-methyl-N-tert-butoxycarbonylamino)-1,2-benzoisoxazole in 5 ml of methylene chloride is added 0.10 g of chlorosulfonyl isocyanate at −45° to −40° C., and the temperature is elevated to 0° C., after which they are subjected to reaction at the same temperature for one hour. To the reaction mixture is added 10 ml of water and they are subjected to reaction at 20°–25° C. for one hour, after which the organic layer is separated. The separated organic layer is dried over anhydrous magnesium sulfate and the solvent is then removed by distillation under reduced pressure, to obtain 0.10 g of yellow, oily 3-(3-carbamoyloxy-2-tert-butoxycarbonylaminopropoxy)-5-(N-methyl-N-tert-butoxycarbonylamino)-1,2-benzoisoxazole.

(6) To a solution of 0.10 g of 3-(3-carbamoyloxy-2-tert-butoxycarbonylaminopropoxy)-5-(N-methyl-N-tert-butoxycarbonylamino)-1,2-benzoisoxazole in 5 ml of methanol is added 1.2 ml of a dioxane solution (2.2N) of hydrogen chloride at 5°–10° C., and they are subjected to reaction at 20°–25° C. overnight. The solvent is removed from the reaction mixture by distillation under reduced pressure, and the residue obtained is crystallized from 2-propanol, after which the crystals are collected by filtration to obtain 0.03 g of colorless, crystalline 3-(2-amino-3-carbamoyloxypropoxy)-5-methylamino-1,2-benzoisoxazole hydrochloride having a melting point of 179°–185° C.

IR (KBr) cm$^{-1}$: 3445, 1732, 1716, 1651, 1634, 1539, 1506

EXAMPLE 98

A solution in 2 ml of ethyl acetate of 0.17 g of brown, oily 3-(2-amino-3-carbamoyloxypropoxy)-5-n-butylamino-1,2-benzoisoxazole obtained in the same manner as in Example 97 is added to a solution of 0.07 g of oxalic acid in 4 ml of ethyl acetate, and the crystals precipitated are collected by filtration, to obtain 0.16 g of colorless, crystalline 3-(2-amino-3-carbamoyloxypropoxy)-5 -n-butylamino-1,2-benzoisoxazole oxalate having a decomposition point of 135° C.

IR (KBr) cm$^{-1}$: 3444, 2964, 1731, 1722, 1715, 1626, 1539, 1458, 1403

EXAMPLE 99

(1) To a solution of 0.61 g of 5-amino-3-(2-tert-butoxycarbonylamino-3-hydroxypropoxy)-1,2-benzoisoxazole in 18 ml of methanol are added 1.3 ml of a dioxane solution (2.2N) of hydrogen chloride and 0.49 g of 37% formalin at 20°–25° C., and then, 0.19 g of sodium cyanoborohydride is added at 15°–20° C., after which they are subjected to reaction at the same temperature for 30 minutes. Ethyl acetate and water are added to the reaction mixture and the pH is adjusted to 10 with an aqueous sodium hydroxide solution, after which the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane:ethyl acetate=3:2], to obtain 0.60 g of brown, oily 3-(2-tert-butoxycarbonylamino-3-hydroxypropoxy)-5-dimethylamino-1,2-benzoisoxazole.

(2) To a solution of 0.58 g of 3-(2-tert-butoxycarbonylamino-3-hydroxypropoxy)-5-dimethylamino-1,2-benzoisoxazole in 12 ml of methylene chloride is added 0.26 g of trichloroacetyl isocyanate at −35° to −30° C., and the temperature is elevated to 0° C., after which they are subjected to reaction at the same temperature for one hour. To the reaction mixture is added 10 ml of water, and they are subjected to reaction at 20°–25° C. for one hour, after which the organic layer is separated. The separated organic layer is dried over anhydrous magnesium sulfate and thereafter the solvent is removed by distillation under reduced pressure, to obtain 0.94 g of brown, oily 3-(3-carbamoyloxy-2-tert-butoxycarbonylaminopropoxy)-5-dimethylamino-1,2-benzoisoxazole.

(3) To a solution of 0.94 g of 3-(3-carbamoyloxy-2-tert-butoxycarbonylaminopropoxy)-5-dimethylamino-1,2-benzoisoxazole in 19 ml of methanol is added 7.5 ml of a dioxane solution (2.2N) of hydrogen chloride at 5°–10° C., and they are subjected to reaction at 20°–25° C. overnight. The solvent is removed from the reaction mixture by distillation under reduced pressure, and the residue obtained is crystallized from 2-propanol, after which the crystals are collected by filtration, to obtain 0.34 g of colorless, crystalline 3-(2-amino-3-carbamoyloxypropoxy)-5-dimethylamino-1,2-benzoisoxazole hydrochloride having a melting point of 183°–186° C.

IR (KBr) cm$^{-1}$: 3440, 1742, 1543, 1477, 1459, 1405

EXAMPLE 100

(1) To a solution of 0.24 g of 60% sodium hydride in 10 ml of N,N-dimethylformamide are dropwise added 2.0 g of 2-(2-methyl-1,3-thiazol-5-yl)-2-tritylaminoethanol, a solution of 10 ml of N,N-dimethylformamide at room temperature, and the temperature is gradually elevated to 80° C. after which 1.03 g of 3,5-dichloro-1,2-benzoisoxazole is added. They are subjected to reaction at the same temperature for one hour. After cooling, water and ethyl acetate are added, and the crystals precipitated are collected by filtration. The organic layer of the filtrate is separated, washed with a saturated saline solution and dried over anhydrous magnesium sulfate, after which the solvent is removed by distillation under reduced pressure. The crystals obtained are combined with the crystals previously collected by filtration to obtain 1.81 g of colorless, crystalline 5-chloro-3-[2-(2-methyl-1,3-thiazol-5-yl)-2-tritylaminoethoxy]-1,2-benzoisoxazole.

(2) To a solution of 1.7 g of 5-chloro-3-[2-(2-methyl-1,3-thiazol-5-yl)-2-tritylaminoethoxy]-1,2-benzoisoxazole in 17 ml of chloroform and 17 ml of methanol is added 2.05 ml of a 2-propanol solution (7.5N) of hydrogen chloride at room temperature, and they are subjected to reaction at the same temperature for two hours, after which the solvent is removed by distillation under reduced pressure. To the residue obtained is added 2-propanol, and after stirring, the crystals precipitated are collected by filtration, to obtain 0.90 g of colorless, crystalline 5-chloro-3-[2-(2-methyl-1,3-thiazol-5-yl)-2-aminoethoxy]-1,2-benzoisoxazole hydrochloride having a melting point of 212° C.

IR (KBr) cm$^{-1}$: 3445, 2898, 1540, 1515, 1479, 1359, 1319, 944, 939, 822

EXAMPLES 101 TO 109

In the same manner as in Example 100, the compounds shown in Table 16 are obtained. Incidentally, R, $R_3$, $R_4$, $R_5$ and $R_6$ in Table 16 represent the corresponding substituents of a compound represented by the following formula:

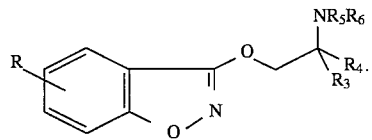

Moreover, the numeral put before each group of R in the Table indicates the substitution position.

TABLE 16

| No. | R | $R_3$ | $R_4$ | $R_5$ | $R_6$ |
|---|---|---|---|---|---|
| 101 | 5, Cl | —CH$_2$CH$_2$— | | H | H |
| 102 | 5, Cl | —(CH$_2$)$_5$— | | H | H |
| 103 | 5, Cl | H | phenyl | H | H |
| 104 | 5, Cl | H | 4-N(CH$_3$)$_2$-phenyl | H | H |
| 105 | 5, Cl | H | 4-OCH$_3$-phenyl | H | H |
| 106 | 5, Cl | H | 4-OCH$_3$-phenyl | H | H |
| 107 | 5, Cl | H | pyridyl | H | H |
| 108*$^1$ | 5, Cl | H | thienyl (S) | H | H |
| 109 | 5, Cl | H | 2-NH$_2$-thiazolyl | H | H |

*$^1$: The carbon atom to which $R_3$ and $R_4$ are bonded is in the S configuration.

Physical properties of the compounds shown in Table 16 are shown below (* indicates physical properties of hydrochloride)

No. 101: IR (KBr)* cm$^{-1}$: 3446, 2856, 1548, 1534, 1477, 1379, 1306, 988, 812, 673 Melting point*: 213.5°–215.5° C.

No. 102: IR (KBr)* cm$^{-1}$: 3444, 2947, 1539, 1479, 1481, 1359, 1318, 1258, 1122, 1006, 928, 818 Melting point*: 258.7°–259.5° C. (decomp.)

No. 103: IR (KBr)* cm$^{-1}$: 3444, 2929, 1537, 1509, 1477, 1373, 1308, 806, 700 Melting point*: 235°–238° C.

No. 104: IR (KBr)* cm$^{-1}$: 3424, 2958, 2662, 1542, 1518, 1476, 1365, 1130, 932, 827 Melting point*: 213.8°–215.8° C. (decomp.)

No. 105: IR (KBr) cm$^{-1}$: 3383, 2939, 1609, 1536, 1475, 1439, 1358, 1310, 1259, 1048, 929, 808, 700 Melting point*: 239.0°–240.9° C. (decomp.)

No. 106: IR (KBr)* cm$^{-1}$: 2962, 1614, 1538, 1520, 1478, 1436, 1366, 1258, 1183, 1030, 810, 681 Melting point*: 246°–248° C. (decomp.)

No. 107: IR (KBr)* cm$^{-1}$: 3448, 3033, 2944, 2881, 1544, 1474, 1434, 1366, 1004, 816, 687 Melting point*: 253°–255° C.

No. 108: IR (KBr)* cm$^{-1}$: 3446, 2880, 1541, 1514, 1477, 1438, 1371, 1315 Melting point*: 217.0°–220.1° C.

No. 109: IR (KBr) cm$^{-1}$: 3383, 3112, 2363, 1538, 1480, 1439, 1352, 1319, 1259 Melting point*: <194.7° C. (decomp.)

EXAMPLE 110

(1) To a solution of 2.3 g of 3-[2-amino-2-(3-methoxyphenyl)ethoxy]-5-chloro-1,2-benzoisoxazole in 20 ml of methylene chloride is dropwise added 22 ml of a methylene chloride solution (1.0M) of boron tribromide over 15 minutes with ice-cooling, and they are subjected to reaction at the same temperature for 30 minutes. Subsequently, insolubles are removed by filtration, and water and ethyl acetate are added to the filtrate. The pH is adjusted to 8.5 with a 10% aqueous sodium hydroxide solution, and after shaking, the crystals precipitated are collected by filtration. The organic layer of the filtrate is separated, and the organic layer is washed with a saturated saline solution and dried over anhydrous magnesium sulfate, after which the solvent is removed by distillation under reduced pressure. The crystals obtained are combined with the crystals previously obtained by filtration and dried, to obtain 2.0 g of colorless, crystalline 3-[2-amino-2-(3-hydroxyphenyl)ethoxy]-5-chloro-1,2-benzoisoxazole.

(2) To a solution of 0.62 g of 3-[2-amino-2-(3-hydroxyphenyl)ethoxy]-5-chloro-1,2-benzoisoxazole in 15 ml of ethanol is added 1.5 ml of a 2-propanol solution (6.5M) of hydrogen chloride at room temperature, and thereafter, the crystals precipitated are collected by filtration and then dried to obtain 0.45 g of colorless, crystalline 3-[2-amino-2-(3-hydroxyphenyl)ethoxy]-5-chloro-1,2-benzoisoxazole hydrochloride having a melting point of 240.5°–243.4° C.

IR (KBr) cm$^{-1}$: 3358, 2992, 1593, 1534, 1512, 1472, 1359, 1234, 1060, 817, 698

EXAMPLE 111

(1) To a solution of 0.7 g of 3-[2-amino-2-(3-hydroxyphenyl)ethoxy]-5-chloro-1,2-benzoisoxazole in 7 ml of N,N-dimethylformamide are added 0.307 g of triethylamine and 0.55 g of di-tert-butyl dicarbonate at room temperature, and they are subjected to reaction at the same temperature for 1.5 hours. Subsequently, water and ethyl acetate are added to adjust the pH to 3.0, and after shaking, the organic layer is separated. The separated organic layer is washed with a saturated saline solution and then dried over anhydrous magnesium sulfate, after which the solvent is removed by distillation under reduced pressure. Diisopropyl ether is added to the residue obtained and, after stirring, the crystals precipitated are collected by filtration, to obtain 0.46 g of colorless, solid 3-[2-tert-butoxycarbonylamino-2-(3-hydroxyphenyl)ethoxy]-5-chloro-1,2-benzoisoxazole.

(2) To a solution of 0.40 g of 3-[2-tert-butoxycarbonylamino-2-(3-hydroxyphenyl)ethoxy]-5-chloro-1,2-benzoisoxazole in 10 ml of methylene chloride is added 0.20 g of chlorosulfonyl isocyanate at −30° C., and thereafter, the temperature is gradually elevated to 0° C., after which 5 ml of water is added and they are subjected to reaction at the same temperature for 30 minutes. The solvent is removed by distillation under reduced pressure, water and ethyl acetate are added to the residue obtained, and after shaking, the organic layer is separated. The separated organic layer is washed with a saturated saline solution and dried over anhydrous magnesium sulfate, after which the solvent is removed by distillation under reduced pressure. The oily product obtained is dissolved in 20 ml of methanol and 20 ml of chloroform, and 3.0 ml of a 2-propanol solution (6.5M) of hydrogen chloride is added at room temperature. They are subjected to reaction at the same temperature for 18 hours, after which the solvent is removed by distillation under reduced pressure. 2-Propanol is added to the residue obtained, and after stirring, the crystals precipitated are collected by filtration to obtain 0.3 g of colorless, crystalline 3-[2-amino-2-(3-carbamoyloxyphenyl)ethoxy]-5-chloro-1, 2-benzoisoxazole hydrochloride having a melting point of 232.0°–233.5° C.

IR (KBr) cm$^{-1}$: 3447, 2921, 1742, 1609, 1540, 1477, 1361, 1235, 1002, 810

EXAMPLE 112

In the same manner as in Example 110, from 3-[2-amino-2-(4-methoxyphenyl)ethoxy]-5-chloro-1,2-benzoisoxazole, there is obtained 3-[2-amino-2-(4-hydroxyphenyl)ethoxy]-5-chloro-1,2-benzoisoxazole hydrochloride.

IR (KBr) cm$^{-1}$: 3422, 3022, 1616, 1539, 1520, 1499, 1476, 1365, 1258, 825, 812

EXAMPLE 113

In the same manner as in Example 111, from 3-[2-amino-2-(4-hydroxyphenyl)ethoxy]-5-chloro-1,2-benzoisoxazole, there is obtained 3-[2-amino-2-(4-carbamoyloxyphenyl)ethoxy]-5-chloro-1,2-benzoisoxazole hydrochloride.

EXAMPLE 114

(1) A solution of 2.86 g of 2-amino-1-pentanol in 2 ml of tetrahydrofuran is added to a suspension of 2.24 g of 60% (w/w) sodium hydride in 20 ml of tetrahydrofuran at 20°–25° C. and they are refluxed for two hours. Subsequently, under reflux, a solution of 4.3 g of 3-chloro-1,2-benzoisoxazole in 30 ml of tetrahydrofuran is added and refluxed for a further one hour. After cooling, the solvent is removed by distillation under reduced pressure. Ethyl acetate and water are added to the residue obtained, and after shaking, the organic layer is separated. The separated organic layer is washed with a saturated saline solution, dried over anhydrous magnesium sulfate, and thereafter purified by a silica gel column chromatography [eluant:chloroform:methanol=20:1], to obtain 5.38 g of oily 3-(2-aminopentyloxy)-1,2-benzoisoxazole.

(2) To 20 ml of an ethyl acetate solution of 2 g of 3-(2-aminopentyloxy)-1,2-benzoisoxazole is added 20 ml of a dioxane solution (2.2N) of hydrogen chloride, and the crystals precipitated are collected by filtration to obtain 1.05 g of colorless, crystalline 3-(2-aminopentyloxy)-1,2-benzoisoxazole hydrochloride having a melting point of 205.8°–206.5° C.

IR (KBr) cm$^{-1}$: 2962, 1614, 1542, 1445

EXAMPLES 115 TO 135

In the same manner as in Example 114, the compounds and hydrochlorides of them shown in Tables 17a to Table 17c are obtained. Incidentally, R, $R_3$, $R_4$, $R_5$ and $R_6$ in Table 17a to Table 17c represent the corresponding substituents of a compound represented by the following formula:

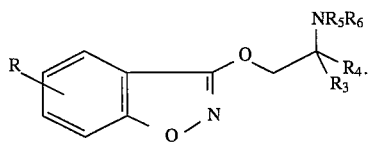

Moreover, the numeral put before each group of R in the Tables indicates the substitution position.

TABLE 17a

| No. | R | $R_3$ | $R_4$ | $R_5$ | $R_6$ |
|---|---|---|---|---|---|
| 115 | 5, Cl | H | $CH_3$ | H | H |
| 116 | 5, Cl | H | $CH_2CH_3$ | H | H |
| 117*² | 5, Cl | H | $(CH_2)_2CH_3$ | H | H |
| 118*¹ | 5, Cl | H | $(CH_2)_2CH_3$ | H | H |
| 119*² | 5, Cl | H | isopropyl | H | H |
| 120*¹ | 5, Cl | H | isobutyl | H | H |
| 121*¹ | 5, Cl | H | sec-butyl | H | H |
| 122*¹ | 5, Cl | H | tert-butyl | H | H |

*¹: The carbon atom to which $R_3$ and $R_4$ are attached is in the S configuration.
*²: The carbon atom to which $R_3$ and $R_4$ are attached is in the R configuration.

TABLE 17b

| No. | R | $R_3$ | $R_4$ | $R_5$ | $R_6$ |
|---|---|---|---|---|---|
| 123 | 5, Cl | H | benzyl | H | H |
| 124 | 5, Cl | H | $CH_2F$ | H | H |
| 125 | 5, Cl | H | $CH_2$-morpholino | H | H |
| 126 | 5, Cl | H | $CH_2OCH_3$ | H | H |

TABLE 17b-continued

| No. | R | $R_3$ | $R_4$ | $R_5$ | $R_6$ |
|---|---|---|---|---|---|
| 127 | 5, Cl | H | $CH_2SCH_3$ | H | H |
| 128 | 5, Cl | H | $CH_2CONH_2$ | H | H |
| 129 | 5, Cl | H | $CH_2CON$(piperidino) | H | H |
| 130 | 5, Cl | H | $(CH_2)_2CONH_2$ | H | H |

TABLE 17c

| No. | R | $R_3$ | $R_4$ | $R_5$ | $R_6$ |
|---|---|---|---|---|---|
| 131 | H | H | $CH_3$ | H | H |
| 132 | H | H | $CH_2CH_3$ | H | H |
| 133 | 5, Cl | H | $(CH_2)_2CH_3$ | H | H |
| 134 | 5, $CH_3$ | H | $(CH_2)_2CH_3$ | H | H |
| 135 | 5, $OCH_3$ | H | $(CH_2)_2CH_3$ | H | H |

Physical properties of the compounds shown in Table 17a to Table 17c are shown below (* indicates physical properties of hydrochloride).

No. 115: IR (KBr)* cm$^{-1}$: 3451, 2925, 1542, 1478, 1365, 810 Melting point*: 236.1°–238.1° C.

No. 116: IR (KBr)* cm$^{-1}$: 3446, 2969, 1610, 1541, 1508, 1478, 1438, 1369, 1318, 1261, 1122, 934, 812, 687, 558 Melting point*: 237.5°–238.3° C. (decomp.)

No. 117: IR (KBr) cm$^{-1}$: 2963, 1611, 1545, 1514, 1479, 1461, 1439, 1364, 1319 Melting point*: 238°–241° C.

No. 118: IR (KBr)* cm$^{-1}$: 2963, 1611, 1545, 1514, 1479, 1461, 1439, 1364, 1319 Melting point*: 242.7°–244.6° C.

No. 119: IR (KBr)* cm$^{-1}$: 3444, 3041, 2967, 2889, 1610, 1544, 1519, 1478, 1439, 1368, 1319 Melting point*: 232°–235° C.

No. 120: IR (KBr)* cm$^{-1}$: 3446, 2959, 1543, 1509, 1478, 1439, 1373, 1318, 932, 807 Melting point*: 240.0°–241.5° C. (decomp.)

No. 121: IR (KBr)* cm$^{-1}$: 3383, 2963, 1610, 1539, 1476, 1441, 1363, 1311, 1259 Melting point*: 232.8°–235.0° C. (decomp.)

No. 122: IR (KBr)* cm$^{-1}$: 3446, 2969, 1608, 1538, 1519, 1478, 1439, 1362, 1312, 1260, 935, 811, 517 Melting point*: 234.5°–236.4° C. (decomp.)

No. 123: IR (KBr)* cm$^{-1}$: 3448, 2930, 1609, 1534, 1506, 1479, 1370, 1313, 1011, 934, 820, 745, 698, 555 Melting point*: 237.6°–238.2° C.

No. 124: IR (KBr)* cm$^{-1}$: 2860, 2700, 2625, 1610, 1592, 1545, 1523, 1480, 1363, 1318, 1227, 1120, 800 Melting point*: 217.5°–218.5° C. (decomp.)

No. 125: IR (KBr) cm$^{-1}$: 3382, 2958, 2855, 2811, 1540, 1476, 1456, 1359, 1310, 1119, 867 Melting point*: 244.6°–245.4° C.

No. 126: IR (KBr)* cm$^{-1}$: 3446, 2927, 1541, 1478, 1439, 1368, 1117, 932, 810, 688, 558 Melting point*: 199°–202° C.

No. 127: IR (KBr)* cm$^{-1}$: 3446, 3052, 1542, 1502, 1479, 1439, 1356, 1319, 812 Melting point*: 203.0°–205.5° C.

No. 128: IR (KBr)* cm$^{-1}$: 3365, 3198, 2943, 1669, 1616, 1538, 1477, 1365, 1319, 1228, 805, 566 Melting point*: 209.5°–211.5° C.

No. 129: IR (KBr)* cm$^{-1}$: 3420, 2941, 1632, 1540, 1478, 1441, 1356, 1254, 1124, 1010, 932, 812, 556 Melting point*: 128°–131° C.

No. 130: IR (KBr)* cm$^{-1}$: 3446, 2956, 1743, 1543, 1478, 1438, 1204, 1112, 811 Melting point*: 199.4°–200.4° C.

No. 131: IR (KBr)* cm$^{-1}$: 3448, 2961, 1613, 1540, 1525, 1444, 1373, 1232, 748 Melting point*: 234° C.

No. 132: IR (KBr)* cm$^{-1}$: 2884, 1613, 1539, 1517, 1444 Melting point*: 221.0°–221.6° C.

No. 133: IR (KBr)* cm$^{-1}$: 2963, 1609, 1541, 1518, 1438, 1364, 1319 Melting point*: 235.8°–237.7° C.

No. 134: IR (KBr)* cm$^{-1}$: 2958, 1609, 1542, 1520, 1495, 1465, 1365, 1238, 1008, 804, 560 Melting point*: 222.0°–224.5° C. (decomp.)

No. 135: IR (KBr)* cm$^{-1}$: 3447, 2966, 2873, 1544, 1514, 1498, 1435, 1340, 1218, 1103, 807 Melting point*: 218°–221° C. (decomp.)

EXAMPLE 136

(1) To a solution of 0.67 g of 3-(2-amino-4-methoxybutoxy)-5-chloro-1,2-benzoisoxazole in 10 ml of methylene chloride is dropwise added 12 ml of a methylene chloride solution (1.0M) of boron tribromide with ice-cooling over 15 minutes, and they are subjected to reaction at the same temperature for 30 minutes. Water is added to the reaction mixture, the pH is adjusted to 8.5 with a 10% aqueous sodium hydroxide solution, and after shaking, the organic layer is separated. The aqueous layer is extracted with methylene chloride three times, and the extracts are combined with the organic layer previously separated, washed with a saturated saline solution and dried over anhydrous magnesium sulfate, after which the solvent is removed by distillation under reduced pressure. The oily product obtained is dissolved in 10 ml of methylene chloride, and 0.37 g of triethylamine and 0.66 g of di-tert-butyl dicarbonate are added thereto at room temperature, after which they are subjected to reaction at the same temperature for 18 hours. Subsequently, water is added, they are shaken, and the organic layer is separated, then washed with a saturated saline solution and dried over anhydrous magnesium sulfate. The solvent is removed by distillation under reduced pressure, and the residue obtained is purified by a column chromatography [eluant:benzene:ethyl acetate=3:1], to obtain 0.67 g of oily 3-(2-tert-butoxycarbonylamino-4-hydroxybutoxy)-5-chloro-1,2-benzoisoxazole.

IR (neat) cm$^{-1}$: 3422, 3357, 2977, 1694, 1611, 1538, 1478, 1441, 1369, 1311, 1168, 1055, 928, 809

(2) To a solution of 0.67 g of 3-(2-tert-butoxycarbonylamino-4-hydroxybutoxy)-5-chloro-1,2-benzoisoxazole in 6 ml of methylene chloride is added 0.30 g of chlorosulfonyl isocyanate at −30° C., and the temperature is gradually elevated to 0° C., after which 5 ml of water is added and they are stirred for 30 minutes. The solvent is removed by distillation under reduced pressure, water and ethyl acetate are added to the residue obtained, and after shaking, the organic layer is separated. The separated organic layer is washed with a saturated saline solution and dried over anhydrous magnesium sulfate, after which the solvent is removed by distillation under reduced pressure. The oily product obtained is dissolved in 8 ml of methanol, and thereto is added 1.5 ml of a 2-propanol solution (6.5M) of hydrogen chloride at room temperature, after which they are subjected to reaction at the same temperature for 18 hours. The crystals precipitated are collected by filtration, to obtain 0.29 g of colorless, crystalline 3-(2-amino-4-carbamoyloxybutoxy)-5-chloro-1,2-benzoisoxazole hydrochloride having a melting point of 213.5°–215.5° C.

IR (KBr) cm$^{-1}$: 3409, 3026, 1706, 1543, 1473, 1433, 1344, 1082, 822 Melting point: 213.5°–215.5° C. (decomp.)

EXAMPLE 137

To a suspension of 0.44 g of 60% (w/w) sodium hydride in 6 ml of N,N-dimethylformamide is dropwise added 15 ml of an N,N-dimethylformamide solution of 4.0 g of (R)-3-methylthio-2-tritylamino-1-propanol over 15 minutes with ice-cooling, and the temperature is gradually elevated to 80° C., after which this is added to a solution of 2.07 g of 3,5-dichloro-1,2-benzoisoxazole in 10 ml of N,N-dimethylformamide. They are subjected to reaction at the same temperature for one hour. After cooling, water and ethyl acetate are added and shaken, and the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane:ethyl acetate=20:1], to obtain 4.4 g of oily (R)-5-chloro-3-(3-methylthio-2-tritylaminopropoxy)-1,2-benzoisoxazole.

IR (KBr) cm$^{-1}$: 3448, 3057, 2921, 1610, 1539, 1486, 1475, 1439, 1358, 1283, 1258, 1028, 810, 708

EXAMPLE 138

To a solution of 2.41 g of (R)-5-chloro-3-(3-methylthio-2-tritylaminopropoxy)-1,2-benzoisoxazole in 5 ml of methanol is added 6.0 ml of a 2-propanol solution (6.5M) of hydrogen chloride at room temperature, and they are subjected to reaction at the same temperature for three hours, after which the solvent is removed by distillation under reduced pressure. Ethyl acetate is added to the residue obtained and the crystals precipitated are collected by filtration and dried, to obtain 0.72 g of colorless, crystalline (R)-3-(2-amino-3-methylthiopropoxy)-5-chloro-1,2-benzoisoxazole hydrochloride having a melting point of 195.0°–198.2° C. (decomp.).

IR (KBr) cm$^{-1}$: 3449, 2915, 1543, 1500, 1478, 1439, 1365, 1318

EXAMPLE 139

To a solution of 0.54 g of (R)-3-(2-amino-3-methylthiopropoxy)-5-chloro-1,2-benzoisoxazole in 5 ml of methylene chloride is added 0.43 g of m-chloroperbenzoic acid with ice-cooling, and they are subjected to reaction at the same temperature for 30 minutes, after which 0.21 g of m-chloroperbenzoic acid is added and they are subjected to reaction for a further 30 minutes at the same temperature. After completion of the reaction, a saturated aqueous sodium hydrogencarbonate solution is added and shaken, after which the organic layer is separated. The separated organic layer is washed with a saturated saline solution and dried over anhydrous magnesium sulfate, and the solvent is removed by distillation under reduced pressure. The residue obtained is purified by a column chromatography [eluant:chloroform:methanol=20:1], to obtain 0.14 g of oily (R)-3-(2-amino-3-methanesulfinylpropoxy)-5-chloro-1,2-benzoisoxazole (Compound No. 139-1) and 0.38 g of oily (R)-3-(2-amino-3-methanesulfonylpropoxy)-5-chloro-1,2-benzoisoxazole (Compound No. 139-2).

No. 139-1: IR (neat) cm$^{-1}$: 3373, 1610, 1539, 1477, 1440, 1364, 1311, 1260, 1020

No. 139-2: IR (neat) cm$^{-1}$: 3379, 1540, 1477, 1360, 1300, 1138

EXAMPLE 140

To a solution of 0.14 g of (R)-3-(2-amino-3-methanesulfinylpropoxy)-5-chloro-1,2-benzoisoxazole in 2 ml of methylene chloride is added 0.4 ml of a 2-propanol solution (6.5M) of hydrogen chloride, and the crystals precipitated are collected by filtration, to obtain 0.07 g of colorless, crystalline (R)-3-(2-amino-3-methanesulfinylpropoxy)-5-chloro-1,2-benzoisoxazole hydrochloride.

IR (KBr) cm$^{-1}$: 3420, 2914, 1610, 1538, 1479, 1358, 1260, 1015, 934, 807, 690, 555

EXAMPLE 141

To a solution of 0.38 g of (R)-3-(2-amino-3-methanesulfonylpropoxy)-5-chloro-1,2-benzoisoxazole in 4 ml of methylene chloride is added 1 ml of a 2-propanol solution (6.5M) of hydrogen chloride, and the crystals precipitated are collected by filtration, to obtain 0.22 g of colorless, crystalline (R)-3-(2-amino-3-methanesulfonylpropoxy)-5-chloro-1,2-benzoisoxazole hydrochloride having a melting point of 189.9°–192.5° C. (decomp.).

IR (KBr) cm$^{-1}$: 3564, 2983, 1611, 1547, 1476, 1309, 1142, 1012, 810, 535

EXAMPLE 142

A solution of 2.0 g of 2-tritylamino-3-(1-trityl-4-imidazolyl)-1-propanol in 10 ml of N,N-dimethylformamide is dropwise added to a suspension of 0.14 g of 60% (w/w) sodium hydride in 15 ml of N,N-dimethylformamide at room temperature over 15 minutes, and the temperature is then elevated gradually to 80° C., after which this is added to a solution of 0.6 g of 3,5-dichloro-1,2-benzoisoxazole in 10 ml of N,N-dimethylformamide. They are subjected to reaction at the same temperature for six hours. After cooling, water and ethyl acetate are added and shaken, and the organic layer is separated. The separated organic layer is washed with a saturated saline solution and dried over anhydrous magnesium sulfate, after which the solvent is removed by distillation under reduced pressure. The residue obtained is purified by a column chromatography [eluant:n-hexane:ethyl acetate=3:1], to obtain 1.12 g of colorless, crystalline 5-chloro-3-[2-tritylamino-3-(1-trityl-4-imidazolyl)propoxy]-1,2-benzoisoxazole having a melting point of 113.4°–114.7° C.

IR (KBr) cm$^{-1}$: 3445, 3057, 2967, 1596, 1538, 1490, 1474, 1446, 1364, 1310, 1155, 747, 702

EXAMPLE 143

To a solution of 0.91 g of 5-chloro-3-[2-tritylamino-3-(1-trityl-4-imidazolyl)propoxy]-1,2-benzoisoxazole in 2 ml of methylene chloride is added 2.2 ml of a 2-propanol solution (6.5M) of hydrogen chloride at room temperature, and they are subjected to reaction at the same temperature for 24 hours, after which the solvent is removed by distillation under reduced pressure. Diisopropyl ether is added to the residue obtained and the crystals precipitated are collected by filtration, to obtain 0.4 g of colorless, crystalline 3-[2-amino-3-(4-imidazolyl)propoxy]-5-chloro-1,2-benzoisoxazole dihydrochloride having a melting point of 246.0°–248.4° C. (decomp.).

IR (KBr) cm$^{-1}$: 3070, 2896, 2612, 1622, 1546, 1475, 1431, 1362, 1316, 1000, 809, 689, 629, 555

EXAMPLE 144

(1) To a solution of 0.24 g of 3-[2-amino-3-(4-imidazolyl)propoxy]-5-chloro-1,2-benzoisoxazole dihydrochloride in 5 ml of tetrahydrofuran are added 0.14 g of triethylamine and 0.17 g of di-tert-butyl dicarbonate at room temperature, and they are subjected to reaction at the same temperature for three hours. Water and ethyl acetate are added to the reaction mixture and shaken, and the organic layer is separated. The separated organic layer is washed with a saturated saline solution and dried over anhydrous magnesium sulfate. The solvent is removed by distillation under reduced pressure, and the residue obtained is purified by a column chromatography [eluant:chloroform:methanol= 10:1], to obtain 0.15 g of yellow, solid 3-[2-tert-butoxycarbonylamino-3-(4-imidazolyl)propoxy]-5-chloro-1,2-benzoisoxazole.

IR (KBr) cm$^{-1}$: 3321, 3104, 2977, 2855, 1698, 1539, 1478, 1365, 1279, 1251, 1174, 1055, 938, 816

(2) To a solution of 0.12 g of 3-[2-tert-butoxycarbonylamino-3-(4-imidazolyl)propoxy]-5-chloro-1,2-benzoisoxazole in 3 ml of pyridine is added 0.05 g of dimethylcarbamoyl chloride at room temperature, and they are subjected to reaction at 50° C. for two hours. After cooling, water and ethyl acetate are added and shaken, and the organic layer is separated. The separated organic layer is washed with a saturated saline solution and dried over anhydrous magnesium sulfate, and the solvent is removed by distillation under reduced pressure, to obtain 0.2 g of oily 3-[2-tert-butoxycarbonylamino-3-(1-dimethylcarbamoyl-4-imidazolyl)propoxy]-5-chloro-1,2-benzoisoxazole.

IR (KBr) cm$^{-1}$: 3366, 2984, 1689, 1542, 1519, 1478, 1405, 1258, 1168, 1062, 931

(3) To a solution of 0.2 g of 3-[2-tert-butoxycarbonylamino-3-(1-dimethylcarbamoyl-4-imidazolyl)propoxy]-5-chloro-1,2-benzoisoxazole in 2 ml of methanol is added 1.2 ml of a 2-propanol solution (6.5M) of hydrogen chloride at room temperature and they are subjected to reaction at the same temperature for ten hours, after which the solvent is removed by distillation under reduced pressure. Diisopropyl ether is added to the residue obtained and the crystals precipitated are collected by filtration, to obtain 0.1 g of pale brown, crystalline 3-[2-amino-3-(1-dimethylcarbamoyl-4-imidazolyl)propoxy]-5-chloro-1,2-benzoisoxazole hydrochloride having a melting point of 167.0°–169.5° C. (decomp.).

IR (KBr) cm$^{-1}$: 3384, 2997, 1725, 1542, 1478, 1362, 1174, 1010, 824

EXAMPLE 145

To a solution of 0.5 g of 2-tert-butoxycarbonylamino-3-(3-benzenesulfonyloxyisoxazol-5-yl)-1-propanol in 5 ml of tetrahydrofuran are added 0.21 g of 5-chloro-3-hydroxy-1,2-benzoisoxazole, 0.43 g of triphenylphosphine and 0.28 g of diethyl azodicarboxylate with ice-cooling, and they are subjected to reaction at room temperature for 24 hours. Thereafter, the solvent is removed by distillation under reduced pressure. The residue obtained is purified by a column chromatography [eluant:n-hexane:ethyl acetate= 4:1], to obtain 0.5 g of oily 3-[2-tert-butoxycarbonylamino-3-(3-benzenesulfonyloxy-5-isoxazolyl)propoxy]-5-chloro-1,2-benzoisoxazole.

IR (KBr) cm$^{-1}$: 3420, 2980, 1716, 1609, 1540, 1477, 1435, 1368, 1196, 1025, 754, 582

EXAMPLE 146

To a solution of 1.0 g of 3-tert-butoxycarbonylamino-4-hydroxybutyronitrile in 15 ml of tetrahydrofuran are added 0.85 g of 5-chloro-3-hydroxy-1,2-benzoisoxazole, 1.71 g of triphenylphosphine and 1.14 g of diethyl azodicarboxylate with ice-cooling, and they are subjected to reaction at room temperature for 24 hours. Thereafter, the solvent is removed by distillation under reduced pressure. The residue obtained is purified by a column chromatography [eluant:n-hexane:ethyl acetate=5:1], to obtain 1.29 g of 3-(2-tert-butoxycarbonylamino-3-cyanopropoxy)-5-chloro-1,2-benzoisoxazole having a melting point of 147.2°–147.9° C.

IR (KBr) cm$^{-1}$: 3312, 2973, 2245, 1715, 1539, 1478, 1361, 1249, 1156

EXAMPLE 147

To a suspension of 1.0 g of 3-(2-tert-butoxycarbonylamino-3-cyanopropoxy)-5-chloro-1,2-benzoisoxazole in 15 ml of methanol is added 7.8 ml of a 2-propanol solution (6.5M) of hydrogen chloride at room temperature, and they are subjected to reaction at the same temperature for seven hours. Thereafter, the solvent is removed by distillation under reduced pressure. To the residue obtained is added diisopropyl ether, and the crystals precipitated are collected by filtration, to obtain 0.78 g of colorless, crystalline 3-(2-amino-3-cyanopropoxy)-5-chloro-1,2-benzoisoxazole hydrochloride having a melting point of 188.8°–190.9° C. (decomp.).

IR (KBr) cm$^{-1}$: 3420, 2892, 2361, 1610, 1539, 1478, 1338, 1260, 1124, 807

EXAMPLE 148

To a solution of 0.5 g of 3-(2-aminopentyloxy)-5-chloro-1,2-benzoisoxazole in 5 ml of methanol is added 5 ml of 37% formalin, and then, 0.16 g of sodium cyanoborohydride is added with ice-cooling, and they are subjected to reaction at room temperature for 24 hours, after which 2N hydrochloric acid is added to adjust the pH to 1.5 and then stirring is effected for a further 30 minutes. Ethyl acetate is added to the reaction mixture, and the pH is adjusted to 9.5 with a 10% (w/w) aqueous sodium hydroxide solution, after which the organic layer is separated. The organic layer separated is washed with a saturated saline solution and dried over anhydrous magnesium sulfate, after which the solvent is removed by distillation under reduced pressure. The residue obtained is purified by a column chromatography [eluant:chloroform:methanol=20:1] and thereafter this is dissolved in ethyl acetate. Thereto is added 5 ml of a dioxane solution (2.2N) of hydrogen chloride, and the crystals precipitated are collected by filtration, to obtain 0.17 g of colorless, crystalline 5-chloro-3-(2-dimethylaminopentyloxy)-1,2-benzoisoxazole hydrochloride having a melting point of 137.1°–137.7° C.

IR (KBr) cm$^{-1}$: 2966, 2630, 2442, 1613, 1542, 1471, 1449, 1371, 1239, 1160, 974, 926, 755, 652

EXAMPLE 149

To a solution of 1 g of 3-(2-aminopentyloxy)-5-chloro-1,2-benzoisoxazole in 10 ml of methylene chloride is added 0.42 g of acetic formic anhydride with ice-cooling, and they are subjected to reaction at room temperature for one hour. The solvent is removed by distillation under reduced pressure, and water and ethyl acetate are added to the residue obtained, and the pH is adjusted to 8 with a 20% (w/w) aqueous sodium hydroxide solution. After shaking, the organic layer is separated. The separated organic layer is washed with a saturated saline solution and dried over anhydrous magnesium sulfate, after which the solvent is removed by distillation under reduced pressure, to obtain 1.1 g of colorless, crystalline 5-chloro-3-(2-formylaminopentyloxy)-1,2-benzoisoxazole having a melting point of 107.2°–108.3° C.

IR (KBr) cm$^{-1}$: 3261, 3070, 2960, 2925, 2876, 1661, 1615, 1542, 1448, 1388, 1372, 1238, 1163, 1109, 988, 924, 746, 655, 577

EXAMPLE 150

To a solution of 1 g of 5-chloro-3-(2-formylaminopentyloxy)-1,2-benzoisoxazole in 10 ml of tetrahydrofuran is dropwise added 10.1 ml of a tetrahydrofuran solution (1.0M) of diborane with ice-cooling over ten minutes, and they are further subjected to reaction at room temperature for one hour. Subsequently, 5 ml of methanol is added with ice-cooling, and thereafter, 10 ml of 6N hydrochloric acid is added thereto, and after stirring for one hour, the solvent is removed by distillation under reduced pressure. Ethyl acetate and water are added to the residue obtained, the pH is adjusted to 8 with a 10% (w/w) aqueous sodium hydroxide solution, and the organic layer is separated. The separated organic layer is washed with a saturated saline solution, dried over anhydrous magnesium sulfate, and thereafter concentrated to about 20 ml under reduced pressure. Thereto is added 5 ml of a dioxane solution (2.2N) of hydrogen chloride, and the crystals precipitated are collected by filtration, to obtain 0.6 g of colorless, crystalline 5-chloro-3-(2-methylaminopentyloxy)-1,2-benzoisoxazole hydrochloride having a melting point of 152.9°–154.8° C.

IR (KBr) cm$^{-1}$: 2942, 2740, 1612, 1538, 1448, 1381, 1234, 1158, 997, 930, 777

EXAMPLE 151

(1) To a suspension of 0.43 g of 60% (w/w) sodium hydride in 15 ml of tetrahydrofuran is added a solution of 0.80 g of 2-amino-2-methyl-1-propanol in 20 ml of tetrahydrofuran at 20°–25° C., and they are refluxed for two hours. To the reaction mixture is added a solution of 2.36 g of 3,5-dichloro-1,2-benzoisoxazole in 20 ml of tetrahydrofuran under reflux, and they are refluxed for a further one hour. After cooling, the solvent is removed by distillation under reduced pressure, and ethyl acetate and water are added to the residue obtained, and after shaking, the organic layer is separated. The separated organic layer is washed with a saturated saline solution, dried over anhydrous magnesium sulfate and then purified by a column chromatography [eluant:chloroform:methanol=20:1], to obtain 1.59 g of oily 3-(2-amino-2-methylpropoxy)-5-chloro-1,2-benzoisoxazole.

(2) To 20 ml of a 2-propanol solution of 1.59 of 3-(2-amino-2-methylpropoxy)-5-chloro-1,2-benzoisoxazole is added 20 ml of a dioxane solution (7.5N) of hydrogen chloride, and the crystals precipitated are collected by filtration, to obtain 1.62 g of colorless, crystalline 3-(2-amino-2-methylpropoxy)-5-chloro-1,2-benzoisoxazole hydrochloride having a melting point of 245.0°–246.0° C.

IR (KBr) cm$^{-1}$: 3446, 2901, 2677, 2578, 1537, 1476, 1385, 1361, 813, 556

EXAMPLE 152

(1) To a solution of 0.5 g of 3-[2-tert-butoxycarbonylamino-3-(3-benzenesulfonyloxy-5-isoxazolyl)propoxy]-5-chloro-1,2-benzoisoxazole in 4 ml of tetrahydrofuran is added 2.5 ml of a methanol solution (6N) of ammonia at room temperature, and they are subjected to reaction at the same temperature for 16 hours. Water and ethyl acetate are added to the reaction mixture, 1N hydrochloric acid is thereafter added to adjust the pH to 2, and after shaking, the organic layer is separated. The separated organic layer is washed with a saturated saline solution and dried over anhydrous magnesium sulfate, after which the solvent is removed by distillation under reduced pressure, to obtain 0.38 g of 3-[2-tert-butoxycarbonylamino-3-(3-hydroxy-5-isoxazolyl)propoxy]-5-chloro-1,2-benzoisoxazole having a melting point of 158.8°–160.7° C.

IR (KBr) cm$^{-1}$: 3358, 2981, 1688, 1621, 1532, 1477, 1368, 1165, 1064, 807, 690

(2) To a solution of 0.38 g of 3-[2-tert-butoxycarbonylamino-3-(3-hydroxy-5-isoxazolyl)propoxy]-5-chloro-1,2-benzoisoxazole in 2 ml of methanol is added 1.2 ml of a 2-propanol solution (6.5M) of hydrogen chloride at room temperature, and they are subjected to reaction at the same temperature for six hours, after which the solvent is removed by distillation under reduced pressure. Ethyl acetate is added to the residue obtained and the crystals precipitated are collected by filtration, to obtain 0.22 g of pale yellow, crystalline 3-[2-amino-3-(3-hydroxy-5-isoxazolyl)propoxy]-5-chloro-1,2-benzoisoxazole hydrochloride having a melting point of 188.5°–193.5° C. (decomp.).

IR (KBr) cm$^{-1}$: 3422, 3055, 2932, 1628, 1542, 1479, 1358, 1317, 810

EXAMPLE 153

In the same manner as in Example 137, (R)-5-chloro-3-(3-methylthio-2-tritylaminobutoxy)-1,2-benzoisoxazole is obtained, and further, in the same manner as in Example 138, its hydrochloride is obtained.

IR (KBr) cm$^{-1}$: 2884, 2821, 1611, 1546, 1497, 1446, 1389, 1373, 1228, 1164, 1006, 920, 760 Melting point: 157.0°–157.9° C.

EXAMPLE 154

In the same manner as in Example 100, 3-[2-amino-2-(2-methyl-1,3-thiazol-5-yl)ethoxy]-1,2-benzoisoxazole hydrochloride is obtained.

IR (KBr) cm$^{-1}$: 3412, 2852, 1612, 1541, 1498, 1446, 1364, 1234, 1160, 1107, 928, 750, 650 Melting point: 174.0°–176.0° C.

EXAMPLE 155

In the same manner as in Example 114, (S)-3-(2-amino-3-methylbutoxy)-1,2-benzoisoxazole hydrochloride is obtained.

IR (KBr) cm$^{-1}$: 3446, 2968, 1614, 1542, 1518, 1445, 1376, 1235, 1157, 924, 748, 652 Melting point: 218°–219° C. (decomp.)

EXAMPLE 156

In the same manner as in Example 151, 3-(2-amino-2-methylpropoxy)-1,2-benzoisoxazole hydrochloride is obtained.

IR (KBr) cm$^{-1}$: 3423, 2894, 2812, 2588, 1613, 1537, 1496, 1446, 1396, 1376, 1235, 1193, 1109, 1022, 927, 757, 654 Melting point: 220.2°–221.0° C.

EXAMPLE 157

To a solution of 0.8 g of 5-chloro-3-(2-tert-butoxycarbonylamino-3-hydroxypropoxy)-1,2-benzoisoxazole in 8 ml of N,N-dimethylformamide are added 1.6 ml of triethylamine and 0.51 g of methyl isothiocyanate at room temperature, and they are subjected to reaction at 110° C. for four hours. After cooling, water and ethyl acetate are added to the reaction mixture, they are shaken and the organic layer is separated. The separated organic layer is washed with a saturated saline solution and dried over anhydrous magnesium sulfate, after which the solvent is removed by distillation under reduced pressure. The residue obtained is purified by a silica gel column chromatography [eluant:toluene:ethyl acetate=5:1], to obtain 0.4 g of brown, solid 5-chloro-3-(2-tert-butoxy carbonylamino-3-methylthiocarbamoyloxypropoxy)-1,2-benzoisoxazole.

IR (KBr) cm$^{-1}$: 3308, 2927, 1692, 1545, 1480, 1455, 1367, 1209, 1164, 1102, 1072, 817, 669

EXAMPLE 158

To a solution of 0.4 g of 5-chloro-3-(2-tert-butoxycarbonylamino-3-methylthiocarbamoyloxypropoxy)-1,2-benzoisoxazole in 10 ml of methanol is added 5 ml of a dioxane solution (3.2N) of hydrogen chloride at room temperature, and they are subjected to reaction at the same temperature for three hours, after which the solvent is removed by distillation under reduced pressure. To the residue obtained is added 3 ml of 2-propanol, and the crystals precipitated are collected by filtration, to obtain 0.22 g of pale yellow, crystalline 3-(2-amino-3-methylthiocarbamoyloxypropoxy)-5-chloro-1,2-benzoisoxazole hydrochloride having a melting point of 198.8°–199.2° C. (decomp.).

IR (KBr) cm$^{-1}$: 3342, 3219, 2938, 1540, 1477, 1374, 1200, 1156, 1065, 1007, 812

EXAMPLE 159

To a solution of 0.378 ml of chlorosulfonyl isocyanate in 5 ml of tetrahydrofuran is dropwise added 0.78 ml of a tetrahydrofuran-water mixture (9:1 v/v) at −10° C. over five minutes, and the temperature is gradually elevated to 15° C. To this mixture are dropwise added at the same temperature 0.61 ml of triethylamine and a solution of 1.0 g of 5-chloro-3-(2-tert-butoxycarbonylamino- 3-hydroxypropoxy)-1,2-benzoisoxazole in 10 ml of tetrahydrofuran over ten minutes, after which they are subjected to reaction at room temperature for two hours. Water and ethyl acetate are added to the reaction mixture, they are shaken and the organic layer is separated. The separated organic layer is washed with a saturated saline solution and dried over anhydrous magnesium sulfate, after which the solvent is removed by distillation under reduced pressure. The residue obtained is purified by a silica gel column chromatography [eluant:toluene:ethyl acetate=5:1], to obtain 1.0 g of oily 5-chloro-3-(2-tert-butoxycarbonylamino-3-sulfamoyloxypropoxy)-1,2-benzoisoxazole.

IR (KBr) cm$^{-1}$: 3380, 2980, 1696, 1541, 1478, 1368, 1312, 1258, 1183, 934, 814, 556

EXAMPLE 160

To a solution of 0.4 g of 5-chloro-3-(2-tert-butoxycarbonylamino-3-sulfamoyloxypropoxy)-1,2-benzoisoxazole in 10 ml of methanol is added 5 ml of a dioxane solution (3.2N) of hydrogen chloride at room temperature and they are subjected to reaction at the same temperature for 24 hours, after which the solvent is removed by distillation under reduced pressure. To the residue obtained is added 10 ml of ethyl acetate, and the crystals precipitated are collected by filtration, to obtain 0.24 g of colorless, crystalline 3-(2-amino-3-sulfamoyloxypropoxy)-5-chloro-1,2-benzoisoxazole hydrochloride having a melting point of 150.5°–152.5° C. (decomp.).

IR (KBr) cm$^{-1}$: 3421, 2934, 1540, 1481, 1382, 1184, 981, 818, 546

EXAMPLE 161

To a solution of 0.30 g of 3-[2-tert-butoxycarbonylamino-3-(3-pyridyloxy)propoxy]-1,2-benzoisoxazole in 5 ml of methanol is added 1 ml of a dioxane solution (3.2N) of hydrogen chloride at room temperature, and they are subjected to reaction at the same temperature for two hours, after which the crystals precipitated are collected by filtration, to obtain 0.24 g of colorless, crystalline 3-[2-amino-3-(3-pyridyloxy)propoxy]-1,2-benzoisoxazole dihydrochloride having a melting point of 216.8°–218.9° C. (decomp.).

IR (KBr) cm$^{-1}$: 3405, 3014, 2935, 1611, 1560, 1536, 1475, 1442, 1390, 1376, 1305, 1234, 1002, 761

EXAMPLES 162 TO 163

In the same manner as in Example 16 and Example 161, the following compounds are obtained:

No. 162: 3-(2-amino-3-phenyloxypropoxy)-1,2-benzoisoxazole hydrochloride

IR (KBr) cm$^{-1}$: 3448, 2940, 1614, 1600, 1508, 1496, 1443, 1240, 1162, 1019, 759 Melting point: 210.0°–212.5° C. (decomp.)

No. 163: 3-[2-amino-3-(4-chlorophenyloxy)propoxy]-5-chloro-1,2-benzoisoxazole hydrochloride IR (KBr) cm$^{-1}$: 3446, 2892, 1597, 1540, 1492, 1243, 1008, 825 Melting point: 214.5°–216.5° C.

EXAMPLES 164 TO 166

In the same manner as in Reference Example 37, Example 17 and/or Example 47, the following compounds are obtained:

No. 164: (R)-3-(2-amino-3-carbamoyloxypropoxy)-1,2-benzoisoxazole hydrochloride

IR (KBr) cm$^{-1}$: 3444, 1702, 1616, 1542, 1449, 1369, 1316, 1237, 1106, 756 Melting point: 221.9°–223.1° C. (decomp.)

No. 165: (S)-3-(2-amino-3-carbamoyloxypropoxy)-1,2-benzoisoxazole hydrochloride

IR (KBr) cm$^{-1}$: 3444, 1702, 1616, 1542, 1449, 1369, 1316, 1237, 1106, 756 Melting point: 217.9°–218.7° C. (decomp.)

No. 166: 3-(2-amino-3-carbamoyloxypropoxy)-6-methyl-1,2-benzoisoxazole hydrochloride IR (KBr) cm$^{-1}$: 3426, 2957, 1713, 1532, 1367, 1316, 1097, 803, 648 Melting point: 230°–231° C. (decomp.)

EXAMPLE 167

In the same manner as in Example 1 (1), 3-(2-amino-3-hydroxypropoxy)-1,2-benzoisoxazole hydrochloride is obtained.

IR (KBr) cm$^{-1}$: 3376, 3034, 1612, 1538, 1446, 1393, 1232, 1155, 756 Melting point: 212°–213° C. (decomp.)

EXAMPLE 168

In the same manner as in Example 146 and Example 147, 3-(2-amino-3-ureidopropoxy)-1,2-benzoisoxazole hydrochloride is obtained.

IR (KBr) cm$^{-1}$: 3340, 2974, 1663, 1610, 1540, 1478, 1358, 1316, 1260, 1122, 1026, 932, 808, 556

EXAMPLE 169

In the same manner as in Example 39, 3-(2-amino-3-methoxypropoxy)-1,2-benzoisoxazole hydrochloride is obtained.

IR (KBr) cm$^{-1}$: 3447, 2932, 1616, 1548, 1448, 1389, 1105, 1002, 752 Melting point: 187°–190° C. (decomp.)

EXAMPLE 170

In the same manner as in Example 89, 3-(3-carbamoyloxy-2-dimethylaminopropoxy)-1,2-benzoisoxazole hydrochloride is obtained.

EXAMPLE 171

In the same manner as in Example 93, 3-(3-carbamoyloxy-2-methylaminopropoxy)-1,2-benzoisoxazole hydrochloride is obtained.

IR (KBr) cm$^{-1}$: 3418, 3002, 1732, 1615, 1540, 1440, 1353, 1234, 1078, 924, 757, 651 Melting point: 114°–115° C. (decomp.)

EXAMPLES 172 TO 179

In the same manner as in Example 100, hydrochlorides of the compounds shown in Table 18 are obtained. Incidentally, R, $R_3$, $R_4$, $R_5$ and $R_6$ in Table 18 represent the corresponding substituents of a compound represented by the following formula:

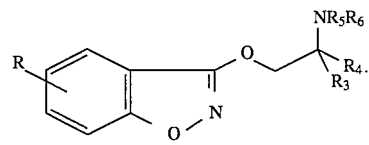

TABLE 18

| No. | R | $R_3$ | $R_4$ | $R_5$ | $R_6$ |
|---|---|---|---|---|---|
| 172 | H | H | ![thiophene-2-yl] | H | H |
| 173 | H | H | ![thiophene-3-yl] | H | H |
| 174 | H | H | ![furan-2-yl] | H | H |
| 175 | H | H | ![thiazol-2-yl] | H | H |

TABLE 18-continued

| No. | R | $R_3$ | $R_4$ | $R_5$ | $R_6$ |
|---|---|---|---|---|---|
| 176 | H | H |  | H | H |
| 177 | H | H |  | H | H |
| 178 | H | H |  | H | H |
| 179 | H | H |  | H | H |

Physical properties of the compounds shown in Table 18 are shown below (* indicates physical properties of dihydrochloride).

No. 172: IR (KBr) cm$^{-1}$: 2925, 1610, 1540, 1513, 1444, 1388, 1234, 1163, 1001, 922, 759, 727 Melting point: 230°–231° C.

No. 173: IR (KBr) cm$^{-1}$: 3418, 2885, 1614, 1539, 1446, 1361, 1234, 1162, 1003, 929, 753 Melting point: 214°–215° C.

No. 174: IR (KBr) cm$^{-1}$: 3448, 2909, 1616, 1544, 1446, 1374, 1234, 1164, 926, 751 Melting point: 202°–203° C.

No. 175: IR (KBr) cm$^{-1}$: 3445, 3090, 3024, 2923, 2794, 2696, 1614, 1546, 1449, 1377, 1230, 1161, 1006, 758 Melting point: 159°–160° C.

No. 176: IR (KBr) cm$^{-1}$: 3446, 3114, 2934, 1614, 1539, 1443, 1398, 1236, 927, 754, 705 Melting point: 231°–232° C.

No. 177: IR (KBr)* cm$^{-1}$: 3448, 3060, 2852, 1614, 1546, 1451, 1379, 1235, 1159, 1006, 756 Melting point: 189°–191° C.

No. 178: IR (KBr)* cm$^{-1}$: 3413, 3039, 2893, 1615, 1547, 1450, 1384, 1233, 1160, 1006, 923, 757 Melting point: 252°–253° C.

No. 179: IR (KBr)* cm$^{-1}$: 3414, 3016, 1618, 1546, 1450, 1380, 1231, 1163, 1007, 756 Melting point: 200°–202° C.

INDUSTRIAL APPLICABILITY

The compound of this invention has excellent cerebral hypoxia-protecting action, action of the prolongation of life of cerebral ischemic animal and neurological symptom relieving action as well as anti-convulsive action, is weak in central nervous system depressant action and high in safety, and hence, is effective for treating various diseases such as cerebral circulatory disorder in the chronic phase, head injury sequelae and epilepsy.

We claim:

1. A 1,2-benzoisoxazole compound represented by the following general formula or a salt thereof:

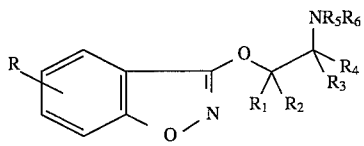

wherein R represents at least one member selected from hydrogen atom, halogen atoms, nitro group, cyano group, hydroxyl group, and substituted or unsubstituted lower alkyl, lower alkenyl, lower alkynyl, aralkyl, aryl, lower alkyloxy, cycloalkyl, aralkyloxy, aryloxy, amino, lower acyl, arylcarbonyl, lower alkanesulfonyl, arenesulfonyl, lower alkylthio, carbamoyl, heterocyclic, lower alkylene and lower alkenylene groups; $R_1$ and $R_2$, which may be the same or different, represent hydrogen atoms or substituted or unsubstituted lower alkyl groups; $R_3$ represents a hydrogen atom or a substituted or unsubstituted lower alkyl, aryl, aralkyl or heterocyclic group; $R_4$ represents a substituted or unsubstituted lower alkyl, aryl or heterocyclic group, or alternatively $R_3$ and $R_4$, when taken together, represent a lower alkylene group; $R_5$ and $R_6$, which may be the same or different, represent hydrogen atoms or substituted or unsubstituted lower alkyl, lower alkenyl, lower alkynyl, lower acyl, lower alkyloxycarbonyl or aralkyl groups.

2. A 1,2-benzoisoxazole compound or its salt according to claim 1, wherein $R_3$ is a hydrogen atom or a substituted or unsubstituted lower alkyl group and $R_4$ is a substituted or unsubstituted lower alkyl group represented by the formula:

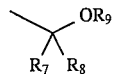

wherein $R_7$ and $R_8$ represent hydrogen atoms or substituted or unsubstituted lower alkyl groups and $R_9$ represents a substituted or unsubstituted lower alkyl, lower alkenyl, lower alkynyl, cycloalkyl, aralkyl or carbamoyl group.

3. A 1,2-benzoisoxazole compound or its salt according to claim 1, wherein R is a hydrogen atom, a halogen atom or a substituted or unsubstituted lower alkyl, lower alkyloxy, aralkyl or aralkyloxy group; $R_1$ and $R_2$ are hydrogen atoms; $R_3$ is a hydrogen atom or a substituted or unsubstituted lower alkyl, aryl, aralkyl or heterocyclic group; $R_4$ is a substituted or unsubstituted aryl or heterocyclic group or alternatively $R_3$ and $R_4$, when taken together, is a lower alkylene group; and $R_5$ and $R_6$, which may be the same or different, are hydrogen atoms or substituted or unsubstituted lower alkyl, lower acyl, lower alkyloxycarbonyl or aralkyl groups.

4. A 1,2-benzoisoxazole compound or its salt according to claim 1, wherein R is a hydrogen atom, a halogen atom or a substituted or unsubstituted lower alkyl, lower alkyloxy, aralkyl or aralkyloxy group; $R_1$ and $R_2$ are hydrogen atoms; $R_3$ is a hydrogen atom or a substituted or unsubstituted lower alkyl group; and $R_4$ is a substituted or unsubstituted lower alkyl group; and $R_5$ and $R_6$ are hydrogen atoms or substituted or unsubstituted lower alkyl, lower acyl, lower alkyloxycarbonyl or aralkyl groups.

5. A 1,2-benzoisoxazole compound or its salt according to claim 1, wherein R is a hydrogen atom, a halogen atom, a nitro group, a cyano group, a hydroxyl group or a substituted or unsubstituted lower alkyl, lower alkenyl, aryl, lower alkyloxy, aralkyloxy, aryloxy, amino, arylcarbonyl, arenesulfonyl, lower alkylthio, heterocyclic or lower alkenylene group.

6. A 1,2-benzoisoxazole compound or its salt according to claim 5, wherein the substituents of the substituted or unsubstituted lower alkyl, lower alkenyl, lower alkyloxy, aralkyloxy, arylcarbonyl, arenesulfonyl, lower alkylthio, heterocyclic and lower alkenylene groups for R are at least one group selected from halogen atoms and lower alkyloxy groups; the substituents of the substituted or unsubstituted aryl and aryloxy groups for R are at least one group selected from halogen atoms and nitro group; and the substituents of the substituted or unsubstituted amino group for R are at least one group selected from lower alkyl groups, lower acyl groups, arylcarbonyl groups and lower alkyloxycarbonyl groups.

7. A 1,2-benzoisoxazole compound or its salt according to claim 5, wherein $R_3$ is a hydrogen atom or a lower alkyl group.

8. A 1,2-benzoisoxazole compound or its salt according to claim 7, wherein $R_1$ and $R_2$ are hydrogen atoms or lower alkyl groups.

9. A 1,2-benzoisoxazole compound or its salt according to claim 8, wherein $R_5$ or $R_6$ is hydrogen atom, lower alkyl group, lower acyl group, lower alkyloxycarbonyl group or substituted or unsubstituted aralkyl group.

10. A 1,2-benzoisoxazole compound or its salt according to claim 9, wherein $R_5$ or $R_6$ is aralkyl group which may be substituted by a hydroxyl group or a lower alkyl group.

11. A 1,2-benzoisoxazole compound or its salt according to claim 9, wherein $R_4$ is a lower alkyl group which may be substituted by a halogen atom, a hydroxyl group, a lower alkyloxy group, a lower alkylthio group, a lower alkanesulfinyl group, a lower alkanesulfonyl group, a carbamoyl group, a carbamoyloxy group, a heterocyclic group (which may be substituted by a hydroxyl group, a di-lower alkylaminocarbonyl group, an aralkyl group or an arenesulfonyloxy group), a heterocyclic carbonyl group or a cyano group; an aryl group which may be substituted by a hydroxyl group, a lower alkyloxy group, a carbamoyloxy group or a di-lower alkylamino group; or a heterocyclic group which may be substituted by a lower alkyl group or an amino group.

12. A 1,2-benzoisoxazole compound or its salt according to claim 9, wherein $R_4$ is a group represented by the formula:

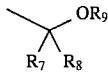

wherein $R_7$ and $R_8$ represent hydrogen atoms or lower alkyl group; $R_9$ represents a lower alkyl group, a lower alkenyl group, a lower alkynyl group, an aralkyl group or a substituted or unsubstituted carbamoyl group.

13. A 1,2-benzoisoxazole compound or its salt according to claim 12, wherein $R_9$ is a carbamoyl group which may be substituted by a lower alkyl group, a cycloalkyl group, a lower alkyloxy group, a lower alkyloxycarbonyl group, a carbamoyl group or an amino group.

14. A 1,2-benzoisoxazole compound or its salt according to claim 1, wherein R is a hydrogen atom or a halogen atom; $R_1$, $R_2$, $R_5$ and $R_6$ are hydrogen atoms; $R_3$ is a hydrogen atom or a lower alkyl group; and $R_4$ is a lower alkyl group or a group represented by the formula:

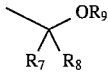

wherein $R_7$ and $R_8$ represent hydrogen atoms and $R_9$ represents a lower alkyl group or a carbamoyl group.

15. 3-(2-Amino-3-carbamoyloxypropoxy)-1,2-benzoisoxazole or its salt.

16. 3-(2-Amino-3-methoxypropoxy)-5-chloro-1,2-benzoisoxazole or its salt.

17. A brain-protecting agent comprising a 1,2-benzoisoxazole compound represented by the following general formula or its salt:

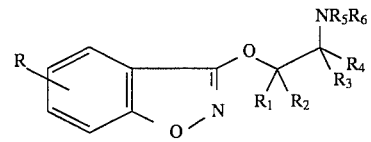

wherein R represents at least one member selected from hydrogen atom, halogen atoms, nitro group, cyano group, hydroxyl group, and substituted or unsubstituted lower alkyl, lower alkenyl, lower alkynyl, aralkyl, aryl, lower alkyloxy, cycloalkyl, aralkyloxy, aryloxy, amino, lower acyl, arylcarbonyl, lower alkanesulfonyl, arenesulfonyl, lower alkylthio, carbamoyl, heterocyclic, lower alkylene and lower alkenylene groups; $R_1$ and $R_2$, which may be the same or different, represent hydrogen atoms or substituted or unsubstituted lower alkyl groups; $R_3$ represents a hydrogen atom or a substituted or unsubstituted lower alkyl, aryl, aralkyl or heterocyclic group; $R_4$ represents a substituted or unsubstituted lower alkyl, aryl or heterocyclic group, or alternatively $R_3$ and $R_4$, when taken together, represent a lower alkylene group; $R_5$ and $R_6$, which may be the same or different, represent hydrogen atoms or substituted or unsubstituted lower alkyl, lower alkenyl, lower alkynyl, lower acyl, lower alkyloxycarbonyl or aralkyl groups.

18. A brain-protecting agent according to claim 17, wherein $R_3$ is a hydrogen atom or a substituted or unsubstituted lower alkyl group; and $R_4$ is a substituted or unsubstituted lower alkyl group represented by the formula:

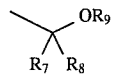

wherein $R_7$ and $R_8$ represent hydrogen atoms or substituted or unsubstituted lower alkyl groups and $R_9$ represents a substituted or unsubstituted lower alkyl, lower alkenyl, lower alkynyl, cycloalkyl, aralkyl or carbamoyl group.

19. A brain-protecting agent according to claim 17, wherein R is a hydrogen atom, a halogen atom, a substituted or unsubstituted lower alkyl, lower alkyloxy, aralkyl or aralkyloxy group; $R_1$ and $R_2$ are hydrogen atoms; $R_3$ represents a hydrogen atom or a substituted or unsubstituted lower alkyl, aryl, aralkyl or heterocyclic group; $R_4$ is a substituted or unsubstituted aryl or heterocyclic group or alternatively $R_3$ and $R_4$, when taken together, are a lower alkylene group; and $R_5$ and $R_6$, which may be the same or different, are hydrogen atoms or substituted or unsubstituted lower alkyl, lower acyl, lower alkyloxycarbonyl or aralkyl groups.

20. A brain-protecting agent according to claim 17, wherein R is a hydrogen atom, a halogen atom or a substituted or unsubstituted lower alkyl, lower alkyloxy, aralkyl or aralkyloxy group; $R_1$ and $R_2$ are hydrogen atoms; $R_3$ is a hydrogen atom or a substituted or unsubstituted lower alkyl group; $R_4$ is a substituted or unsubstituted lower alkyl group; and $R_5$ and $R_6$ are hydrogen atoms or substituted or unsubstituted lower alkyl, lower acyl, lower alkyloxycarbonyl or aralkyl groups.

21. A brain-protecting agent according to claim 17, wherein R is a hydrogen atom, a halogen atom, a nitro group, a cyano group, a hydroxyl group or a substituted or unsubstituted lower alkyl, lower alkenyl, aryl, lower alkyloxy, aralkyloxy, aryloxy, amino, arylcarbonyl, arenesulfonyl, lower alkylthio, heterocyclic or lower alkenylene group.

22. A brain-protecting agent according to claim 21, wherein the substituents of the substituted or unsubstituted lower alkyl, lower alkenyl, lower alkyloxy, aralkyloxy, arylcarbonyl, arenesulfonyl, lower alkylthio, heterocyclic and lower alkenylene groups for R are at least one group selected from halogen atoms and lower alkyloxy groups; the substituents of the substituted or unsubstituted aryl and aryloxy groups for R are at least one group selected from halogen atoms and nitro group; and the substituents of the substituted or unsubstituted amino group for R are at least one group selected from lower alkyl groups, lower acyl groups, arylcarbonyl groups and lower alkyloxycarbonyl groups.

23. A brain-protecting agent according to claim 21, wherein $R_3$ is a hydrogen atom or a lower alkyl group.

24. A brain-protecting agent according to claim 23, wherein $R_1$ and $R_2$ are hydrogen atoms or lower alkyl groups.

25. A brain-protecting agent according to claim 24, wherein $R_5$ or $R_6$ is hydrogen atom, lower alkyl group, lower acyl group, lower alkyloxycarbonyl group or substituted or unsubstituted aralkyl group.

26. A brain-protecting agent according to claim 25, wherein $R_5$ or $R_6$ is aralkyl group which may be substituted by a hydroxyl group or a lower alkyl group.

27. A brain-protecting agent according to claim 25, wherein $R_4$ is a lower alkyl group which may be substituted by a halogen atom, a hydroxyl group, a lower alkyloxy group, a lower alkylthio group, a lower alkanesulfinyl group, a lower alkanesulfonyl group, a carbamoyl group, a carbamoyloxy group, a heterocyclic group (which may be substituted by a hydroxyl group, a di-lower alkylaminocarbonyl group, an aralkyl group or an arenesulfonyloxy group), a heterocyclic carbonyl group or a cyano group; an aryl group which may be substituted by a hydroxyl group, a lower alkyloxy group, a carbamoyloxy group or a di-lower alkylamino group; or a heterocyclic group which may be substituted by a lower alkyl group or an amino group.

28. A brain-protecting agent according to claim 25, wherein $R_4$ is a group represented by the formula:

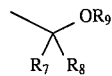

wherein $R_7$ and $R_8$ represent hydrogen atoms or lower alkyl groups; $R_9$ represents a lower alkyl group, a lower alkenyl group, a lower alkynyl group, an aralkyl group or a substituted or unsubstituted carbamoyl group.

29. A brain-protecting agent according to claim 28, wherein $R_9$ is a carbamoyl group which may be substituted by a lower alkyl group, a cycloalkyl group, a lower alkyloxy group, a lower alkyloxycarbonyl group, a carbamoyl group or an amino group.

30. A brain-protecting agent according to claim 17, wherein R is a hydrogen atom or a halogen atom; $R_1$, $R_2$, $R_5$ and $R_6$ are hydrogen atoms; $R_3$ is a hydrogen atom or a lower alkyl group; and $R_4$ is a lower alkyl group or a group represented by the formula:

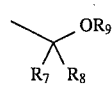

wherein $R_7$ and $R_8$ represent hydrogen atoms and $R_9$ represents a lower alkyl group or a carbamoyl group.

31. A brain-protecting agent according to claim 17 which is selected from 3-(2-amino-3-carbamoyloxypropoxy)-1,2-benzoisoxazole or its salt or 3-(2-amino-3-methoxypropoxy)-5-chloro-1,2-benzoisoxazole or its salt.

32. A method for treating cerebral circulatory disorder, head injury sequelae and/or epilepsy which comprises administering to a patient in need thereof an effective amount of the 1-2-benzoisoxazole compound or its salt according to claim 1.

* * * * *

UNITED STATES PATENT AND TRADEMARK OFFICE
CERTIFICATE OF CORRECTION

PATENT NO. : 5,578,627
DATED : November 26, 1996
INVENTOR(S) : Kenji TAKEDA, et al.

It is certified that error appears in the above-indentified patent and that said Letters Patent is hereby corrected as shown below:

On the title page, Item [30], the Foreign Application Priority Data, should read:

```
--Oct. 28, 1992  [JP] Japan.....4-312743
  Jul.  2, 1993  [JP] Japan.....5-238688
  Jul. 15, 1993  [JP] Japan.....5-197776--
```

Signed and Sealed this

Eighteenth Day of March, 1997

Attest:

BRUCE LEHMAN

*Attesting Officer*     Commissioner of Patents and Trademarks